(12) United States Patent
Haas et al.

(10) Patent No.: US 10,577,592 B2
(45) Date of Patent: *Mar. 3, 2020

(54) COMPOSITIONS AND METHODS FOR PROTEIN GLYCOSYLATION

(71) Applicant: GLAXOSMITHKLINE BIOLOGICALS, S.A., Rixensart (BE)

(72) Inventors: Jurgen Haas, Basel (CH); Julian Ihssen, Dübendorf (CH); Michael Thomas Kowarik, Schlieren (CH); Torsten Franz Schwede, Basel (CH); Linda Christiane Thöny-Meyer, Dübendorf (CH)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/177,562

(22) Filed: Nov. 1, 2018

(65) Prior Publication Data

US 2019/0078064 A1  Mar. 14, 2019

Related U.S. Application Data

(63) Continuation of application No. 15/540,690, filed as application No. PCT/EP2015/081229 on Dec. 24, 2015, now Pat. No. 10,150,952.

(60) Provisional application No. 62/097,975, filed on Dec. 30, 2014, provisional application No. 62/098,071, filed on Dec. 30, 2014.

(51) Int. Cl.
*C12N 9/10* (2006.01)
*C12P 21/00* (2006.01)

(52) U.S. Cl.
CPC .......... *C12N 9/1081* (2013.01); *C12P 21/005* (2013.01)

(58) Field of Classification Search
CPC .................... C12N 9/1081; C12P 21/005
See application file for complete search history.

(56) References Cited

PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Fry et al., GenBank accession No. O86154, Oct. 31, 2006.*
Miller et al., GenBank accession No. B9KDD4, May 29, 2013.*

* cited by examiner

*Primary Examiner* — Delia M Ramirez
(74) *Attorney, Agent, or Firm* — Dana L. Broughton

(57) ABSTRACT

Described herein are oligosaccharyl transferases for use in N-glycosylating proteins of interest in vitro and in host cells. Methods for using such oligosaccharyl transferases, nucleic acids encoding such oligosaccharyl transferases, and host cells comprising such oligosaccharyl transferases are also provided herein. Glycoconjugates generated by using such oligosaccharyl transferases are also provided herein.

19 Claims, 21 Drawing Sheets

Figure 1:
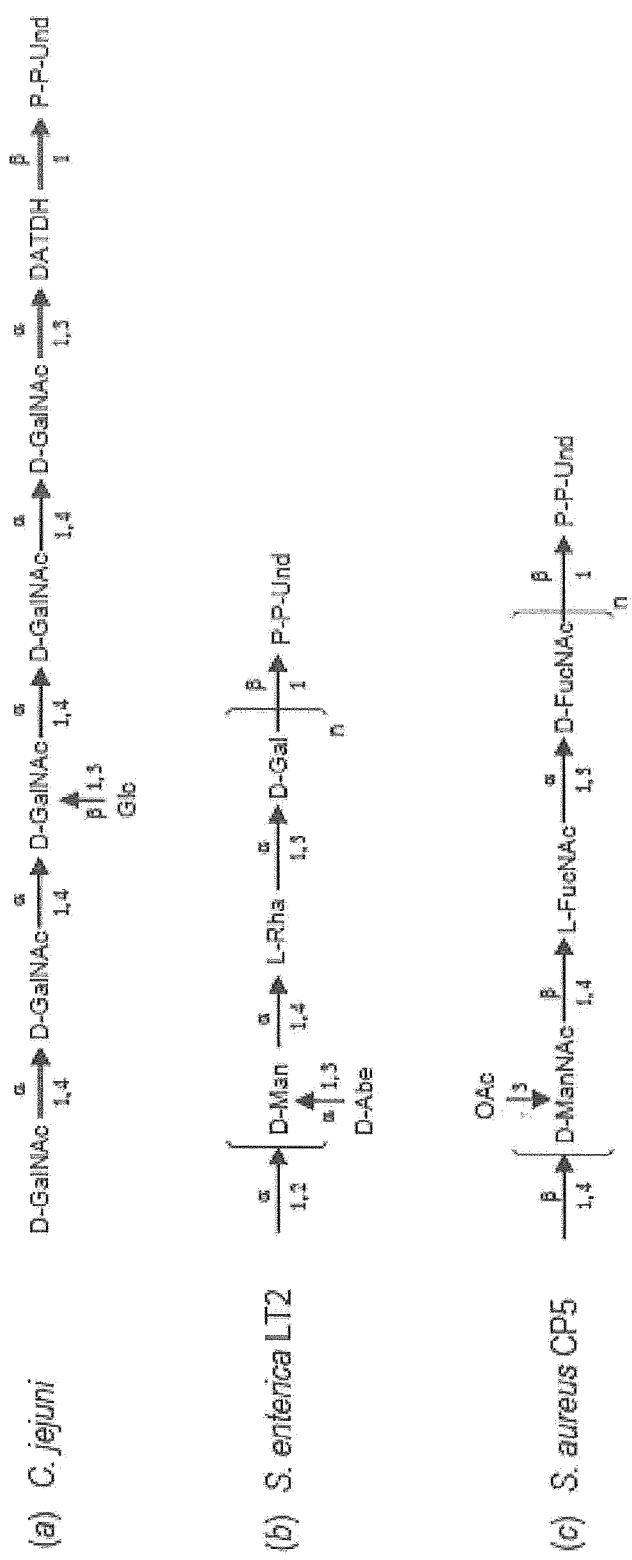

Specification includes a Sequence Listing.

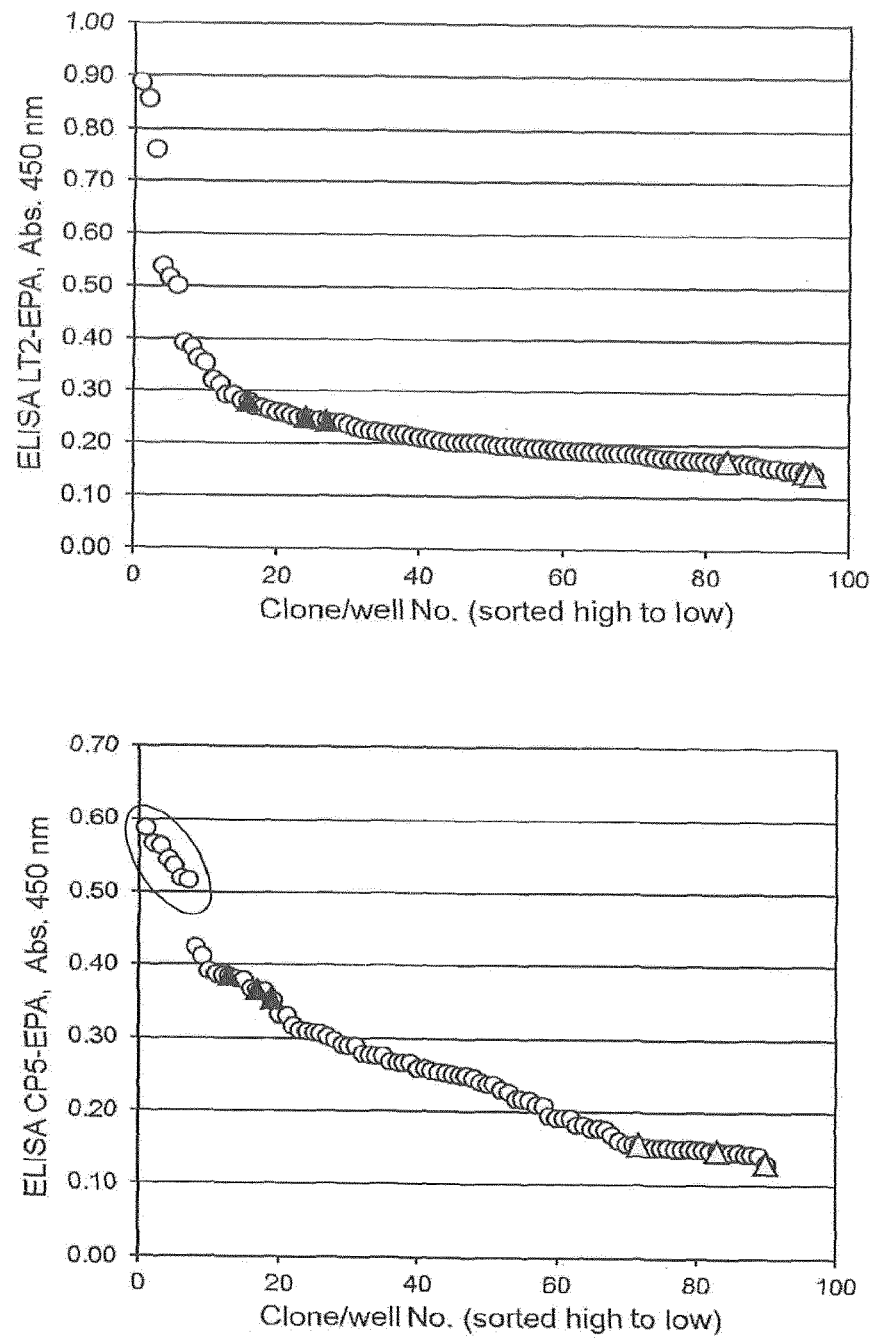
FIG. 3A-B

FIG. 4A

FIG. 4B

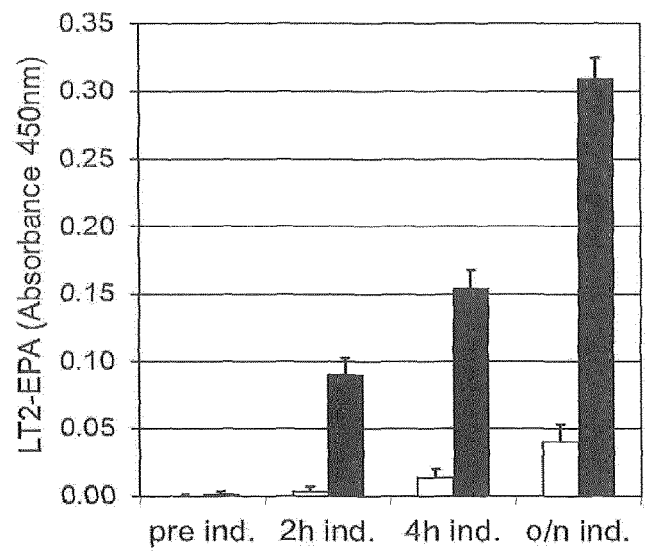
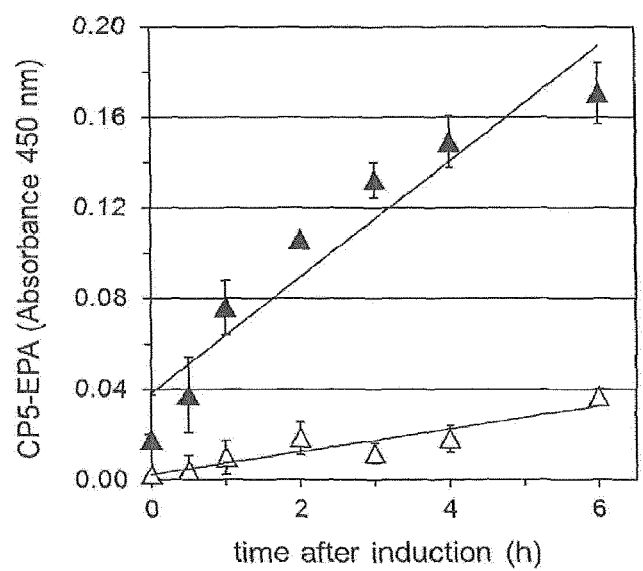
FIG. 6A-B

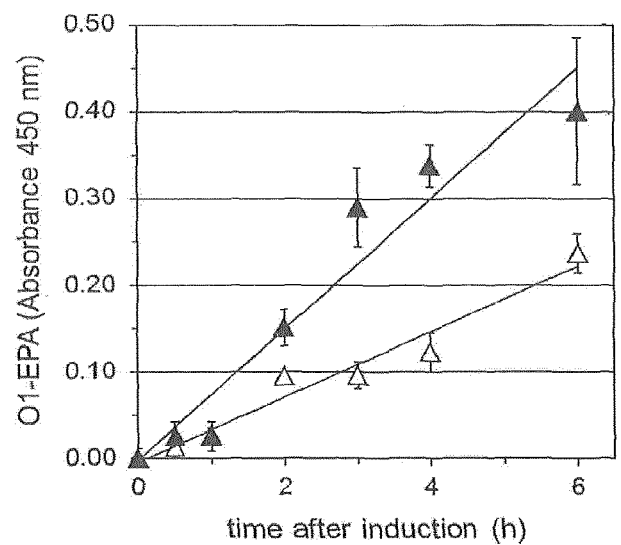
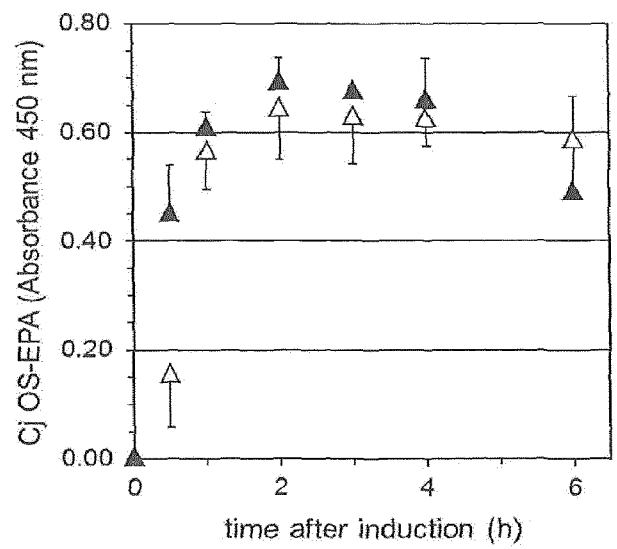
FIG. 6C-D

Before induction
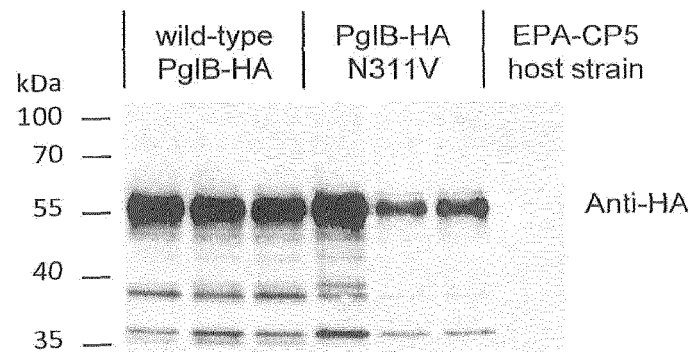
3h after IPTG and L-arabinose induction
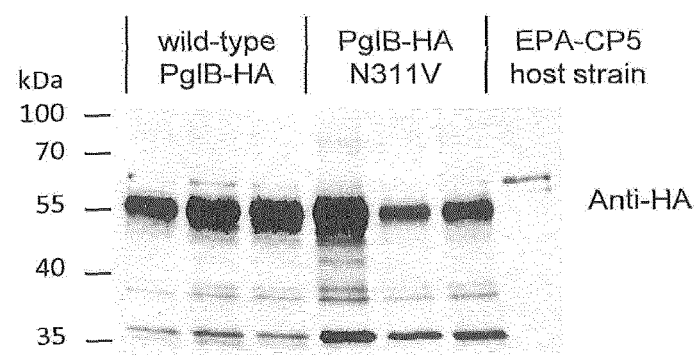
6h after IPTG and L-arabinose induction
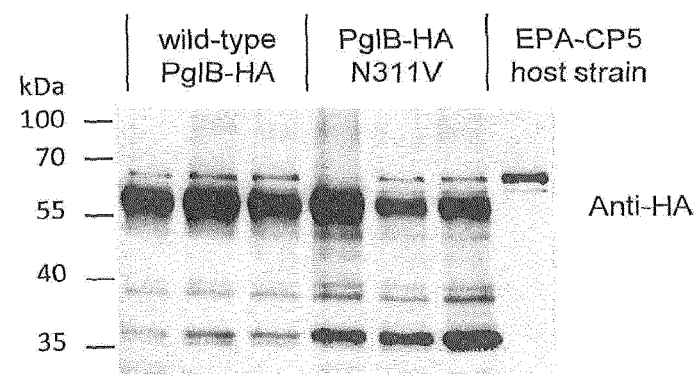
FIG. 8A

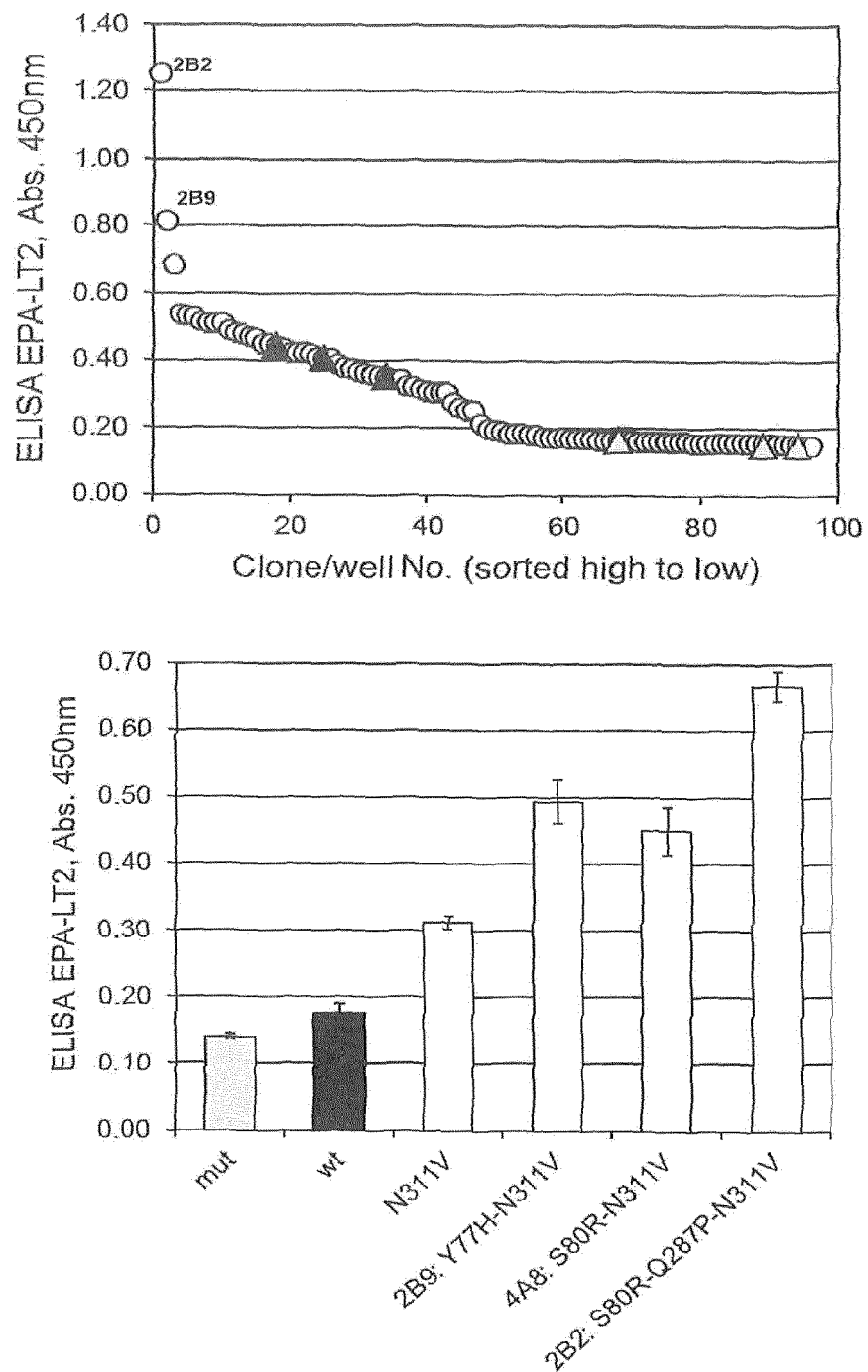
FIG. 9A-B

SEQUENCE LISTING

<160> NUMBER OF SEQ ID NOS: 116

<210> SEQ ID NO 1
<211> LENGTH: 722
<212> TYPE: PRT
<213> ORGANISM: Campylobacter jejuni

<400> SEQUENCE: 1

| Met | Leu | Lys | Lys | Glu | Tyr | Leu | Lys | Asn | Pro | Tyr | Leu | Val | Leu | Phe | Ala |
|---|---|---|---|---|---|---|---|---|---|---|---|---|---|---|---|
| 1 | | | | 5 | | | | | 10 | | | | | 15 | |

| Met | Ile | Ile | Leu | Ala | Tyr | Val | Phe | Ser | Val | Phe | Cys | Arg | Phe | Tyr | Trp |
| | | | 20 | | | | | 25 | | | | | 30 | | |

| Val | Trp | Trp | Ala | Ser | Glu | Phe | Asn | Glu | Tyr | Phe | Phe | Asn | Asn | Gln | Leu |
| | | 35 | | | | | 40 | | | | | 45 | | | |

| Met | Ile | Ile | Ser | Asn | Asp | Gly | Tyr | Ala | Phe | Ala | Glu | Gly | Ala | Arg | Asp |
| | 50 | | | | | 55 | | | | | 60 | | | | |

| Met | Ile | Ala | Gly | Phe | His | Gln | Pro | Asn | Asp | Leu | Ser | Tyr | Tyr | Gly | Ser |
| 65 | | | | | 70 | | | | | 75 | | | | | 80 |

| Ser | Leu | Ser | Ala | Leu | Thr | Tyr | Trp | Leu | Tyr | Lys | Ile | Thr | Pro | Phe | Ser |
| | | | | 85 | | | | | 90 | | | | | 95 | |

| Phe | Glu | Ser | Ile | Ile | Leu | Tyr | Met | Ser | Thr | Phe | Leu | Ser | Ser | Leu | Val |
| | | | | 100 | | | | | 105 | | | | | 110 | |

| Val | Ile | Pro | Thr | Ile | Leu | Leu | Ala | Asn | Glu | Tyr | Lys | Arg | Pro | Leu | Met |
| | | | 115 | | | | | 120 | | | | | 125 | | |

| Gly | Phe | Val | Ala | Ala | Leu | Leu | Ala | Ser | Ile | Ala | Asn | Ser | Tyr | Tyr | Asn |
| | 130 | | | | | 135 | | | | | 140 | | | | |

| Arg | Thr | Met | Ser | Gly | Tyr | Tyr | Asp | Thr | Asp | Met | Leu | Val | Ile | Val | Leu |
| 145 | | | | | 150 | | | | | 155 | | | | | 160 |

| Pro | Met | Phe | Ile | Leu | Phe | Phe | Met | Val | Arg | Met | Ile | Leu | Lys | Lys | Asp |
| | | | | 165 | | | | | 170 | | | | | 175 | |

| Phe | Phe | Ser | Leu | Ile | Ala | Leu | Pro | Leu | Phe | Ile | Gly | Ile | Tyr | Leu | Trp |
| | | | | 180 | | | | | 185 | | | | | 190 | |

| Trp | Tyr | Pro | Ser | Ser | Tyr | Thr | Leu | Asn | Val | Ala | Leu | Ile | Gly | Leu | Phe |
| | | | 195 | | | | | 200 | | | | | 205 | | |

| Leu | Ile | Tyr | Thr | Leu | Ile | Phe | His | Arg | Lys | Glu | Lys | Ile | Phe | Tyr | Ile |
| | 210 | | | | | 215 | | | | | 220 | | | | |

| Ala | Val | Ile | Leu | Ser | Ser | Leu | Thr | Leu | Ser | Asn | Ile | Ala | Trp | Phe | Tyr |
| 225 | | | | | 230 | | | | | 235 | | | | | 240 |

| Gln | Ser | Ala | Ile | Ile | Val | Ile | Leu | Phe | Ala | Leu | Phe | Ala | Leu | Glu | Gln |
| | | | | 245 | | | | | 250 | | | | | 255 | |

| Lys | Arg | Leu | Asn | Phe | Met | Ile | Ile | Gly | Ile | Leu | Gly | Ser | Ala | Thr | Leu |
| | | | | 260 | | | | | 265 | | | | | 270 | |

| Ile | Phe | Leu | Ile | Leu | Ser | Gly | Gly | Val | Asp | Pro | Ile | Leu | Tyr | Gln | Leu |
| | | | 275 | | | | | 280 | | | | | 285 | | |

| Lys | Phe | Tyr | Ile | Phe | Arg | Ser | Asp | Glu | Ser | Ala | Asn | Leu | Thr | Gln | Gly |
| | 290 | | | | | 295 | | | | | 300 | | | | |

| Phe | Met | Tyr | Phe | Asn | Val | Asn | Gln | Thr | Ile | Gln | Glu | Val | Glu | Asn | Val |
| 305 | | | | | 310 | | | | | 315 | | | | | 320 |

| Asp | Leu | Ser | Glu | Phe | Met | Arg | Arg | Ile | Ser | Gly | Ser | Glu | Ile | Val | Phe |
| | | | | 325 | | | | | 330 | | | | | 335 | |

| Leu | Phe | Ser | Leu | Phe | Gly | Phe | Val | Trp | Leu | Leu | Arg | Lys | His | Lys | Ser |
| | | | | 340 | | | | | 345 | | | | | 350 | |

| Met | Ile | Met | Ala | Leu | Pro | Ile | Leu | Val | Leu | Gly | Phe | Leu | Ala | Leu | Lys |
| | | | 355 | | | | | 360 | | | | | 365 | | |

Gly Gly Leu Arg Phe Thr Ile Tyr Ser Val Pro Val Met Ala Leu Gly
370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
450                 455                 460

Arg Tyr Tyr Ser Asp Val Lys Thr Leu Val Asp Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
        515                 520                 525

Met Met Lys Asp Tyr Asn Gln Ser Asn Val Asp Leu Phe Leu Ala Ser
530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Phe Arg Ser Phe Lys Ile
610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
690                 695                 700

Asp Ala Lys Val Phe Lys Leu Lys Ile Tyr Pro Tyr Asp Val Pro Asp
705                 710                 715                 720

Tyr Ala

<210> SEQ ID NO 2
<211> LENGTH: 712
<212> TYPE: PRT
<213> ORGANISM: Campylobacter lari

<400> SEQUENCE: 2

Met Lys Leu Gln Gln Asn Phe Thr Asp Asn Asn Ser Ile Lys Tyr Thr
1               5                   10                  15

```
Cys Ile Leu Ile Leu Ile Ala Phe Ala Phe Ser Val Leu Cys Arg Leu
             20                  25                  30

Tyr Trp Val Ala Trp Ala Ser Glu Phe Tyr Glu Phe Phe Asn Asp
         35                  40                  45

Gln Leu Met Ile Thr Thr Asn Asp Gly Tyr Ala Phe Ala Glu Gly Ala
 50                  55                  60

Arg Asp Met Ile Ala Gly Phe His Gln Pro Asn Asp Leu Ser Tyr Phe
 65                  70                  75                  80

Gly Ser Ser Leu Ser Thr Leu Thr Tyr Trp Leu Tyr Ser Ile Leu Pro
                 85                  90                  95

Phe Ser Phe Glu Ser Ile Ile Leu Tyr Met Ser Ala Phe Phe Ala Ser
                100                 105                 110

Leu Ile Val Val Pro Ile Ile Leu Ile Ala Arg Glu Tyr Lys Leu Thr
            115                 120                 125

Thr Tyr Gly Phe Ile Ala Ala Leu Leu Gly Ser Ile Ala Asn Ser Tyr
        130                 135                 140

Tyr Asn Arg Thr Met Ser Gly Tyr Tyr Asp Thr Asp Met Leu Val Leu
145                 150                 155                 160

Val Leu Pro Met Leu Ile Leu Leu Thr Phe Ile Arg Leu Thr Ile Asn
                165                 170                 175

Lys Asp Ile Phe Thr Leu Leu Leu Ser Pro Val Phe Ile Met Ile Tyr
            180                 185                 190

Leu Trp Trp Tyr Pro Ser Ser Tyr Ser Leu Asn Phe Ala Met Ile Gly
        195                 200                 205

Leu Phe Gly Leu Tyr Thr Leu Val Phe His Arg Lys Glu Lys Ile Phe
210                 215                 220

Tyr Leu Thr Ile Ala Leu Met Ile Ile Ala Leu Ser Met Leu Ala Trp
225                 230                 235                 240

Gln Tyr Lys Leu Ala Leu Ile Val Leu Leu Phe Ala Ile Phe Ala Phe
            245                 250                 255

Lys Glu Glu Lys Ile Asn Phe Tyr Met Ile Trp Ala Leu Ile Phe Ile
        260                 265                 270

Ser Ile Leu Ile Leu His Leu Ser Gly Gly Leu Asp Pro Val Leu Tyr
        275                 280                 285

Gln Leu Lys Phe Tyr Val Phe Lys Ala Ser Asp Val Gln Asn Leu Lys
290                 295                 300

Asp Ala Ala Phe Met Tyr Phe Asn Val Asn Glu Thr Ile Met Glu Val
305                 310                 315                 320

Asn Thr Ile Asp Pro Glu Val Phe Met Gln Arg Ile Ser Ser Ser Val
            325                 330                 335

Leu Val Phe Ile Leu Ser Phe Ile Gly Phe Ile Leu Leu Cys Lys Asp
        340                 345                 350

His Lys Ser Met Leu Leu Ala Leu Pro Met Leu Ala Leu Gly Phe Met
        355                 360                 365

Ala Leu Arg Ala Gly Leu Arg Phe Thr Ile Tyr Ala Val Pro Val Met
    370                 375                 380

Ala Leu Gly Phe Gly Tyr Phe Leu Tyr Ala Phe Phe Asn Phe Leu Glu
385                 390                 395                 400

Lys Lys Gln Ile Lys Leu Ser Leu Arg Asn Lys Asn Ile Leu Leu Ile
                405                 410                 415

Leu Ile Ala Phe Phe Ser Ile Ser Pro Ala Leu Met His Ile Tyr Tyr
            420                 425                 430

Tyr Lys Ser Ser Thr Val Phe Thr Ser Tyr Glu Ala Ser Ile Leu Asn
```

-continued

```
                435                 440                 445
Asp Leu Lys Asn Lys Ala Gln Arg Glu Asp Tyr Val Val Ala Trp Trp
450                 455                 460

Asp Tyr Gly Tyr Pro Ile Arg Tyr Tyr Ser Asp Val Lys Thr Leu Ile
465                 470                 475                 480

Asp Gly Gly Lys His Leu Gly Lys Asp Asn Phe Phe Ser Ser Phe Val
                485                 490                 495

Leu Ser Lys Glu Gln Ile Pro Ala Ala Asn Met Ala Arg Leu Ser Val
            500                 505                 510

Glu Tyr Thr Glu Lys Ser Phe Lys Glu Asn Tyr Pro Asp Val Leu Lys
        515                 520                 525

Ala Met Val Lys Asp Tyr Asn Lys Thr Ser Ala Lys Asp Phe Leu Glu
    530                 535                 540

Ser Leu Asn Asp Lys Asp Phe Lys Phe Asp Thr Asn Lys Thr Arg Asp
545                 550                 555                 560

Val Tyr Ile Tyr Met Pro Tyr Arg Met Leu Arg Ile Met Pro Val Val
                565                 570                 575

Ala Gln Phe Ala Asn Thr Asn Pro Asp Asn Gly Glu Gln Glu Lys Ser
            580                 585                 590

Leu Phe Phe Ser Gln Ala Asn Ala Ile Ala Gln Asp Lys Thr Thr Gly
        595                 600                 605

Ser Val Met Leu Asp Asn Gly Val Glu Ile Ile Asn Asp Phe Arg Ala
    610                 615                 620

Leu Lys Val Glu Gly Ala Ser Ile Pro Leu Lys Ala Phe Val Asp Ile
625                 630                 635                 640

Glu Ser Ile Thr Asn Gly Lys Phe Tyr Tyr Asn Glu Ile Asp Ser Lys
                645                 650                 655

Ala Gln Ile Tyr Leu Leu Phe Leu Arg Glu Tyr Lys Ser Phe Val Ile
            660                 665                 670

Leu Asp Glu Ser Leu Tyr Asn Ser Ser Tyr Ile Gln Met Phe Leu Leu
        675                 680                 685

Asn Gln Tyr Asp Gln Asp Leu Phe Glu Gln Ile Thr Asn Asp Thr Arg
    690                 695                 700

Ala Lys Ile Tyr Arg Leu Lys Arg
705                 710
```

<210> SEQ ID NO 3
<211> LENGTH: 42
<212> TYPE: DNA
<213> ORGANISM: Campylobacter jejuni
<220> FEATURE:
<221> NAME/KEY: misc_feature
<222> LOCATION: (21)..(23)
<223> OTHER INFORMATION: n is a, c, g, or t

<400> SEQUENCE: 3
gcttcatgta cttcaacgtt nnncagacga tccaagaagt gg     42

<210> SEQ ID NO 4
<211> LENGTH: 43
<212> TYPE: DNA
<213> ORGANISM: Campylobacter jejuni
<220> FEATURE:
<221> NAME/KEY: misc_feature
<222> LOCATION: (22)..(24)
<223> OTHER INFORMATION: n is a, c, g, or t

<400> SEQUENCE: 4
catcagccga acgatctgag tnnntacggt agctctctgt ccg            43

<210> SEQ ID NO 5
<211> LENGTH: 44
<212> TYPE: DNA
<213> ORGANISM: Campylobacter jejuni
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t

<400> SEQUENCE: 5
cgatgttaaa acgctggtcg acnntnntaa acacctgggc aagg            44

<210> SEQ ID NO 6
<211> LENGTH: 44
<212> TYPE: DNA
<213> ORGANISM: Campylobacter jejuni
<220> FEATURE:
<221> NAME/KEY: misc_feature
<222> LOCATION: (24)..(26)
<223> OTHER INFORMATION: n is a, c, g, or t

<400> SEQUENCE: 6
cgaacgatct gagttattac ggtnnntctc tgtccgcgct gacc            44

<210> SEQ ID NO 7
<211> LENGTH: 49
<212> TYPE: DNA
<213> ORGANISM: Campylobacter jejuni
<220> FEATURE:
<221> NAME/KEY: misc_feature
<222> LOCATION: (22)..(24)
<223> OTHER INFORMATION: n is a, c, g, or t

<400> SEQUENCE: 7
ggtgttgatc cgattctgta cnnnctgaaa ttttatatct tccgctcag            49

<210> SEQ ID NO 8
<211> LENGTH: 49
<212> TYPE: DNA
<213> ORGANISM: Campylobacter jejuni
<220> FEATURE:
<221> NAME/KEY: misc_feature
<222> LOCATION: (22)..(24)
<223> OTHER INFORMATION: n is a, c, g, or t

<400> SEQUENCE: 8
gttgatccga ttctgtacca gnnnaaattt tatatcttcc gctcagatg            49

<210> SEQ ID NO 9
<211> LENGTH: 51
<212> TYPE: DNA
<213> ORGANISM: Campylobacter jejuni
<220> FEATURE:
<221> NAME/KEY: misc_feature
<222> LOCATION: (22)..(24)
<223> OTHER INFORMATION: n is a, c, g, or t

<400> SEQUENCE: 9
gatccgattc tgtaccagct gnnntttat atcttccgct cagatgaatc g            51

<210> SEQ ID NO 10
<211> LENGTH: 48

<212> TYPE: DNA
<213> ORGANISM: Campylobacter jejuni
<220> FEATURE:
<221> NAME/KEY: misc_feature
<222> LOCATION: (22)..(24)
<223> OTHER INFORMATION: n is a, c, g, or t

<400> SEQUENCE: 10
ccgattctgt accagctgaa annntatatc ttccgctcag atgaatcg                48

<210> SEQ ID NO 11
<211> LENGTH: 47
<212> TYPE: DNA
<213> ORGANISM: Campylobacter jejuni
<220> FEATURE:
<221> NAME/KEY: misc_feature
<222> LOCATION: (24)..(26)
<223> OTHER INFORMATION: n is a, c, g, or t

<400> SEQUENCE: 11
cgattctgta ccagctgaaa tttnnnatct tccgctcaga tgaatcg                 47

<210> SEQ ID NO 12
<211> LENGTH: 49
<212> TYPE: DNA
<213> ORGANISM: Campylobacter jejuni
<220> FEATURE:
<221> NAME/KEY: misc_feature
<222> LOCATION: (26)..(28)
<223> OTHER INFORMATION: n is a, c, g, or t

<400> SEQUENCE: 12
gtaccagctg aaattttata tcttcnnntc agatgaatcg gcaaacctg              49

<210> SEQ ID NO 13
<211> LENGTH: 50
<212> TYPE: DNA
<213> ORGANISM: Campylobacter jejuni
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 13
catcagccga acgatctgag tynttacggt ngttctctgt ccgcgctgac             50

<210> SEQ ID NO 14
<211> LENGTH: 58
<212> TYPE: DNA
<213> ORGANISM: Campylobacter jejuni
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 14
cggtgttgat ccgattctgt acnngntnna nttttatatc ttccgctcag atgaatcg        58

<210> SEQ ID NO 15
<211> LENGTH: 58
<212> TYPE: DNA
<213> ORGANISM: Campylobacter jejuni
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 15
cggtgttgat ccgattctgt acnngntncg ttttatatc ttccgctcag atgaatcg        58

<210> SEQ ID NO 16
<211> LENGTH: 57
<212> TYPE: DNA
<213> ORGANISM: Campylobacter jejuni
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 16
gtagatggtg gaaagcattt nggtnntnnt aattttttcc cttcttttgc tttaagc        57

<210> SEQ ID NO 17
<211> LENGTH: 57
<212> TYPE: DNA
<213> ORGANISM: Campylobacter jejuni
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 17
gcttaaagca aaagaaggga aaaaattann annaccnaaa tgctttccac catctac        57

<210> SEQ ID NO 18
<211> LENGTH: 53
<212> TYPE: PRT
<213> ORGANISM: Campylobacter jejuni

<400> SEQUENCE: 18

Gly Val Asp Pro Ile Leu Tyr Gln Leu Lys Phe Tyr Ile Phe Arg Ser

```
                1               5                   10                  15
           Asp Glu Ser Ala Asn Leu Thr Gln Gly Phe Met Tyr Phe Asn Val Asn
                            20                  25                  30

Gln Thr Ile Gln Glu Val Glu Asn Val Asp Leu Ser Glu Phe Met Arg
                        35                  40                  45

Arg Ile Ser Gly Ser
                    50

<210> SEQ ID NO 19
<211> LENGTH: 53
<212> TYPE: PRT
<213> ORGANISM: Campylobacter coli

<400> SEQUENCE: 19

Gly Ile Asp Pro Ile Leu Tyr Gln Leu Lys Phe Tyr Ile Phe Arg Ser
           1               5                   10                  15

Asp Glu Ser Ala Asn Leu Ala Gln Gly Phe Met Tyr Phe Asn Val Asn
                            20                  25                  30

Gln Thr Ile Gln Glu Val Glu Ser Ile Asp Leu Ser Ile Phe Met Gln
                        35                  40                  45

Arg Ile Ser Gly Ser
                    50

<210> SEQ ID NO 20
<211> LENGTH: 54
<212> TYPE: PRT
<213> ORGANISM: Campylobacter lari

<400> SEQUENCE: 20

Gly Leu Asp Pro Val Leu Tyr Gln Leu Lys Phe Tyr Val Phe Lys Ala
           1               5                   10                  15

Ser Asp Val Gln Asn Leu Lys Asp Ala Ala Phe Met Tyr Phe Asn Val
                            20                  25                  30

Asn Glu Thr Ile Met Glu Val Asn Thr Ile Asp Pro Glu Val Phe Met
                        35                  40                  45

Gln Arg Ile Ser Ser Ser
                    50

<210> SEQ ID NO 21
<211> LENGTH: 53
<212> TYPE: PRT
<213> ORGANISM: Campylobacter upsaliensis

<400> SEQUENCE: 21

Gly Ile Asp Pro Ile Leu Tyr Gln Leu Lys Phe Tyr Leu Leu Arg Ser
           1               5                   10                  15

Asp Glu Ser Ala Ser Leu Ala Arg Gly Phe Ala Tyr Phe Asn Val Asn
                            20                  25                  30

Leu Thr Ile Gln Glu Val Glu Ser Ile Asp Leu Ser Thr Phe Met Gln
                        35                  40                  45

Arg Ile Ser Gly Ser
                    50

<210> SEQ ID NO 22
<211> LENGTH: 52
<212> TYPE: PRT
<213> ORGANISM: Campylobacter curvus

<400> SEQUENCE: 22
```

-continued

Gly Leu Asn Pro Ile Ile Phe Gln Leu Lys Phe Tyr Val Phe Arg Ala
1               5                   10                  15

Val Pro Glu Ser Ala Gly Val Ser Phe Lys Tyr Phe Asn Val Asn Gln
            20                  25                  30

Thr Ile Gln Glu Ser Gly Ile Val Asp Leu Gln Leu Phe Cys Glu Arg
        35                  40                  45

Ile Ser Ser Ser
    50

<210> SEQ ID NO 23
<211> LENGTH: 52
<212> TYPE: PRT
<213> ORGANISM: Campylobacter concisus

<400> SEQUENCE: 23

Gly Leu Asn Pro Ile Ile Phe Gln Leu Lys Phe Tyr Val Phe Arg Asp
1               5                   10                  15

Ala Pro Glu Val Gly Gly Met Ser Phe His Phe Phe Asn Val Asn Gln
            20                  25                  30

Thr Ile Gln Glu Ser Ser Ile Val Asp Phe Thr Leu Phe Cys Glu Arg
        35                  40                  45

Ile Ser Ala Asn
    50

<210> SEQ ID NO 24
<211> LENGTH: 59
<212> TYPE: PRT
<213> ORGANISM: Campylobacter hominis

<400> SEQUENCE: 24

Gly Leu Ser Pro Ile Leu Phe Gln Leu Lys Phe Tyr Ile Phe Arg Gly
1               5                   10                  15

Phe Ala Asp His Ala Asp Ile Leu Ser Asn Ala Asp Lys Ile Val Tyr
            20                  25                  30

Lys Phe Tyr Asn Val Asn Gln Thr Ile Gln Glu Ser Gly Phe Val Ser
        35                  40                  45

Pro Glu Ile Phe Met Gln Arg Ile Ser Ser Asn
    50                  55

<210> SEQ ID NO 25
<211> LENGTH: 52
<212> TYPE: PRT
<213> ORGANISM: Campylobacter gracilis

<400> SEQUENCE: 25

Gly Leu Ser Pro Ile Ile Phe Gln Ala Lys Phe Tyr Ile Phe Arg Ser
1               5                   10                  15

Phe Ala Asp Asn Ala Asp Thr Ala Phe His Phe Phe Asn Val Asn Gln
            20                  25                  30

Thr Ile Gln Glu Ser Gly Ile Val Pro Pro Lys Ile Phe Met Glu Arg
        35                  40                  45

Ile Ser Ser His
    50

<210> SEQ ID NO 26
<211> LENGTH: 57
<212> TYPE: PRT
<213> ORGANISM: Campylobacter showae

<400> SEQUENCE: 26

Gly Leu Asn Gln Ile Leu Phe Gln Leu Lys Phe Tyr Ile Phe Arg Gly
1               5                   10                  15

Val Ser Glu Ser Ser Glu Pro Val Phe His Phe Tyr Asn Val Asn Lys
            20                  25                  30

Thr Ile Met Glu Met Ser Asp Tyr Ser Phe Glu Phe Ser Ile Asn
        35                  40                  45

Ala Phe Ala Lys Arg Ile Ser Gly His
    50                  55

<210> SEQ ID NO 27
<211> LENGTH: 54
<212> TYPE: PRT
<213> ORGANISM: Sulfurimonas autotrophica

<400> SEQUENCE: 27

Gly Phe Asp Pro Ile Trp Ala Gln Leu Lys Gly Tyr Val Phe Arg Asn
1               5                   10                  15

Ser Val Ser Ser Thr Gly Lys Gly Leu Gly Leu His Phe Phe Thr Val
            20                  25                  30

Met Gln Thr Val Arg Glu Ala Gly His Ile Pro Phe Glu Thr Phe Ala
        35                  40                  45

Asn Arg Ile Ser Gly Asn
    50

<210> SEQ ID NO 28
<211> LENGTH: 54
<212> TYPE: PRT
<213> ORGANISM: Sulfurimonas denitrificans

<400> SEQUENCE: 28

Gly Phe Asn Pro Ile Trp Glu Gln Leu Ser Gly Tyr Val Phe Lys Asp
1               5                   10                  15

Ala Ile Ser Val Gly Gln Glu Gly Leu Lys Leu His Phe Tyr Ser Val
            20                  25                  30

Lys Gln Thr Ile Arg Glu Ala Ala Asn Ile Pro Phe Ile Thr Phe Ala
        35                  40                  45

Asn Arg Ile Ser Gly His
    50

<210> SEQ ID NO 29
<211> LENGTH: 54
<212> TYPE: PRT
<213> ORGANISM: Sulfurospirillum deleyianum

<400> SEQUENCE: 29

Gly Phe Glu Pro Ile Trp Val Gln Leu Glu Arg Tyr Val Phe Lys Glu
1               5                   10                  15

Ala Ile Glu Ala Ser Glu Gly Lys Leu Ser Leu His Phe Phe Ser Val
            20                  25                  30

Met Gln Thr Val Arg Glu Ala Gly Gln Ile Ser Phe Thr Val Phe Ala
        35                  40                  45

Glu Arg Ile Ser Gly His
    50

<210> SEQ ID NO 30
<211> LENGTH: 52
<212> TYPE: PRT
<213> ORGANISM: Sulfuricurvum kujiense

```
<400> SEQUENCE: 30

Gly Val Glu Pro Ile Leu His Phe Ile Gln Gly Tyr Phe Asn Gly
1               5                   10                  15

Glu Gly Lys Asn Thr Val Ser Thr Leu Asn Phe Tyr Asn Val Met Ser
                20                  25                  30

Thr Val Arg Glu Ala Gly Gln Ile Pro Phe Asn Val Phe Ala Glu Arg
            35                  40                  45

Ile Ser Gly His
    50

<210> SEQ ID NO 31
<211> LENGTH: 49
<212> TYPE: PRT
<213> ORGANISM: Nautilia profundicola

<400> SEQUENCE: 31

Met Asp Met Phe Ile Asn Lys Phe Leu Val Tyr Phe Asn Arg Ser Asp
1               5                   10                  15

Thr Gly Glu Glu Gly Leu His Phe Tyr Asn Val Ser Lys Thr Ile Arg
                20                  25                  30

Glu Ala Ser Gln Ile Pro Phe Asp Val Val Ala Asn Arg Ile Ser Gly
            35                  40                  45

Gly

<210> SEQ ID NO 32
<211> LENGTH: 49
<212> TYPE: PRT
<213> ORGANISM: Sulfuvorum sp. NBC37-1

<400> SEQUENCE: 32

Val Phe Gly Leu Ile Leu His Lys Ile Ala Thr Tyr Thr Ile Thr Gly
1               5                   10                  15

Thr Lys Glu Ser Gly Leu His Phe Tyr Ala Val Asn Gln Thr Val Arg
                20                  25                  30

Glu Ala Gly Gln Ile Pro Phe Ser Thr Phe Ala Asn Arg Val Ser Gly
            35                  40                  45

Ser

<210> SEQ ID NO 33
<211> LENGTH: 52
<212> TYPE: PRT
<213> ORGANISM: Wolinella succinogenes

<400> SEQUENCE: 33

Ala Leu Ser Pro Leu Trp Tyr Gln Leu Glu Val Tyr Leu Phe Arg Pro
1               5                   10                  15

Ser Val Glu Ala Ser Ala Pro Ser Leu His Phe Tyr Ser Val Val Gln
                20                  25                  30

Thr Ile Arg Glu Ala Ser Thr Leu Ser Leu Glu Lys Leu Ala Ile Arg
            35                  40                  45

Ile Ser Gly His
    50

<210> SEQ ID NO 34
<211> LENGTH: 49
<212> TYPE: PRT
<213> ORGANISM: Caminibacter mediatlanticus

<400> SEQUENCE: 34
```

```
Leu Asn Val Leu Met Ser Glu Ile Asn Ala Tyr Ile Asn Arg Lys Asn
1               5                   10                  15

Asn Asn Ile Leu Gly Leu His Tyr Tyr His Val Tyr Lys Thr Ile Arg
                20                  25                  30

Glu Ala Ser Ala Ile Pro Tyr Asp Leu Val Ala Lys Arg Ile Ser Gly
            35                  40                  45

Asn

<210> SEQ ID NO 35
<211> LENGTH: 49
<212> TYPE: PRT
<213> ORGANISM: Nitratiruptor sp. SB155-2

<400> SEQUENCE: 35

Val Phe Gly Ile Ile Leu His Lys Val Phe Ser Tyr Thr Ser His Thr
1               5                   10                  15

Asp Gln Ile Ala Gly Leu His Phe Leu Asn Val Asn Glu Thr Val Arg
                20                  25                  30

Glu Ala Gly Lys Ile Pro Phe Glu Val Val Ala Asp Arg Ile Val Gly
            35                  40                  45

Ser

<210> SEQ ID NO 36
<211> LENGTH: 53
<212> TYPE: PRT
<213> ORGANISM: Helicobacter pullorum

<400> SEQUENCE: 36

Ile Leu Ala Phe Arg Val Val Pro Glu Ile Phe Ala Ser Val Tyr Val
1               5                   10                  15

Ala Gln Asp Ser Lys Glu Thr Leu Gly Phe Gly Tyr Ala Ser Val Met
                20                  25                  30

Gly Thr Ile Ser Glu Val Ser Lys Ile Asp Phe Trp Asn Phe Val Tyr
            35                  40                  45

Arg Ile Ser Gly Asn
    50

<210> SEQ ID NO 37
<211> LENGTH: 52
<212> TYPE: PRT
<213> ORGANISM: Helicobacter canadensis

<400> SEQUENCE: 37

Val Leu Val Ile Lys Ile Leu Pro Glu Ile Phe Gly Ser Val Tyr Val
1               5                   10                  15

Val Gly Asn Val Ser Asn Val Asp Phe His Tyr Leu Asp Val Met Glu
                20                  25                  30

Ser Ile Ala Glu Val Ser Ser Leu Gly Phe Leu Glu Phe Val Tyr Arg
            35                  40                  45

Ile Ser Gly Asn
    50

<210> SEQ ID NO 38
<211> LENGTH: 61
<212> TYPE: PRT
<213> ORGANISM: Helicobacter winghamensis

<400> SEQUENCE: 38
```

```
Phe Trp Ile Leu Ile Leu Tyr Pro Leu Ile Pro Ser Leu Leu Arg Ser
1               5                   10                  15

Pro Phe Leu Ser Pro Phe Leu Pro Phe Val Glu Ser Thr Leu Gln Gln
            20                  25                  30

Pro Leu Pro Thr Leu Asn Ile Leu Asp Ser Ile Ala Glu Thr Ser Lys
            35                  40                  45

Leu Ser Ile Phe Ser Leu Ala Lys Arg Thr Ser Gly Asn
        50                  55                  60

<210> SEQ ID NO 39
<211> LENGTH: 50
<212> TYPE: PRT
<213> ORGANISM: Desulfurobacterium thermolithotr.

<400> SEQUENCE: 39

Gly Val Phe Asn Ile Val Gly Leu Val Lys Val Tyr Leu Ile Asn Tyr
1               5                   10                  15

Phe Lys Pro Asp Val Ser Gly Gly Phe Pro Asn Val Phe Met Ser Ile
            20                  25                  30

Ser Glu Ala Lys His Phe Asp Ile Thr Lys Ile Ala Gln Leu Ser Thr
            35                  40                  45

Gly Asn
    50

<210> SEQ ID NO 40
<211> LENGTH: 53
<212> TYPE: PRT
<213> ORGANISM: Desulfomicrobium baculatum

<400> SEQUENCE: 40

Ile Gln Ala Leu Val Tyr Arg Leu Tyr Leu Tyr Thr Lys Val Gly Thr
1               5                   10                  15

Pro Asp Met Ile Ser Asn Ala Thr Gly Leu Lys Leu Pro Asp Ile Ala
            20                  25                  30

Gln Ser Val Arg Glu Ala Gln Asn Leu Asp Trp Ser Gln Ile Gly Pro
            35                  40                  45

Arg Leu Gly Gly Asn
        50

<210> SEQ ID NO 41
<211> LENGTH: 49
<212> TYPE: PRT
<213> ORGANISM: Desulfovibrio vulgaris

<400> SEQUENCE: 41

Ser Ile Ala Gly Tyr Val Lys Arg Ser Gly Asp Pro Ser Pro Gly Ala
1               5                   10                  15

Gly Gly Asp Asp Pro Leu Val Tyr Pro Ser Val Ala Gln Ser Ile Ile
            20                  25                  30

Glu Val Gln Asp Leu Ser Leu Ser Glu Val Leu Ser Tyr Phe His Pro
            35                  40                  45

Trp

<210> SEQ ID NO 42
<211> LENGTH: 32
<212> TYPE: PRT
<213> ORGANISM: Desulfovibrio alkaliphilus

<400> SEQUENCE: 42
```

Pro Thr Gly Gln Ile Ala Trp Pro Asp Ile Met Gly Glu Ile Ala Glu
1               5                   10                  15

Ala Gln Val Lys Asp Pro Trp Leu Val Leu Lys Arg Ile His Gly Phe
            20                  25                  30

<210> SEQ ID NO 43
<211> LENGTH: 54
<212> TYPE: PRT
<213> ORGANISM: Desulfohalobium retbaense

<400> SEQUENCE: 43

Ala Ala Val Val Thr Lys Leu Ile Glu Pro Ala Leu Ser Tyr Ala Lys
1               5                   10                  15

Ile Asn Leu Ser Arg Glu Thr Glu Ser Leu Leu Lys Leu Pro Thr Val
            20                  25                  30

Lys Gln Ser Ile Arg Glu Ala Gln Asn Ile Asp Trp Leu Ala Ile Met
        35                  40                  45

Asp Arg Leu Ala Gly His
    50

<210> SEQ ID NO 44
<211> LENGTH: 35
<212> TYPE: PRT
<213> ORGANISM: Deferribacter desulfuricans

<400> SEQUENCE: 44

Thr Ile Ser Lys Glu Asn Leu Ile Gly Phe Pro Asn Ile Leu Gln Thr
1               5                   10                  15

Ile Thr Glu Ala Gln His Lys Pro Ile Lys Val Leu Glu Tyr Ile
            20                  25                  30

Ile Asn Ser
        35

<210> SEQ ID NO 45
<211> LENGTH: 54
<212> TYPE: PRT
<213> ORGANISM: Desulfovibrio salexigens

<400> SEQUENCE: 45

Lys Phe Ile Phe Leu Trp Ser Lys Ile Gln Ser Tyr Leu Lys Pro Val
1               5                   10                  15

Ser Asp Val Val Val Lys Ser Ala Ala Gln Ile His Tyr Pro Ser Ile
            20                  25                  30

Gly Gln Ser Val Ile Glu Val Gln Asn Val Lys Leu Val Ala Leu Leu
        35                  40                  45

Gly Asp Leu Thr Gly Ser
    50

<210> SEQ ID NO 46
<211> LENGTH: 54
<212> TYPE: PRT
<213> ORGANISM: Desulfovibrio piger

<400> SEQUENCE: 46

Leu Leu Gln Thr Ile Thr His Gln Leu Ser Leu Tyr Met Lys Lys Ala
1               5                   10                  15

Glu Val Ser Gly Gly Ser Gly Ala Leu Ala Leu Ile Tyr Pro Pro Ala
            20                  25                  30

Gly Gln Ala Leu Thr Glu Val Gln Asp Leu Gly Leu Leu Ala Val Leu
        35                  40                  45

Ala Tyr Phe His Pro Trp
                50

<210> SEQ ID NO 47
<211> LENGTH: 59
<212> TYPE: PRT
<213> ORGANISM: Desulfovibrio aespoeensis

<400> SEQUENCE: 47

Ser Val Ala Tyr Ser Ala Ala Lys Leu Val Ser Tyr Leu Thr Gly Ala
1               5                   10                  15

Ala Gly Thr Ile Asp Ser Gly Ala Ala Gly Ala Glu Phe Leu Gly Pro
            20                  25                  30

Ile Tyr Pro Ser Ile Leu Gln Ser Ile Ile Glu Val Arg Leu Glu Pro
        35                  40                  45

Leu Ser Ala Ile Met Glu Arg Gly Ala Phe Phe
    50                  55

<210> SEQ ID NO 48
<211> LENGTH: 29
<212> TYPE: PRT
<213> ORGANISM: Cand. Puniceispirillum marinum

<400> SEQUENCE: 48

Thr Leu Val Phe Pro Asn Thr Phe Gln Thr Ile Thr Glu Leu Asn Val
1               5                   10                  15

Ile Pro Phe Thr Asp Leu Leu Arg Gly Ile Thr Tyr Asp
            20                  25

<210> SEQ ID NO 49
<211> LENGTH: 35
<212> TYPE: PRT
<213> ORGANISM: Calditerrivibrio nitroreducens

<400> SEQUENCE: 49

Thr Glu Leu Lys Leu Ala Asn Ile Ser Trp Pro Asn Ile Met Glu Thr
1               5                   10                  15

Ile Ser Glu Ser Asn Lys Lys Asn Trp Gly Ile Leu Ser Met Ile
            20                  25                  30

Leu Gly Asn
        35

<210> SEQ ID NO 50
<211> LENGTH: 24
<212> TYPE: PRT
<213> ORGANISM: Methanothermus fervidus

<400> SEQUENCE: 50

Phe Phe Met Pro Lys Ser Tyr Tyr Pro Asn Ile Tyr Glu Ser Val Val
1               5                   10                  15

Glu Leu Gln Lys Pro Tyr Gly Leu
            20

<210> SEQ ID NO 51
<211> LENGTH: 17
<212> TYPE: PRT
<213> ORGANISM: Campylobacter jejuni

<400> SEQUENCE: 51

Phe His Gln Pro Asn Asp Leu Ser Tyr Tyr Gly Ser Ser Leu Ser Ala
1               5                   10                  15

Leu

<210> SEQ ID NO 52
<211> LENGTH: 17
<212> TYPE: PRT
<213> ORGANISM: Campylobacter coli

<400> SEQUENCE: 52

Phe His Gln Pro Asn Asp Leu Ser Tyr Tyr Gly Ser Ser Leu Ser Thr
1               5                   10                  15

Leu

<210> SEQ ID NO 53
<211> LENGTH: 17
<212> TYPE: PRT
<213> ORGANISM: Campylobacter lari

<400> SEQUENCE: 53

Phe His Gln Pro Asn Asp Leu Ser Tyr Phe Gly Ser Ser Leu Ser Thr
1               5                   10                  15

Leu

<210> SEQ ID NO 54
<211> LENGTH: 17
<212> TYPE: PRT
<213> ORGANISM: Campylobacter upsaliensis

<400> SEQUENCE: 54

Phe His Gln Glu Asn Asp Leu Ser Phe Ile Asn Ser Ser Leu Ser Ile
1               5                   10                  15

Leu

<210> SEQ ID NO 55
<211> LENGTH: 17
<212> TYPE: PRT
<213> ORGANISM: Campylobacter curvus

<400> SEQUENCE: 55

Phe His Gln Pro Asn Asp Leu Ser Tyr Phe Gly Tyr Pro Leu Ser Thr
1               5                   10                  15

Leu

<210> SEQ ID NO 56
<211> LENGTH: 17
<212> TYPE: PRT
<213> ORGANISM: Campylobacter concisus

<400> SEQUENCE: 56

Phe His Gln Glu Asn Asp Leu Ser Tyr Tyr Gly Tyr Pro Leu Ser Thr
1               5                   10                  15

Leu

<210> SEQ ID NO 57
<211> LENGTH: 17
<212> TYPE: PRT
<213> ORGANISM: Campylobacter hominis

<400> SEQUENCE: 57

Phe His Gln Pro Asn Asp Leu Ser Tyr Ile Asn Phe Pro Leu Ser Ile
1               5                   10                  15

Ile

<210> SEQ ID NO 58
<211> LENGTH: 17
<212> TYPE: PRT
<213> ORGANISM: Campylobacter gracilis

<400> SEQUENCE: 58

Phe His Gln Pro Asn Asp Leu Ser Tyr Phe Ser Ala Pro Leu Ser Ile
1               5                   10                  15

Val

<210> SEQ ID NO 59
<211> LENGTH: 17
<212> TYPE: PRT
<213> ORGANISM: Campylobacter showae

<400> SEQUENCE: 59

Phe His Gln Pro Asn Asp Leu Ser Tyr Tyr Gly Arg Ser Met Pro Thr
1               5                   10                  15

Leu

<210> SEQ ID NO 60
<211> LENGTH: 17
<212> TYPE: PRT
<213> ORGANISM: Sulfurimonas autotrophica

<400> SEQUENCE: 60

Phe His Gln Phe Asn Asp Leu Ser Pro Val Thr Ser Ala Ala Ser Gln
1               5                   10                  15

Leu

<210> SEQ ID NO 61
<211> LENGTH: 17
<212> TYPE: PRT
<213> ORGANISM: Sulfurimonas denitrificans

<400> SEQUENCE: 61

Val His Gln Asp Asn Asp Leu Ser Ala Val Asp Leu Ala Ala Ser Gln
1               5                   10                  15

Leu

<210> SEQ ID NO 62
<211> LENGTH: 15
<212> TYPE: PRT
<213> ORGANISM: Sulfurospirillum deleyianum

<400> SEQUENCE: 62

Gln Lys Tyr Asp Leu Ser Pro Ile Asn Ser Ala Pro Ala Trp Leu
1               5                   10                  15

<210> SEQ ID NO 63
<211> LENGTH: 17
<212> TYPE: PRT
<213> ORGANISM: Sulfuricurvum kujiense

<400> SEQUENCE: 63

Ser His Asp Lys Asn Asp Asn Ser Pro Val Glu Gly Ala Pro Ala Lys
1               5                   10                  15

Leu

<210> SEQ ID NO 64
<211> LENGTH: 17
<212> TYPE: PRT
<213> ORGANISM: Nautilia profundicola

<400> SEQUENCE: 64

Ser His Val Val Gly Asn Leu Asn Pro Tyr His Ser Leu Pro Ser Leu
1               5                   10                  15

Leu

<210> SEQ ID NO 65
<211> LENGTH: 19
<212> TYPE: PRT
<213> ORGANISM: Sulfuvorum sp. NBC37-1

<400> SEQUENCE: 65

Leu His Ala Asp Asn Pro Arg Ile Pro Ala Leu Trp Glu Tyr Gly Val
1               5                   10                  15

Val Phe Phe

<210> SEQ ID NO 66
<211> LENGTH: 17
<212> TYPE: PRT
<213> ORGANISM: Wolinella succinogenes

<400> SEQUENCE: 66

Phe His Gln Glu Asn Asp Leu Ser Pro Leu His Thr Pro Leu Ser Leu
1               5                   10                  15

Leu

<210> SEQ ID NO 67
<211> LENGTH: 17
<212> TYPE: PRT
<213> ORGANISM: Caminibacter mediatlanticus

<400> SEQUENCE: 67

Ser His Val Ile Gly Asp Leu Asn Pro Ile His Ser Phe Pro Ser Ile
1               5                   10                  15

Leu

<210> SEQ ID NO 68
<211> LENGTH: 19
<212> TYPE: PRT
<213> ORGANISM: Nitratiruptor sp. SB155-2

<400> SEQUENCE: 68

Glu His Leu Asp Asn Pro Arg Leu Leu Asp Val Trp Arg Tyr Gly Thr
1               5                   10                  15

Ala Val Ile

<210> SEQ ID NO 69
<211> LENGTH: 17
<212> TYPE: PRT
<213> ORGANISM: Helicobacter pullorum

<400> SEQUENCE: 69

Gly Val Lys Ser Thr Phe Tyr Ser Pro Thr His Glu Ile Leu Ser Gln
1               5                   10                  15

Ile

<210> SEQ ID NO 70

```
<211> LENGTH: 17
<212> TYPE: PRT
<213> ORGANISM: Helicobacter canadensis

<400> SEQUENCE: 70

Gly Val Lys Ser Thr Leu His Ser Pro Ile Asn Glu Met Leu Ser Gln
1               5                   10                  15

Ile

<210> SEQ ID NO 71
<211> LENGTH: 17
<212> TYPE: PRT
<213> ORGANISM: Helicobacter winghamensis

<400> SEQUENCE: 71

Leu Asn Lys Ser Thr Leu Asn Ser Pro Thr His Glu Leu Leu Ser Leu
1               5                   10                  15

Ile

<210> SEQ ID NO 72
<211> LENGTH: 22
<212> TYPE: PRT
<213> ORGANISM: Desulfurobacterium thermolithotr.

<400> SEQUENCE: 72

Leu Arg Phe Val Pro Asp Asn Tyr Leu Thr Asn Asn Val Thr Tyr Pro
1               5                   10                  15

Ser Pro Ile Pro Met Glu
            20

<210> SEQ ID NO 73
<211> LENGTH: 6
<212> TYPE: PRT
<213> ORGANISM: Desulfomicrobium baculatum

<400> SEQUENCE: 73

Asp Pro Phe Thr Arg Ile
1               5

<210> SEQ ID NO 74
<211> LENGTH: 6
<212> TYPE: PRT
<213> ORGANISM: Desulfovibrio vulgaris

<400> SEQUENCE: 74

His Pro Met Ser Glu Leu
1               5

<210> SEQ ID NO 75
<211> LENGTH: 19
<212> TYPE: PRT
<213> ORGANISM: Desulfovibrio alkaliphilus

<400> SEQUENCE: 75

Thr Arg Gly Tyr Pro Asp Leu Pro Glu Tyr His Asp Pro Asn Leu Leu
1               5                   10                  15

Ala Trp Leu

<210> SEQ ID NO 76
<211> LENGTH: 6
<212> TYPE: PRT
<213> ORGANISM: Desulfohalobium retbaense
```

```
<400> SEQUENCE: 76

Arg Pro Met Ser Glu Leu
1               5

<210> SEQ ID NO 77
<211> LENGTH: 20
<212> TYPE: PRT
<213> ORGANISM: Deferribacter desulfuricans

<400> SEQUENCE: 77

Leu Arg Tyr Tyr Pro Asp Ser Gln Pro Lys Lys Arg Pro Val Pro Phe
1               5                   10                  15

Leu Ser Phe Leu
            20

<210> SEQ ID NO 78
<211> LENGTH: 5
<212> TYPE: PRT
<213> ORGANISM: Desulfovibrio salexigenes

<400> SEQUENCE: 78

Pro Met Ala Gly Leu
1               5

<210> SEQ ID NO 79
<211> LENGTH: 6
<212> TYPE: PRT
<213> ORGANISM: Desulfovibrio piger

<400> SEQUENCE: 79

His Pro Met Ala Val Met
1               5

<210> SEQ ID NO 80
<211> LENGTH: 6
<212> TYPE: PRT
<213> ORGANISM: Desulfovibrio aespoeensis

<400> SEQUENCE: 80

Tyr Ala Leu Ala Glu Phe
1               5

<210> SEQ ID NO 81
<211> LENGTH: 22
<212> TYPE: PRT
<213> ORGANISM: Cand. Puniceispirillum marinum

<400> SEQUENCE: 81

Asn Asn His Asp Tyr Gln Glu Asn Pro Asp Lys Arg Leu Thr Thr Glu
1               5                   10                  15

Gln Leu Leu Pro Ile Leu
            20

<210> SEQ ID NO 82
<211> LENGTH: 20
<212> TYPE: PRT
<213> ORGANISM: Calditerrivibrio nitroreducens

<400> SEQUENCE: 82

Leu Lys Ser Tyr Pro Asp His Asp Leu Phe Pro Ser Tyr Pro Ser Met
1               5                   10                  15

Leu Val Phe Leu
            20
```

```
<210> SEQ ID NO 83
<211> LENGTH: 22
<212> TYPE: PRT
<213> ORGANISM: Methanothermus fervidus

<400> SEQUENCE: 83

Trp Asp Ile Tyr Ser Tyr Tyr Pro Thr Gly Arg Ile Val Asp Tyr Pro
1               5                   10                  15

Pro Leu Leu Pro Trp Val
            20

<210> SEQ ID NO 84
<211> LENGTH: 22
<212> TYPE: PRT
<213> ORGANISM: Campylobacter jejuni

<400> SEQUENCE: 84

Leu Val Asp Gly Gly Lys His Leu Gly Lys Asp Asn Phe Phe Pro Ser
1               5                   10                  15

Phe Ala Leu Ser Lys Asp
            20

<210> SEQ ID NO 85
<211> LENGTH: 22
<212> TYPE: PRT
<213> ORGANISM: Campylobacter coli

<400> SEQUENCE: 85

Leu Ala Asp Gly Gly Lys His Leu Gly Lys Asp Asn Phe Phe Pro Ser
1               5                   10                  15

Phe Val Leu Ser Lys Asp
            20

<210> SEQ ID NO 86
<211> LENGTH: 22
<212> TYPE: PRT
<213> ORGANISM: Campylobacter lari

<400> SEQUENCE: 86

Leu Ile Asp Gly Gly Lys His Leu Gly Lys Asp Asn Phe Phe Ser Ser
1               5                   10                  15

Phe Val Leu Ser Lys Glu
            20

<210> SEQ ID NO 87
<211> LENGTH: 22
<212> TYPE: PRT
<213> ORGANISM: Campylobacter upsaliensis

<400> SEQUENCE: 87

Leu Ala Asp Gly Gly Lys His Leu Gly Lys Asp Asn Phe Phe Pro Ser
1               5                   10                  15

Phe Val Leu Ser Gln Asn
            20

<210> SEQ ID NO 88
<211> LENGTH: 22
<212> TYPE: PRT
<213> ORGANISM: Campylobacter curvus

<400> SEQUENCE: 88
```

Leu Ile Asp Gly Gly Lys His Leu Gly Arg Asp Asn Tyr Ala Val Ser
1               5                   10                  15

Tyr Ala Leu Gly Ser Asp
            20

<210> SEQ ID NO 89
<211> LENGTH: 22
<212> TYPE: PRT
<213> ORGANISM: Campylobacter concisus

<400> SEQUENCE: 89

Leu Ile Asp Gly Gly Lys His Leu Gly Arg Glu Asn Phe Ala Val Ser
1               5                   10                  15

Phe Ala Leu Gly Ser Asp
            20

<210> SEQ ID NO 90
<211> LENGTH: 22
<212> TYPE: PRT
<213> ORGANISM: Campylobacter hominis

<400> SEQUENCE: 90

Leu Ile Asp Gly Gly Lys His Leu Gly Asn Asp Asn Phe Pro Val Ser
1               5                   10                  15

Phe Ala Leu Phe Lys Asp
            20

<210> SEQ ID NO 91
<211> LENGTH: 22
<212> TYPE: PRT
<213> ORGANISM: Campylobacter gracilis

<400> SEQUENCE: 91

Leu Ile Asp Gly Gly Lys His Leu Gly Asn Asp Asn Phe Pro Val Ser
1               5                   10                  15

Phe Ala Leu Phe Arg Asp
            20

<210> SEQ ID NO 92
<211> LENGTH: 22
<212> TYPE: PRT
<213> ORGANISM: Campylobacter showae

<400> SEQUENCE: 92

Leu Ile Asp Gly Gly Lys His Leu Gly Arg Asp Asn Phe Ala Val Ser
1               5                   10                  15

Phe Ala Leu Ala Ser Asn
            20

<210> SEQ ID NO 93
<211> LENGTH: 23
<212> TYPE: PRT
<213> ORGANISM: Sulfurimonas autotrophica

<400> SEQUENCE: 93

Leu Ala Asp Gly Gly Lys His Asn Gly Ala Val Asn Phe Pro Val Ser
1               5                   10                  15

Tyr Met Leu Thr His Thr Gln
            20

<210> SEQ ID NO 94
<211> LENGTH: 23

```
<212> TYPE: PRT
<213> ORGANISM: Sulfurimonas denitrificans

<400> SEQUENCE: 94

Leu Ile Asp Gly Gly Lys His Arg Gly Asp Val Asn Phe Pro Val Ser
1               5                   10                  15

Phe Met Leu Thr Asn Pro Gln
            20

<210> SEQ ID NO 95
<211> LENGTH: 23
<212> TYPE: PRT
<213> ORGANISM: Sulfurospirillum deleyianum

<400> SEQUENCE: 95

Leu Ile Asp Gly Gly Lys His Ser Gly Glu Val Asn Phe Pro Val Ser
1               5                   10                  15

Phe Met Leu Ser Asn Pro Met
            20

<210> SEQ ID NO 96
<211> LENGTH: 23
<212> TYPE: PRT
<213> ORGANISM: Sulfuricurvum kujiense

<400> SEQUENCE: 96

Trp Ala Asp Gly Ala Gln His Ser Gly Gly Gln Asn Tyr Pro Ile Ser
1               5                   10                  15

Phe Val Leu Thr Ser Ser Asp
            20

<210> SEQ ID NO 97
<211> LENGTH: 22
<212> TYPE: PRT
<213> ORGANISM: Nautilia profundicola

<400> SEQUENCE: 97

Leu Val Asp Gly Gly Lys His Ser Gly Glu Val Asn Phe Pro Val Ser
1               5                   10                  15

Phe Ala Leu Thr His Asn
            20

<210> SEQ ID NO 98
<211> LENGTH: 22
<212> TYPE: PRT
<213> ORGANISM: Sulfuvorum sp. NBC37-1

<400> SEQUENCE: 98

Leu Ile Asp Gly Gly Lys His Asn Asn Asp Asn Phe Ile Ile Ser Lys
1               5                   10                  15

Ile Met Gln Thr Ser Ser
            20

<210> SEQ ID NO 99
<211> LENGTH: 23
<212> TYPE: PRT
<213> ORGANISM: Wolinella succinogenes

<400> SEQUENCE: 99

Leu Ile Asp Gly Ala Lys His Ala Gly Asn Ile Asn Tyr Pro Val Ser
1               5                   10                  15

Tyr Ala Leu Leu Ser Gln Asn
```

<210> SEQ ID NO 100
<211> LENGTH: 22
<212> TYPE: PRT
<213> ORGANISM: Caminibacter mediatlanticus

<400> SEQUENCE: 100

Leu Ile Asp Gly Gly Lys His Ser Gly Ala Asp Asn Phe Pro Val Ser
1               5                   10                  15

Phe Ile Leu Thr His Asn
            20

<210> SEQ ID NO 101
<211> LENGTH: 22
<212> TYPE: PRT
<213> ORGANISM: Nitratiruptor sp. SB155-2

<400> SEQUENCE: 101

Leu Ile Asp Gly Gly Lys His Asn Glu Asp Asn Phe Leu Val Ser Lys
1               5                   10                  15

Ile Leu Thr Thr Ser Asp
            20

<210> SEQ ID NO 102
<211> LENGTH: 23
<212> TYPE: PRT
<213> ORGANISM: Helicobacter pullorum

<400> SEQUENCE: 102

Phe Val Asp Gly Gly Ile His Ser Gly Lys Gln Asn Tyr Pro Ile Ser
1               5                   10                  15

Phe Val Leu Ser Ala Lys Asn
            20

<210> SEQ ID NO 103
<211> LENGTH: 23
<212> TYPE: PRT
<213> ORGANISM: Helicobacter canadensis

<400> SEQUENCE: 103

Phe Ile Asp Gly Gly Lys His Ser Gly Arg Asp Asn Phe Pro Ile Ser
1               5                   10                  15

Phe Ile Leu Ser Ser Thr Asn
            20

<210> SEQ ID NO 104
<211> LENGTH: 22
<212> TYPE: PRT
<213> ORGANISM: Helicobacter winghamensis

<400> SEQUENCE: 104

Phe Ile Asp Gly Gly Lys His Leu Glu Ser Lys Ala Ile Ser Gln Phe
1               5                   10                  15

Phe Ile Ser Ser Asp Thr
            20

<210> SEQ ID NO 105
<211> LENGTH: 23
<212> TYPE: PRT
<213> ORGANISM: Desulfurobacterium thermolithotr.

<400> SEQUENCE: 105

-continued

Phe His Asp Gly Gln Ser Gln Gly Ser Pro Lys Thr Tyr Phe Val Ala
1               5                   10                  15

Thr Ser Phe Ser Thr Ser Asn
            20

<210> SEQ ID NO 106
<211> LENGTH: 23
<212> TYPE: PRT
<213> ORGANISM: Desulfomicrobium baculatum

<400> SEQUENCE: 106

Phe Gly Asp Gly Ser Arg Gln Ser Gly Pro Trp Leu Tyr Pro Leu Ala
1               5                   10                  15

Arg Val His Cys Ala Ser Ser
            20

<210> SEQ ID NO 107
<211> LENGTH: 23
<212> TYPE: PRT
<213> ORGANISM: Desulfovibrio vulgaris

<400> SEQUENCE: 107

Ile Ala Asp Gly Ala Ser His Gly Gly Pro Ser Leu Tyr Val Pro Ala
1               5                   10                  15

Ala Val Phe Ser Thr Ala Asn
            20

<210> SEQ ID NO 108
<211> LENGTH: 23
<212> TYPE: PRT
<213> ORGANISM: Desulfovibrio alkaliphilus

<400> SEQUENCE: 108

Tyr His Asp Gly Ser Leu His Gly Gly Leu Arg Ser Ala Leu Ile Ala
1               5                   10                  15

Lys Ala Leu Thr Ser Ser Ser
            20

<210> SEQ ID NO 109
<211> LENGTH: 23
<212> TYPE: PRT
<213> ORGANISM: Desulfohalobium retbaense

<400> SEQUENCE: 109

Phe Gly Asp Gly Gly Ala His Ser Gly Pro His Leu Tyr Pro Leu Ala
1               5                   10                  15

Lys Ile His Ser Thr Asn Ser
            20

<210> SEQ ID NO 110
<211> LENGTH: 23
<212> TYPE: PRT
<213> ORGANISM: Deferribacter desulfuricans

<400> SEQUENCE: 110

Tyr His Asp Gly Gly Ser Gln Gly Ser Pro Lys Thr Tyr Phe Ile Ala
1               5                   10                  15

Lys Ser Leu Ile Thr Asp Lys
            20

<210> SEQ ID NO 111

-continued

```
<211> LENGTH: 23
<212> TYPE: PRT
<213> ORGANISM: Desulfovibrio salexigenes

<400> SEQUENCE: 111

Phe Ala Asp Gly Ser Asn His Gly Gly Thr Thr Leu Phe Pro Leu Ala
1               5                   10                  15

Phe Ala Tyr Thr Thr Pro Ser
            20

<210> SEQ ID NO 112
<211> LENGTH: 23
<212> TYPE: PRT
<213> ORGANISM: Desulfovibrio piger

<400> SEQUENCE: 112

Ile Ala Asp Gly Ala Arg Asn Ala Gly Ala Pro Leu Tyr Leu Ser Ala
1               5                   10                  15

Ala Val Leu Gly Thr Asp Asn
            20

<210> SEQ ID NO 113
<211> LENGTH: 23
<212> TYPE: PRT
<213> ORGANISM: Desulfovibrio aespoeensis

<400> SEQUENCE: 113

Val Ala Asp Gly Gly Lys His Ala Gly Arg Asp Val Tyr Pro Ile Ala
1               5                   10                  15

Phe Ala Met Thr Thr Pro Ser
            20

<210> SEQ ID NO 114
<211> LENGTH: 23
<212> TYPE: PRT
<213> ORGANISM: Cand. Puniceispirillum marinum

<400> SEQUENCE: 114

Leu His Asp Gly Gly Thr Gln Thr Ser Pro Val Thr His Tyr Val Ala
1               5                   10                  15

Arg Ala Leu Ile Ala Asp Ser
            20

<210> SEQ ID NO 115
<211> LENGTH: 23
<212> TYPE: PRT
<213> ORGANISM: Calditerrivibrio nitroreducens

<400> SEQUENCE: 115

Tyr His Asp Gly Gly Val His Gly Ala Asp Arg Ser Tyr Phe Thr Ala
1               5                   10                  15

Lys Ala Phe Val Glu Thr Asp
            20

<210> SEQ ID NO 116
<211> LENGTH: 23
<212> TYPE: PRT
```

```
<213> ORGANISM: Methanothermus fervidus

<400> SEQUENCE: 116

Leu Val Asp Gly Gly Ser Gln Asn Thr Pro Arg Met Tyr Trp Ile Cys
1               5                   10                  15

Lys Ala Tyr Ala Thr Asp Asn
            20
```

COMPOSITIONS AND METHODS FOR PROTEIN GLYCOSYLATION

CROSS-REFERENCE TO RELATED APPLICATIONS

This Application is a Continuation of U.S. patent application Ser. No. 15/540,690 (now U.S. Pat. No. 10,150,952), filed Jun. 29, 2017, which claims priority to U.S. National Stage application submitted under 35 U.S.C. § 371 for International Application No. PCT/EP2015/081229, filed Dec. 24, 2015, which claims priority to provisional Application No. 62/097,975, filed Dec. 30, 2014 and 62/098,071, filed Dec. 30, 2014, all of which are incorporated herein by reference in their entireties.

INCORPORATION-BY-REFERENCE OF SEQUENCE LISTING OR TABLE

The content of the sequence listing submitted electronically via EFS-WEB in International Application No. PCT/EP2015/081229, filed Dec. 24, 2015, is incorporated herein by reference in its entirety.

1. INTRODUCTION

Described herein are oligosaccharyl transferases for use in N-glycosylating proteins of interest in vitro and in host cells. Methods for using such oligosaccharyl transferases, nucleic acids encoding such oligosaccharyl transferases, and host cells comprising such oligosaccharyl transferases are also provided herein. Glycoconjugates generated by using such oligosaccharyl transferases are also provided herein.

2. BACKGROUND

Glycoconjugate vaccines are widely recognized for their ability to prevent many life-threatening bacterial infections. Glycoconjugate vaccines are generally considered efficacious and safe and have been used in humans for over 30 years. Conventional glycovaccine production often involves the chemical modification of immunogenic carrier proteins with polysaccharide antigens of pathogenic bacteria. However, more recently, biotechnological processes for producing glycoconjugate vaccines have emerged that are expected to reduce production costs and to further increase the homogeneity and possibly the potency and safety of glycoconjugate vaccine preparations.

In eukaryotic cells, N-linked glycosylation is a key post-translational protein modification mechanism involving several enzymes. In prokaryotic cells N-linked glycosylation is catalyzed by certain bacterial N-oligosaccharyltransferases (N-OSTs). The protein glycosylation gene cluster of *Campylobacter jejuni* (*C. jejuni*) includes the pglB gene, which encodes a membrane-bound N-OST (PglB$_{Cj}$). PglB$_{Cj}$ can be expressed in standard bacterial hosts, such as *Escherichia coli* (*E. coli*), and can glycosylate co-expressed periplasmic proteins that carry at least one surface-exposed D/E-Y-N-X-S/T (Y, X≠P) glycosylation motif. PglB$_{Cj}$ can transfer bacterial polysaccharide antigens to *C. jejuni* proteins as well as to immunogenic carrier proteins of other organisms containing engineered glycosylation sites. PglB$_{Cj}$ can transfer *C. jejuni* oligosaccharides and, to a certain degree, O-antigen lipopolysaccharide structures of Gram-negative bacteria and capsular antigen polysaccharides of Gram-positive bacteria.

The present disclosure provides recombinant N-OSTs with modified substrate specificities and methods of using the recombinant N-OSTs for glycoconjugate vaccine production. Such recombinant N-OSTs can advantageously be used in N-glycosylation of proteins.

3. SUMMARY

In one aspect, provided herein is a recombinant N-oligosaccharyl transferase, wherein the recombinant N-oligosaccharyl transferase can delectably link an oligosaccharide or polysaccharide lacking an N-acetyl sugar at the reducing end to a carrier protein at an N-glycosylation consensus sequence.

In some embodiments, the N-OST activity of linking the oligosaccharide or polysaccharide lacking the N-acetyl sugar at the reducing end to the carrier protein at the N-glycosylation sequence is detected by ELISA.

In some embodiments, the ELISA signal indicating the N-OST activity is detectable if it is >2σ or >3σ above the ELISA background signal.

In some embodiments, the carrier protein is a natural carrier protein from the same organism as the N-OST. In some embodiments, the carrier protein is a heterologous carrier protein from a different organism than the N-OST.

In some embodiments, the carrier protein is selected from the group consisting of exotoxin A of *P. aeruginosa* (EPA), CRM197, diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins.

In some embodiments, the carrier protein has at least one glycosylation motif. In some embodiments, the at least one glycosylation motif comprises D/E-Y-N-X-S/T (X, Y≠P). In some embodiments, the at least one glycosylation motif comprises Asn-X-Ser(Thr), wherein X can be any amino acid except Pro. In some embodiments, the oligosaccharide or polysaccharide lacking the N-acetyl sugar at the reducing end comprises an antigen.

In some embodiments, the antigen includes an *E. coli* antigen, a *Salmonella* sp antigen, a *Pseudomonas* sp. antigen, a *Klebsiella* sp. antigen, a *acinetobacter* O antigen, a *Chlamydia trachomatis* antigen, a *Vibrio cholera* antigen, a *Listeria* sp. antigen, a *Legionella pneumophila* serotypes 1 to 15 antigen, a *Bordetella parapertussis* antigen, a *Burkholderia mallei* or *pseudomallei* antigen, a *Francisella tularensis* antigen, a *Campylobacter* sp. antigen; a *Clostridium difficile* antigen, *Streptococcus pyrogenes* antigen, a *Streptococcus agalacticae* antigen, a *Neisseria meningitidis* antigen, a *Candida albicans* antigen, a *Haemophilus* influenza antigen, a *Enterococcus faecalis* antigen, a *Borrelia burgdorferi* antigen, a *Neisseria meningitidis* antigen, a *Haemophilus influenza* antigen, a *Leishmania major* antigen, or a *Shigella sonnei*, or *Streptococcus pneumoniae* antigen (e.g., CP1, CP4, and the like).

In some embodiments, the oligosaccharide or polysaccharide lacking the N-acetyl sugar at the reducing end is a *Staphylococcus aureus* or a *Salmonella enterica* sv. polysaccharide. In some embodiments, the oligosaccharide or polysaccharide lacking the N-acetyl sugar at the reducing end is a *Staphylococcus aureus* CP5 or a *Salmonella enterica* sv. *Typhimurium* LT2 polysaccharide.

In some embodiments, the recombinant N-oligsaccharyl transferase can increase the yield of in vivo glycosylation or in vitro glycosylation of the carrier protein with the polysaccharide lacking the N-acetyl sugar at the reducing end to produce glycosylated carrier protein at a level of more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold above background level in an assay detecting the glycosylated carrier protein.

In some embodiments, the recombinant N-oligsaccharyl transferase can increase the rate of in vivo glycosylation or in vitro glycosylation of the carrier protein with the polysaccharide lacking the N-acetyl sugar at the reducing end by more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold compared to a wild-type form of the recombinant N-oligosaccharyl transferase.

In some embodiments, the recombinant N-oligosaccharyl transferase can in vivo or in vitro glycosylate at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% of the carrier protein with the polysaccharide lacking the N-acetyl sugar at the reducing end.

In some embodiments, the recombinant N-oligosaccharyl transferase comprises a modification in one or more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of the recombinant N-oligosaccharyl transferase and the N-glycosylated carrier protein.

In some embodiments, the 2.5-4.0 Å distance is the distance from the first terminal monosaccharide unit at the reducing end of the oligosaccharide or polysaccharide component. In some embodiments, the 2.5-4.0 Å distance is from the second terminal monosaccharide unit at the reducing end of the oligosaccharide or polysaccharide component. In some embodiments, the 2.5-4.0 Å distance is from the third terminal monosaccharide unit at the reducing end of the oligosaccharide or polysaccharide component; In some embodiments, the 2.5-4.0 Å distance is from a conserved amino acid in the catalytic center of the recombinant N-oligosaccharyl transferase in the structural model of a complex of the recombinant N-oligosaccharyl transferase and the N-glycosylated carrier protein (e.g., K522, N311, H 479, G476, Y462, G477, Y77, S80, or S199 of PglBCj, see, e.g., FIG. 2A-2C).

In some embodiments, the modification in die one or more amino acids is an amino acid substitution.

In some embodiments, the one or more amino acids include an amino acid that is a non-conserved amino acid in a phylogenetic family of N-oligosaccharyl transferases. In some embodiments, the non-conserved amino acid is conserved in less than 90%, less than 80%, less than 70%, less than 60%, less than 50%, less than 40%, less than 30%, less than 20% or less than 10% of members of the phylogenetic family of N-oligosaccharyl transferases.

In some embodiments, the recombinant N-oligosaccharyl transferase comprises a modification in two or more amino acids. In some embodiments, the recombinant N-oligosaccharyl transferase comprises modification in three or more amino acids. In some embodiments, the recombinant N-oligosaccharyl transferase comprises modification in four or more amino acids.

In some embodiments, at least one of the one or more amino acids is located in a periplasmatic loop of a transmembrane domain of the recombinant N-oligosaccharyl transferase. In some embodiments, the periplasmatic loop of the transmembrane domain is a large external loop 5 (EL5). In some embodiments, the recombinant N-oligosaccharyl transferase is $PglB_{Cj}$ and the EL5 is EL5 of $PglB_{Cj}$.

In some embodiments, the recombinant N-oligosaccharyl transferase further comprises a mutation in one or more amino acids in a QLKFYxxR motif. In some embodiments, the Q287LKFYxxR294 motif is a Q287LKFYxxR294 motif. In some embodiments, the Q287LKFYxxR294 motif is the Q287LKFYxxR294 motif of $PglB_{Cj}$.

In some embodiments, the recombinant N-oligosaccharyl transferase is a recombinant $PglB_{Cj}$.

In some embodiments, the bound N-glycosylated carrier protein is a natural C. jejuni glycosylated carrier protein. In some embodiments, the bound N-glycosylated carrier protein is a heterologous C. jejuni glycosylated carrier protein.

In some embodiments, the oligosaccharide or polysaccharide component of the bound N-glycosylated carrier protein has a galactose monosaccharide at its reducing end.

In some embodiments, one or more amino acids selected from the group consisting of Y77, S80, S196, N311, Y462, H479, K522, G476 and G477 of $PglB_{Cj}$ are modified. In some embodiments, N311 of $PglB_{Cj}$ is modified. In some embodiments, the recombinant $PglB_{Cj}$ comprises a substitution N311V or a substitution N311I. In some embodiments, the recombinant $PglB_{Cj}$ comprises a substitution N311V. In some embodiments, the recombinant $PglB_{Cj}$ further comprises a modification in one or more amino acids selected from the group consisting of Y77 and S80. In some embodiments, the recombinant $PglB_{Cj}$ comprises an amino acid substitution selected from the group consisting of Y77H, Y77T, Y77W, Y77R, Y77K, Y77A, Y77G, S80R and S80H. In some embodiments, the recombinant $PglB_{Cj}$ comprises an amino acid substitution selected from the group consisting of Y77H and S80R.

In some embodiments, the recombinant $PglB_{Cj}$ further comprises an amino acid modification in one or more amino acids of the Q287LKFYxxR294 motif of $PglB_{Cj}$. In some embodiments, the recombinant $PglB_{Cj}$ comprises an amino acid modification in one or more amino acids selected from the group consisting of Q287, L288 and K289. In some embodiments, the recombinant $PglB_{Cj}$ comprises one or more amino acid substitutions selected from the group consisting of Q287P, Q287K, Q287R, L288M, L288F, L288I, L288C, K289R, K289N, K289Q and R294K.

In some embodiments, the recombinant $PglB_{Cj}$ comprises an amino acid substitution N311V. In some embodiments, the recombinant $PglB_{Cj}$ comprises amino acid substitutions Y77H and N311V. In some embodiments, the recombinant $PglB_{Cj}$ comprises amino acid substitutions S80R and N311V. In some embodiments, the recombinant $PglB_{Cj}$ comprises amino acid substitutions Q287P and Y77H or a Q287P and S80R. In some embodiments, the recombinant PglB$_{Cj}$ comprises amino acid substitutions S80R, Q287P and N311V. In some embodiments, the recombinant PglB$_{Cj}$ comprises amino acid substitutions Y77H, Q287P and N311V. In some embodiments, the recombinant PglB$_{Cj}$ comprises amino acid substitutions Y77H, S80R, Q287P and N311V. In some embodiments, the recombinant PglB$_{Cj}$ comprises amino acid substitutions Y77H, S80R, Q287P, K289R and N311V. In some embodiments, the recombinant PglB$_{Cj}$ comprises amino acid substitutions N311V and A699V. In some embodiments, the recombinant PglB$_{Cj}$ comprises amino acid substitutions K482R and D483H.

In another aspect, provided herein is a recombinant N-oligosaccharyl transferase (N-OST) comprising a modification in one or more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of the recombinant N-oligosaccharyl transferase and the N-glycosylated carrier protein. In some embodiments, the modification is an amino acid substitution.

In some embodiments, the carrier protein is selected from the group consisting of exotoxin A of *P. aeruginosa* (EPA), CRM197, diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins.

In some embodiments, the oligosaccharide or polysaccharide lacking the N-acetyl sugar at the reducing end comprises an antigen. In some embodiments, the antigen includes an *E. coli* antigen, a *Salmonella* sp antigen, a *Pseudomonas* sp. antigen, a *Klebsiella* sp. antigen, an *acinetobacter* O antigen, a *Chlamydia trachomatis* antigen, a *Vibrio cholera* antigen, a *Listeria* sp. antigen, a *Legionella pneumophila* serotypes 1 to 15 antigen, a *Bordetella parapertussis* antigen, a *Burkholderia mallei* or *pseudomallei* antigen, a *Francisella tularensis* antigen, a *Campylobacter* sp. antigen; a *Clostridium difficile* antigen, a *Streptococcus agalacticae* antigen, a *Neisseria meningitidis* antigen, a *Candida albicans* antigen, a *Haemophilus influenza* antigen, a *Enterococcus faecalis* antigen, a *Borrelia burgdorferi* antigen, a *Neisseria meningitidis* antigen, a, *Haemophilus influenza* antigen, a *Leishmania major* antigen, a *Shigella sonnei*, or a *Streptococcus pneumoniae* antigen (e.g., CP1, CP4, and the like).

In some embodiments, the recombinant N-oligosaccharyl transferase comprises modifications in two or more amino acids. In some embodiments, the recombinant N-oligosaccharyl transferase comprises modifications in three or more amino acids. In some embodiments, the recombinant N-oligosaccharyl transferase comprises modifications in four or more amino acids.

In some embodiments, at least one of the one or more amino acids is located in a periplasmatic loop of a transmembrane domain of the recombinant N-oligosaccharyl transferase. In some embodiments, the periplasmatic loop of the transmembrane domain is a large external loop 5 (EL5). In some embodiments, the recombinant N-oligosaccharyl transferase is PglB of *Campylobacter jejuni* (PglB$_{Cj}$) and EL5 is EL5 of PglB$_{Cj}$.

In some embodiments, the recombinant N-oligosaccharyl transferase further comprises a modification in one or more amino acids in a QLKFYxxR motif. In some embodiments, wherein the recombinant N-oligosaccharyl transferase further comprises a modification in one or more amino acids in a Q287LKFYxxR294 motif. In some embodiments, the QLKFYxxR motif is the Q287LKFYxxR294 motif of PglB$_{Cj}$.

In some embodiments, the amino acid substitution is a substitution of a non-conserved amino acid in a phylogenetic family of N-oligosaccharyl transferases.

In some embodiments, the bound N-glycosylated polypeptide product is a natural N-glycosylated carrier protein from the same organism as the recombinant N-oligosaccharyl transferase. In some embodiments, the N-glycosylated carrier protein is a heterologous N-glycosylated carrier protein, wherein the oligosaccharide or polysaccharide component of the N-glycosylated carrier protein is from a different organism than the recombinant N-oligosaccharyl transferase and/or the carrier protein component of the N-glycosylated carrier protein is from a different organism than the recombinant N-oligosaccharyl transferase.

In some embodiments, the recombinant N-oligosaccharyl transferase is recombinant PglB$_{Cj}$.

In some embodiments, the bound N-glycosylated polypeptide product is a natural *C. jejuni* glycosylated carrier protein. In some embodiments, the bound N-glycosylated polypeptide product is a heterologous *C. jejuni* glycosylated carrier protein. In some embodiments the heterologous *C. jejuni* glycosylated carrier protein is *Pseudomonas aeruginosa* exotoxin (EPA)-*S. dysenteriae* O1 (EPA-O1), EPA-& *aureus* capsular polysaccharide Type 5 (EPA-CP5) or EPA-*Salmonella enterica* (*S. enterica*) LT2 (EPA-LT2).

In some embodiments, the oligosaccharide or polysaccharide component of the bound N-glycosylated carrier protein does not have an N-acetyl monosaccharide at its reducing end. In some embodiments, the oligosaccharide or polysaccharide component of the bound N-glycosylated carrier protein has a galactose monosaccharide at its reducing end.

In some embodiments, one or more amino acids from the group consisting of Y77, S80, S196, N311, Y462, H479, K522, G476 and G477 of PglB$_{Cj}$ are modified. In some embodiments, of PglB$_{Cj}$ is modified. In some embodiments, the recombinant PglB$_{Cj}$ comprises an amino acid substitution selected from the group consisting of N311V and N311I. In some embodiments, the recombinant PglB$_{Cj}$ comprises an amino acid substitution N311V. In some embodiments, one or more amino acids selected from the group consisting of Y77 and S80 of PglB$_{Cj}$ or modified. In some embodiments, the recombinant PglB$_{Cj}$ comprises an amino acid substitution selected from the group consisting of Y77H, Y77T, Y77W, Y77R, Y77K, Y77A, Y77G, S80R and S80H. In some embodiments, the recombinant PglB$_{Cj}$ comprises an amino acid substitutions selected from the group consisting of Y77H and S80R.

In some embodiments, the recombinant PglB$_{Cj}$ further comprises a modification of one or more amino acids of the Q287LKFYxxR294 motif of PglB$_{Cj}$. In some embodiments, the recombinant PglB$_{Cj}$ comprises a modification of one more amino acids selected from the group consisting of Q287, L288 and K289. In some embodiments, the recombinant PglB$_{Cj}$ comprises a substitution selected from the group consisting of Q287P, Q287K, Q287R, L288M, L288F, L288I, L288C, K289R, K289N, K289Q and R294K.

In some embodiments, the recombinant PglB$_{Cj}$ comprises a substitution N311V. In some embodiments, the recombinant PglB$_{Cj}$ comprises a substitution Y77H and a substitution N311V. In some embodiments, the recombinant PglB$_{Cj}$ comprises a substitution S80R and a substitution N311V. In some embodiments, the recombinant PglB$_{Cj}$ comprises a substitution Q287P mid a substitution Y77H or a substitution Q287P mutation and a substitution S80R. In some embodiments, the recombinant PglB$_{Cj}$ comprises a substitution S80R, a substitution Q287P and a substitution N311V. In some embodiments, the recombinant PglB$_{Cj}$ comprises a substitution Y77H, a substitution Q287P and a substitution N311V. In some embodiments, the recombinant PglB$_{Cj}$ comprises a substitution Y77H, a substitution S80R, a substitution Q287P and a substitution N311V. In some embodiments, the recombinant PglB$_{Cj}$ comprises a substitution Y77H, a substitution S80R, a substitution Q287P, a substitution K289R and a substitution N311V. In some embodiments, the recombinant PglB$_{Cj}$ comprises a substitution N311V and a substitution A699V. In some embodiments, the recombinant PglB$_{Cj}$ comprises a substitution K482R, and a substitution D483H.

In some embodiments, the recombinant N-oligosaccharyl transferase can detectably link an oligosaccharide or polysaccharide lacking an N-acetyl sugar at the reducing end to a carrier protein.

In some embodiments, the recombinant N-oligosaccharyl transferase can detectably link an oligosaccharide or polysaccharide having a galactose monosaccharide at the reducing end to a carrier protein.

In some embodiments, the oligosaccharide or polysaccharide is a *Staphylococcus aureus* or a *Salmonella enterica* sv. oligosaccharide or polysaccharide. In some embodiments, the oligosaccharide or polysaccharide is a *Staphylococcus aureus* CP5 or a *Salmonella enterica* sv. *Typhimurium* LT2 oligosaccharide or polysaccharide.

In some embodiments, the recombinant N-oligsaccaryl transferase can increase the yield of in vivo glycosylation or in vitro glycosylation of the carrier protein with the oligosaccharide or polysaccharide lacking the N-acetyl sugar at the reducing end to produce glycosylated carrier protein at a level of more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold above background level in an assay detecting the glycosylated carrier protein.

In some embodiments, the recombinant N-oligsaccharyl transferase can increase the in vivo or in vitro rate of glycosylation of a carrier protein with the oligosaccharide or polysaccharide lacking the N-acetyl sugar at the reducing end by more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold compared to a wild-type form of the recombinant N-oligosaccharyl transferase.

In some embodiments, the recombinant N-oligosaccharyl transferase can yield an in vivo glycosylation level or an in vitro glycosylation level of the carrier protein of at least 1%, at least 3%, at least 5%, at least 10%, at least 15%, at least 20%, at least 25%, at least 30%, at least 35%, at least 40%, at least 45%, at least 50%, at least 55%, at least 60%, or at least 70%.

In another aspect, provided herein is a recombinant N-oligosaccharyl transferase PglB$_{Cj}$ comprising a N311V substitution.

In another aspect, provided herein is a recombinant N-oligosaccharyl transferase PglB$_{Cj}$ comprising a N311V mutation and a Y77H substitution.

In another aspect, provided herein is a recombinant N-oligosaccharyl transferase PglB$_{Cj}$ comprising a N311V mutation and a S80R substitution.

In another aspect, provided herein is a recombinant N-oligosaccharyl transferase PglB$_{Cj}$ comprising a N311V mutation and a Y77H mutation and a S80R substitution.

In another aspect, provided herein is a recombinant N-oligosaccharyl transferase PglB$_{Cj}$ comprising a N311V mutation and a Q287P substitution.

In another aspect, provided herein is a recombinant N-oligosaccharyl transferase PglB$_{Cj}$ comprising a N311V mutation, a Y77H substitution and a Q287P substitution.

In another aspect, provided herein is a recombinant N-oligosaccharyl transferase PglB$_{Cj}$ comprising a N311V mutation, S80R substitution and a Q287P substitution.

In another aspect, provided herein is a recombinant N-oligosaccharyl transferase PglB$_{Cj}$ comprising a N311V substitution, a Y77H substitution, a S80R substitution and a Q287P substitution.

In another aspect, provided herein is a recombinant N-oligosaccharyl transferase PglB$_{Cj}$ comprising a N311V substitution and a A669V substitution.

In another aspect, provided herein is a recombinant N-oligosaccharyl transferase PglB$_{Cj}$ comprising a N311V substitution, a Y771I substitution, a S80R substitution, a Q287P substitution and a K289R substitution.

In another aspect, provided herein is a recombinant N-oligosaccharyl transferase PglB$_{Cj}$ comprising a K482R substitution and a D483H substitution.

In another aspect, provided herein is a recombinant N-oligosaccharyl transferase PglB$_{Cj}$ comprising a N311V substitution and a A669V substitution.

In another aspect, provided herein is a recombinant N-oligosaccharyl transferase PglB$_{Cj}$ (PglB *C. lari*) comprising a N314V substitution.

In another aspect, provided herein is a recombinant N-oligosaccharyl transferase PglB$_{Cj}$ comprising a N314V mutation and a Y79H substitution.

In another aspect, provided herein is a recombinant N-oligosaccharyl transferase PglB$_{Cj}$ comprising a N314V mutation and a S82R substitution.

In another aspect, provided herein is a recombinant N-oligosaccharyl transferase PglB$_{Cj}$ comprising a N314V mutation and a Y79H mutation and a S82R substitution.

In another aspect, provided herein is a recombinant N-oligosaccharyl transferase PglB$_{Cj}$ comprising a N314V mutation and a Q289P substitution.

In another aspect, provided herein is a recombinant N-oligosaccharyl transferase PglB$_{Cj}$ comprising a N314V mutation, a Y79H substitution and a Q289P substitution.

In another aspect, provided herein is a recombinant N-oligosaccharyl transferase PglB$_{Cj}$ comprising a N314V mutation, S82R substitution and a Q289P substitution.

In another aspect, provided herein is a recombinant N-oligosaccharyl transferase PglB$_{Cj}$ comprising a N314V substitution, a Y79H substitution, a S82R substitution and a Q289P substitution.

In another aspect, provided herein is a recombinant N-oligosaccharyl transferase PglB$_{Cj}$ comprising a K488R substitution and a D489H substitution.

In another aspect, provided herein is a nucleic acid encoding a recombinant N-oligosaccharyl transferase described herein.

In another aspect, provided herein is a host cell comprising a recombinant N-oligosaccharyl transferase described herein.

In some embodiments, the host cell further comprises a recombinant glycosyltransferase.

In another aspect, provided herein is a host cell comprising a nucleic acid described herein.

In some embodiments, the host cell is a prokaryotic cell. In some embodiments, the host cell is an E. coli cell.

In another aspect, provided herein is a method of producing a bioconjugate comprising culturing a host cell described herein.

In some embodiments, the host cell comprises a carrier protein and a recombinant N-oligosaccharyl transferase. In some embodiments, the host cell further comprises a recombinant glycosyltransferase. In some embodiments, the recombinant N-oligosaccharyl transferase is a recombinant PglB$_{Cj}$.

In some embodiments, the carrier protein is selected from the group consisting of exotoxin A of P. aeruginosa (EPA), CRM197, diphtheria toxoid, tetanus toxoid, detoxified hemolysin A of S. aureus, clumping factor A, clumping factor B, E. coli FimH, E. coli FimHC, E. coli heat labile enterotoxin, detoxified variants of E. coli heat labile enterotoxin, Cholera toxin B subunit (CTB), cholera toxin, detoxified variants of cholera toxin, E. coli sat protein, the passenger domain of E. coli sat protein, C. jejuni AcrA, and C. jejuni natural glycoproteins.

In some embodiments, the bioconjugate is an N-glycosylated carrier protein. In some embodiments, the bioconjugate is a natural C. jejuni N-glycosylated carrier protein. In some embodiments, the bioconjugate is a heterologous C. jejuni A-glycosylated carrier protein. In some embodiments, the N-glycosylated carrier protein does not have an N-acetyl sugar at the reducing end of its oligosaccharide or polysaccharide component. In some embodiments, the N-glycosylated carrier protein has a galactose at the reducing end of its oligosaccharide or polysaccharide component.

In some embodiments, the recombinant N-oligosaccharyl transferase mutant can increase the rate of bioconjugate production by more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more titan 50-fold, mote than 60-fold, more than 70-fold, more than 80-fold, more than 90-fold or more than 100-fold compared to the rate achieved with a wild-type form of the recombinant N-oligosaccharyl transferase.

In some embodiments, the recombinant N-oligsaccharyl transferase mutant can increase the yield of bioconjugate production to a level of more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold the above background level in an assay detecting the bioconjugate.

In some embodiments, at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% of carrier protein in a host cell is glycosylated to form the bioconjugate.

In some embodiments, the method further comprises purifying the bioconjugate from the host cell culture.

In another aspect, provided herein is a method of screening a library of recombinant N-oligosaccharyl transferases each recombinant N-oligosaccharyl transferase comprising a modification in one or more amino acids, comprising contacting each member of the library of recombinant N-oligosaccharyl transferases with a carrier protein and an oligosaccharide or polysaccharide lacking an N-acetyl sugar at its reducing end to produce a bioconjugate.

In some embodiments, the bioconjugate is an N-glycosylated carrier protein.

In some embodiments, the contacting occurs in vitro. In some embodiments, the contacting occurs in vivo. In some embodiments, the contacting occurs in a host cell. In some embodiments, the host cell is a prokaryotic cell. In some embodiments, the host cell is an E. coli cell.

In some embodiments, the library of recombinant N-oligosaccharyl transferases comprises at least 2, at least 5, at least 10, at least 15, at least 20, at least 25, at least 50, at least 75, at least 100, at least 150, at least 200, at least 250, at least 500, at least 750 or at least 1,000 recombinant N-oligosaccharyl transferases.

In some embodiments, the library of recombinant N-oligosaccharide transferases comprises one or more recombinant N-oligosaccharide transferases described herein.

In some embodiments, the method further comprises analyzing the rate or yield of production of the bioconjugate.

In some embodiments, the method further comprises selecting one or more recombinant N-oligosaccharyl transferases from the library of recombinant N-oligosaccharyl transferases.

In some embodiments, the one or more recombinant N-oligosaccharyl transferase is selected if the recombinant N-oligosaccharyl transferase yields the bioconjugate at a rate that is more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold faster than the rate of a wild-type form of the recombinant N-oligosaccharyl transferase.

In some embodiments, the one or more N-oligosaccharyl transferase mutant is selected if the N-oligosaccharyl transferase mutant yields the bioconjugate at a yield that is detectable at a level of more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold above background level in an assay detecting the bioconjugate.

In some embodiments, the one or more recombinant N-oligosaccharyl transferase is selected if the recombinant N-oligosaccharyl transferase glycosylates at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% of a carrier protein in the host cell.

In another aspect, provided herein is a method of identifying a recombinant N-oligosaccharyl transferase having a modified substrate selectivity relative to a wild-type form of the N-oligosaccharyl transferase, comprising modifying one or more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of the recombinant N-oligosaccharyl transferase and the N-glycosylated carrier protein.

In some embodiments, the method comprises modifying two or more amino acids of the recombinant N-oligosaccharyl transferase. In some embodiments, the method comprises modifying three or more amino acids of the recombinant N-oligosaccharyl transferase. In some embodiments, the method comprises modifying four or more amino acids of the recombinant N-oligosaccharyl transferase.

In some embodiments, at least one of the one or more amino acids is located in a periplasmatic loop of a transmembrane domain of the recombinant N-oligosaccharyl transferase. In some embodiments, the periplasmatic loop of the transmembrane domain is a large external loop 5 (EL5).

In some embodiments, the method further comprises mutating one or more amino acids in a QLKFYxxR motif of the recombinant N-oligosaccharyl transferase. In some embodiments, the QLKFYxxR motif is a Q287LKFYxxR294 motif. In some embodiments, the bound N-glycosylated carrier protein is a natural N-glycosylated carrier protein.

In some embodiments, the bound N-glycosylated carrier protein is a heterologous N-glycosylated carrier protein. In some embodiments, the recombinant N-oligosaccharyl transferase is a recombinant $PglB_{Cj}$. In some embodiments, the bound N-glycosylated carrier protein is a natural C. jejuni N-glycosylated carrier protein. In some embodiments, the bound N-glycosylated carrier protein is a heterologous C. jejuni N-glycosylated carrier protein.

In some embodiments, the oligosaccharide or polysaccharide component of the bound N-glycosylated carrier protein does not have an N-acetyl monosaccharide at its reducing end. In some embodiments, the oligosaccharide or polysaccharide component of the bound N-glycosylated carrier protein has a galactose monosaccharide at its reducing end.

In some embodiments, the recombinant N-oligosaccharyl transferase has a modified substrate selectivity in vitro. In some embodiments, the recombinant N-oligosaccharyl transferase has a modified substrate selectivity in vivo.

4. BRIEF DESCRIPTION OF THE DRAWINGS

FIG. 1. depicts structures of the natural C. jejuni heptasaccharide substrate of $PglB_{Cj}$ and of two non-natural polysaccharide substrates with decreasing glycosylation efficiency from top to bottom. GalNAc: 2-N-acetylgalactosamine, Glc: glucose, DATDH: 2,4-diacetamido-2,4,6-trideoxyhexose, P-P-und; undecaprenyl-pyrophosphate carrier, Rha: rhamnose, Gal: galactose, GlcNAc: N-acetylglucosamine, ManNAc: N-acetylmannosamine, OAc: O-acetyl modification, FucNAc: N-acetylfucosamine, Man: mannose, Abe: abequose (3,6-deoxy-D-galactose).

Figure 2A:
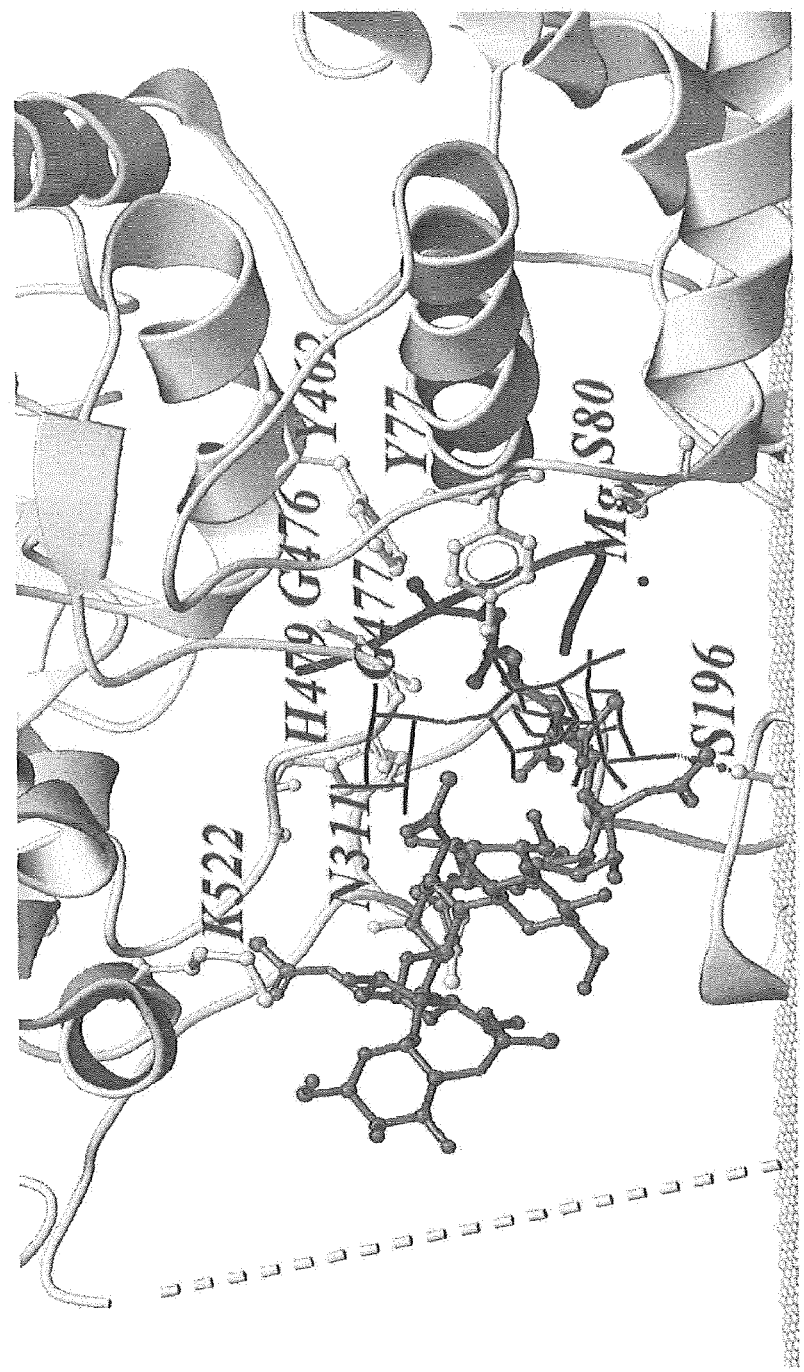
Figure 2B:
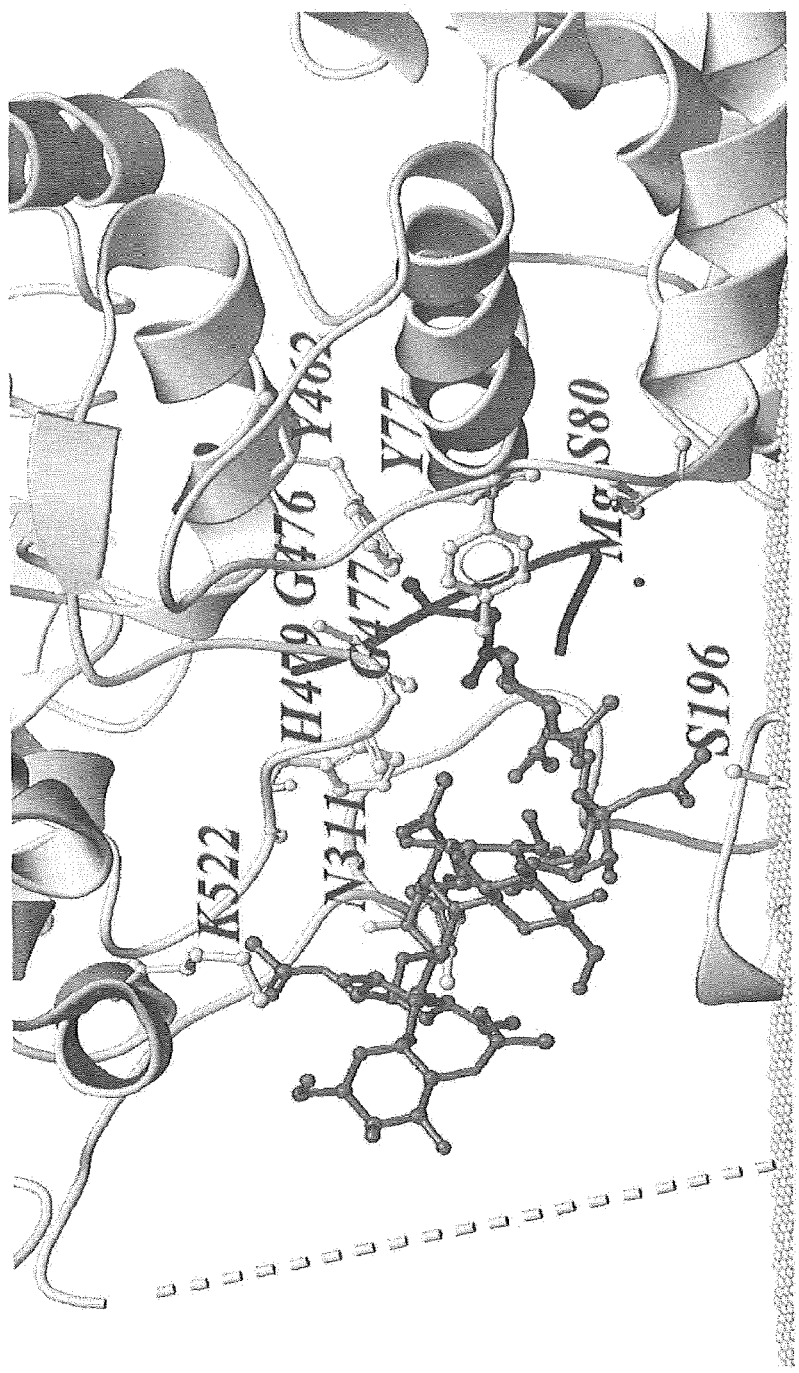
Figure 2C:
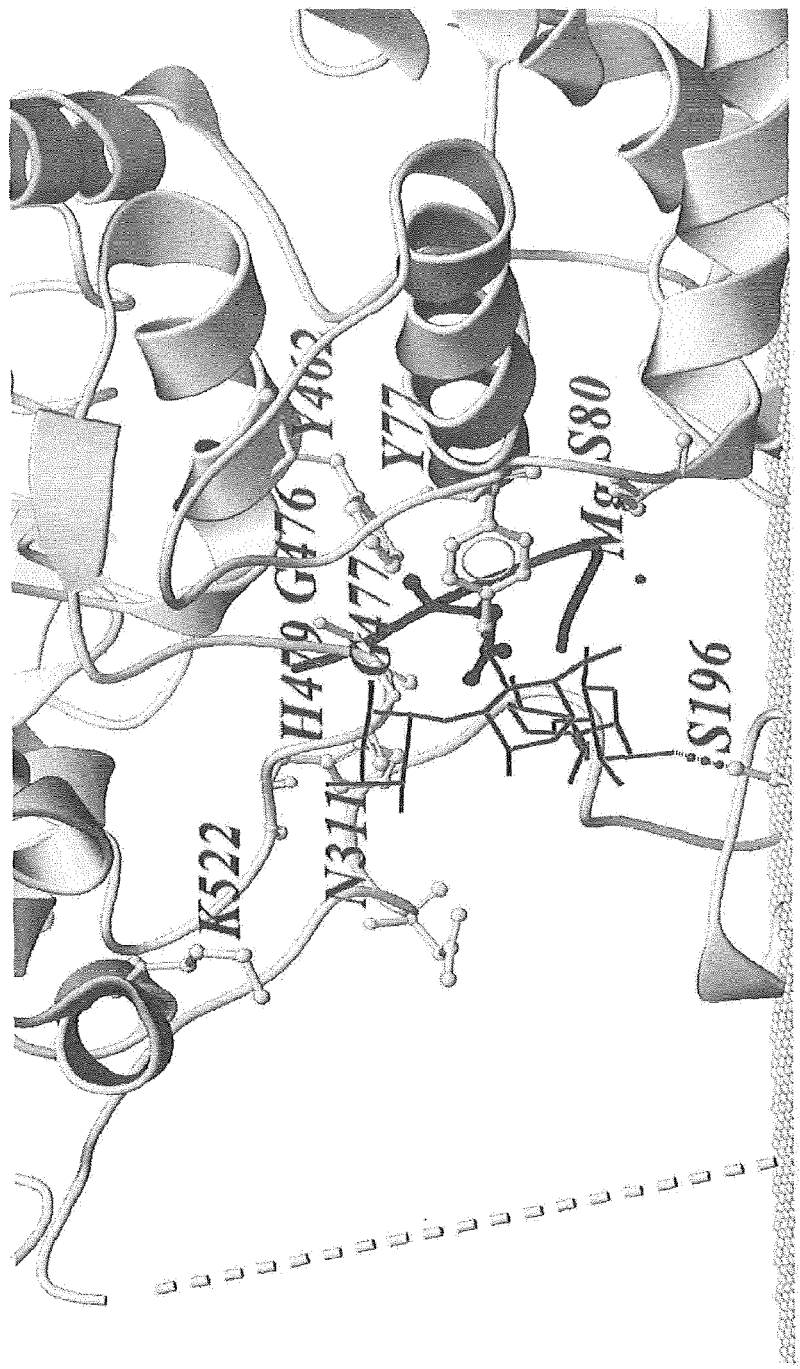

FIG. 2A-2C depicts an exemplary modeling of oligosaccharide structures when interacting with PglBCj. FIG. 2A depicts an exemplary conformation of C. jejuni OS (light grey ball-and-stick representation) and S. enteria a LT2 repeating unit (dark grey stick representation) in the active site, the position of the linkage to the acceptor peptide was chosen as fix point during dynamic modeling. FIG. 2B depicts an exemplary conformation of C. jejuni OS (light grey ball-and-stick representation). FIG. 2C depicts an exemplary conformation of S. enterica LT2 repeating unit (dark grey stick representation). The PglBCj backbone structure is shown in grey (ribbon) and the phosphate groups of the membrane as light grey balls. Residues in close proximity to the natural OS are depicted as light grey ball-stick representations. A broken line illustrates the connectivity of die unstructured external loop EL5.

FIGS. 3A and 3B illustrates results of an exemplary DWP-ELISA screening of a saturation mutagenesis library randomizing PglBCj residue N311. FIG. 3A depicts screening results using host strain and detection antibodies for S. aureus CP5 polysaccharides. FIG. 3B depicts screening results using host strain and detection antibodies for S. enterica LT2 polysaccharides. Open circles indicate library clones; filled triangles indicate positive control clones expressing wild-type PglB (pGVXN1413), shaded triangles indicate negative control clones expressing inactive PglB-mut (pGVXN408). Sequenced clones are marked by an ellipsoid.

Figure 4A:
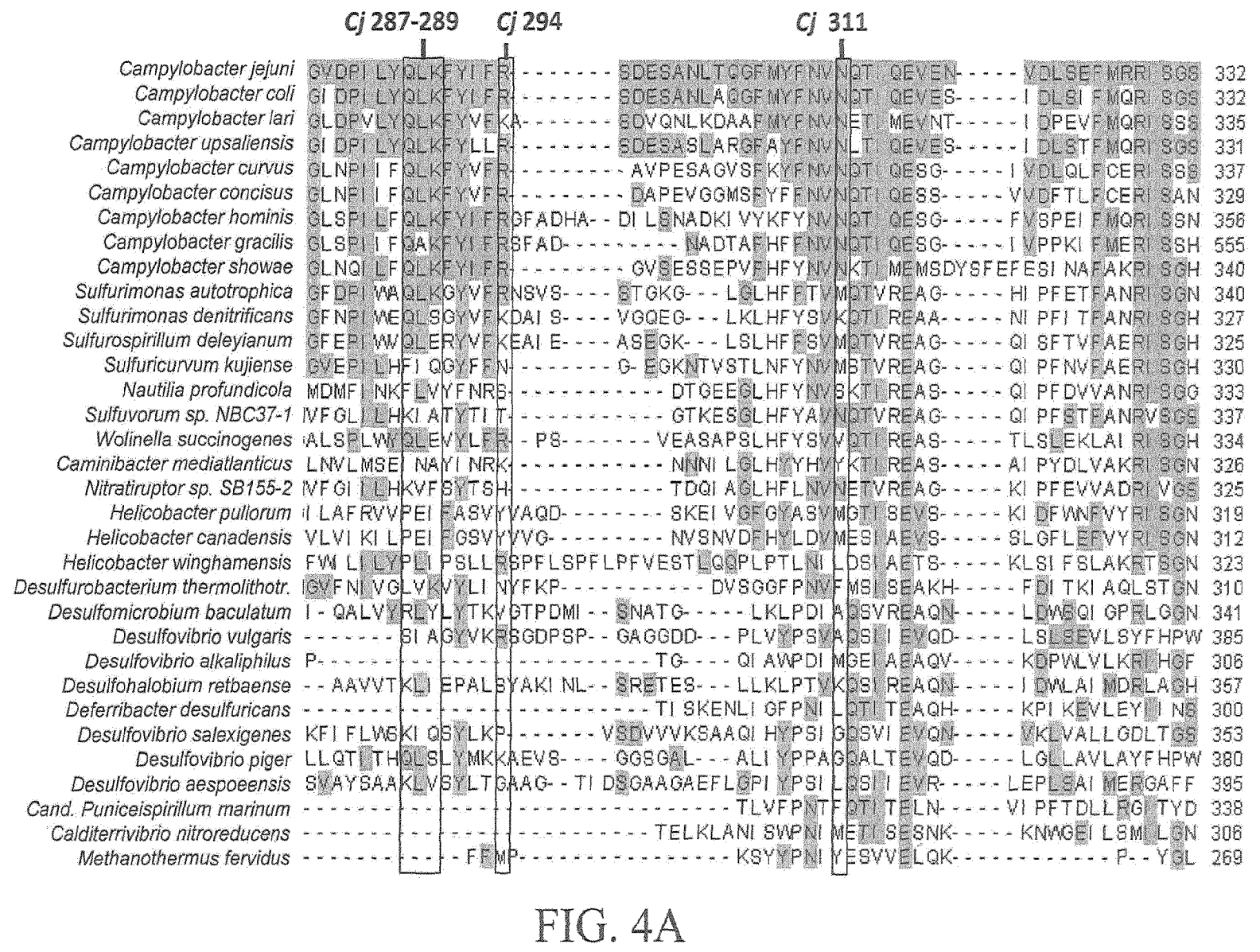
Figure 4B:
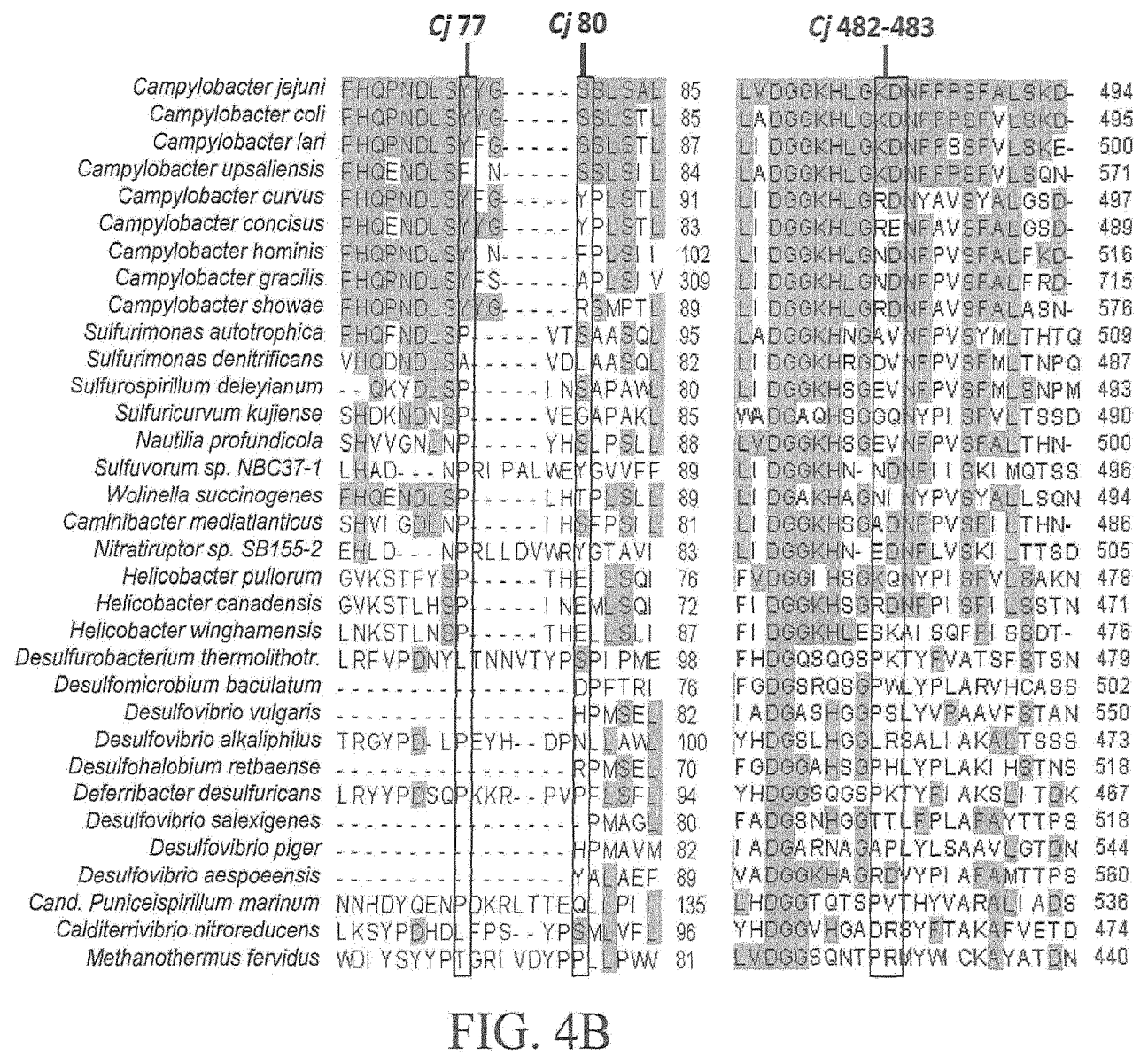

FIG. 4 depicts alignments of bacterial PglB homologues (A) in the EL5 region (SEQ ID NOs: 18 to 50), including the C. jejuni 287QLKFYxxR294 motif and C. jejuni N311, and (B) in the vicinity of residues C. jejuni Y77/S80 (SEQ ID Nos: 51 to 83) and C. jejuni K482/D843 (SEQ ID NOs: 84 to 116). PglB of C. jejuni was used as search template for Protein BLAST and non-redundant sequences were aligned with the MegAlign™. program using the ClustalW algorithm (DNASTAR, Madison, Wis., USA). $PglB_{Cj}$ residues conserved in sequences of other species are shaded. Relevant C. jejuni residues are indicated at the top and corresponding amino acids in homologous N-OST sequences are boxed. The aligned sequences are summarized in Table 1.

TABLE 1

| Organism | EL5 Region | Cj 77/80 Region | Cj 482-483 region |
|---|---|---|---|
| Campylobacter jejuni | SEQ ID NO: 18 | SEQ ID NO: 51 | SEQ ID NO: 84 |
| Campylobacter coil | SEQ ID NO: 19 | SEQ ID NO: 52 | SEQ ID NO: 85 |
| Campylobacter lari | SEQ ID NO: 20 | SEQ ID NO: 53 | SEQ ID NO: 86 |
| Campylobacter upsaliensis | SEQ ID NO: 21 | SEQ ID NO: 54 | SEQ ID NO: 87 |
| Campylobacter curvus | SEQ ID NO: 22 | SEQ ID NO: 55 | SEQ ID NO: 88 |
| Campylobacter concisus | SEQ ID NO: 23 | SEQ ID NO: 56 | SEQ ID NO: 89 |

TABLE 1-continued

| Organism | EL5 Region | Cj 77/80 Region | Cj 482-483 region |
|---|---|---|---|
| Campylobacter hominis | SEQ ID NO: 24 | SEQ ID NO: 57 | SEQ ID NO: 90 |
| Campylobacter gracilis | SEQ ID NO: 25 | SEQ ID NO: 58 | SEQ ID NO: 91 |
| Campylobacter showae | SEQ ID NO: 26 | SEQ ID NO: 59 | SEQ ID NO: 92 |
| Sulfurimonas autotrophica | SEQ ID NO: 27 | SEQ ID NO: 60 | SEQ ID NO: 93 |
| Sulfurimonas denitrificans | SEQ ID NO: 28 | SEQ ID NO: 61 | SEQ ID NO: 94 |
| Sulfurospirillum deleyianum | SEQ ID NO: 29 | SEQ ID NO: 62 | SEQ ID NO: 95 |
| Sulfuricurvum kujiense | SEQ ID NO: 30 | SEQ ID NO: 63 | SEQ ID NO: 96 |
| Nautilia profundicola | SEQ ID NO: 31 | SEQ ID NO: 64 | SEQ ID NO: 97 |
| Sulfuvorum sp. NBC37-1 | SEQ ID NO: 32 | SEQ ID NO: 65 | SEQ ID NO: 98 |
| Wolinella succinogenes | SEQ ID NO: 33 | SEQ ID NO: 66 | SEQ ID NO: 99 |
| Caminibacter mediatlanticus | SEQ ID NO: 34 | SEQ ID NO: 67 | SEQ ID NO: 100 |
| Nitratiruptor sp. SB155-2 | SEQ ID NO: 35 | SEQ ID NO: 68 | SEQ ID NO: 101 |
| Helicobacter pullorum | SEQ ID NO: 36 | SEQ ID NO: 69 | SEQ ID NO: 102 |
| Helicobacter canadensis | SEQ ID NO: 37 | SEQ ID NO: 70 | SEQ ID NO: 103 |
| Helicobacter winghamensis | SEQ ID NO. 38 | SEQ ID NO: 71 | SEQ ID NO: 104 |
| Desulfurobacterium thermolithotr. | SEQ ID NO: 39 | SEQ ID NO: 72 | SEQ ID NO: 105 |
| Desulfomicrobium baculatum | SEQ ID NO: 40 | SEQ ID NO: 73 | SEQ ID NO: 106 |
| Desulfovibrio vulgaris | SEQ ID NO: 41 | SEQ ID NO: 74 | SEQ ID NO: 107 |
| Desulfovibrio alkaliphilus | SEQ ID NO: 42 | SEQ ID NO: 75 | SEQ ID NO: 108 |
| Desulfohalobium retbaense | SEQ ID NO: 43 | SEQ ID NO: 76 | SEQ ID NO: 109 |
| Deferribacter desulfuricans | SEQ ID NO: 44 | SEQ ID NO: 77 | SEQ ID NO: 110 |
| Desulfovibrio salexigenes | SEQ ID NO: 45 | SEQ ID NO: 78 | SEQ ID NO: 111 |
| Desulfovibrio piger | SEQ ID NO: 46 | SEQ ID NO: 79 | SEQ ID NO: 112 |
| Desulfovibrio aespoeensis | SEQ ID NO: 47 | SEQ ID NO: 80 | SEQ ID NO: 113 |
| Cand. Puniceispirillum marinum | SEQ ID NO: 48 | SEQ ID NO: 81 | SEQ ID NO: 114 |
| Calditerrivibrio nitroreducens | SEQ ID NO: 49 | SEQ ID NO: 82 | SEQ ID NO: 115 |
| Methanothermus fervidus | SEQ ID NO: 50 | SEQ ID NO: 83 | SEQ ID NO: 116 |

Figure 5:
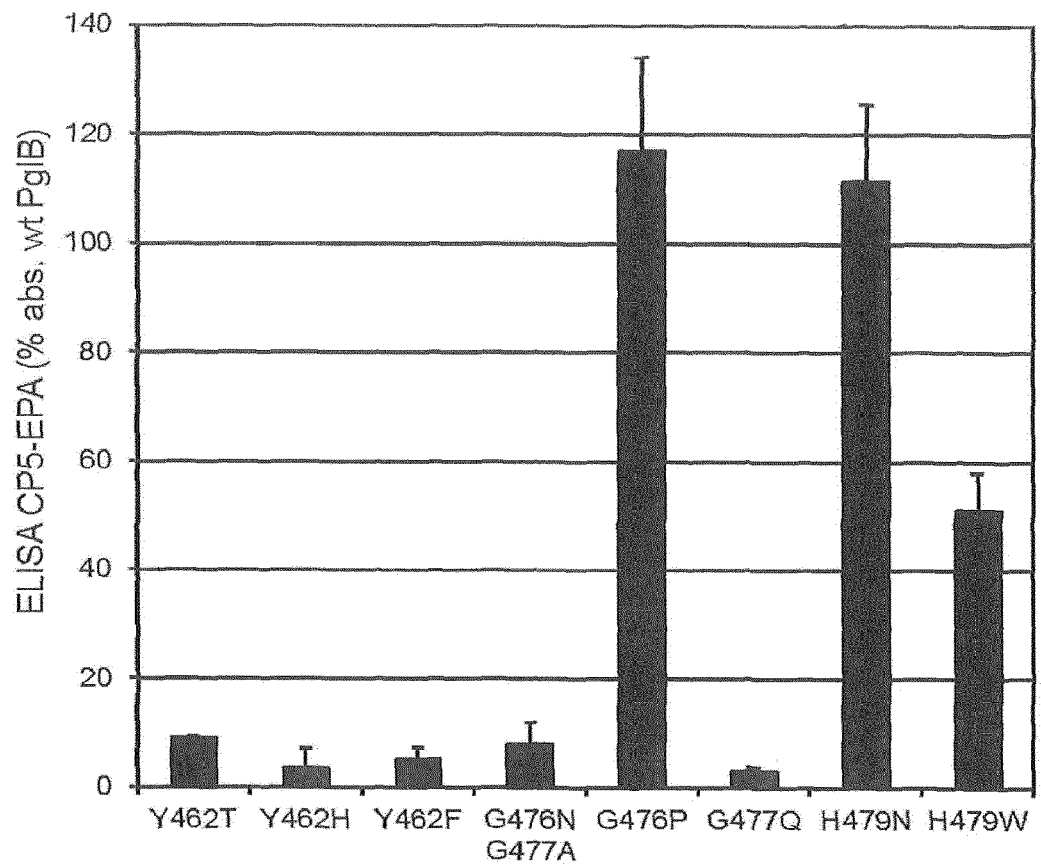

FIG. 5 depicts a graph illustrating the effect of amino acid substitutions within potential sugar-interacting PglB$_{Cj}$ residues Y462, G476, G477 and H479 on in vivo CP5-EPA production in overnight induced DWP cultures. Reference wells (100% values, background corrected): pGVXN1050 (wild-type template plasmid). Average numbers and standard deviations of triplicate clones per variant are depicted.

FIG. 6A-6D illustrates the effect of PglB variant N311V on glycoprotein formation in shake flask analyzed by Western blot. FIG. 6A illustrates results obtained with LT2-EPA in host strain S. enterica SGSC228 (pGVXN150). FIG. 6B illustrates results obtained with CP5-EPA in host strain E. coli St1717 (pGVXN150, pGVXN393). FIG. 6C illustrates results obtained with O1-EPA in host strain E. coli CLM24 (pGVXN64, pGVXN150). FIG. 6D illustrates results obtained with EPA-C. jejuni OS in host strain E. coli CLM24 (pACYC(pglmut), pGVXN150). Same experiments as shown in FIG. 5, biomass-normalized periplasmic extracts, similar loading volumes, samples of one shake flask culture per variant. Wild-type PglB: pGVXN970, PglB N311V: pGVXN1217. Theoretical molecular mass of unglycosylated EPA-6H: 69.4 kDa.

Figure 7A:
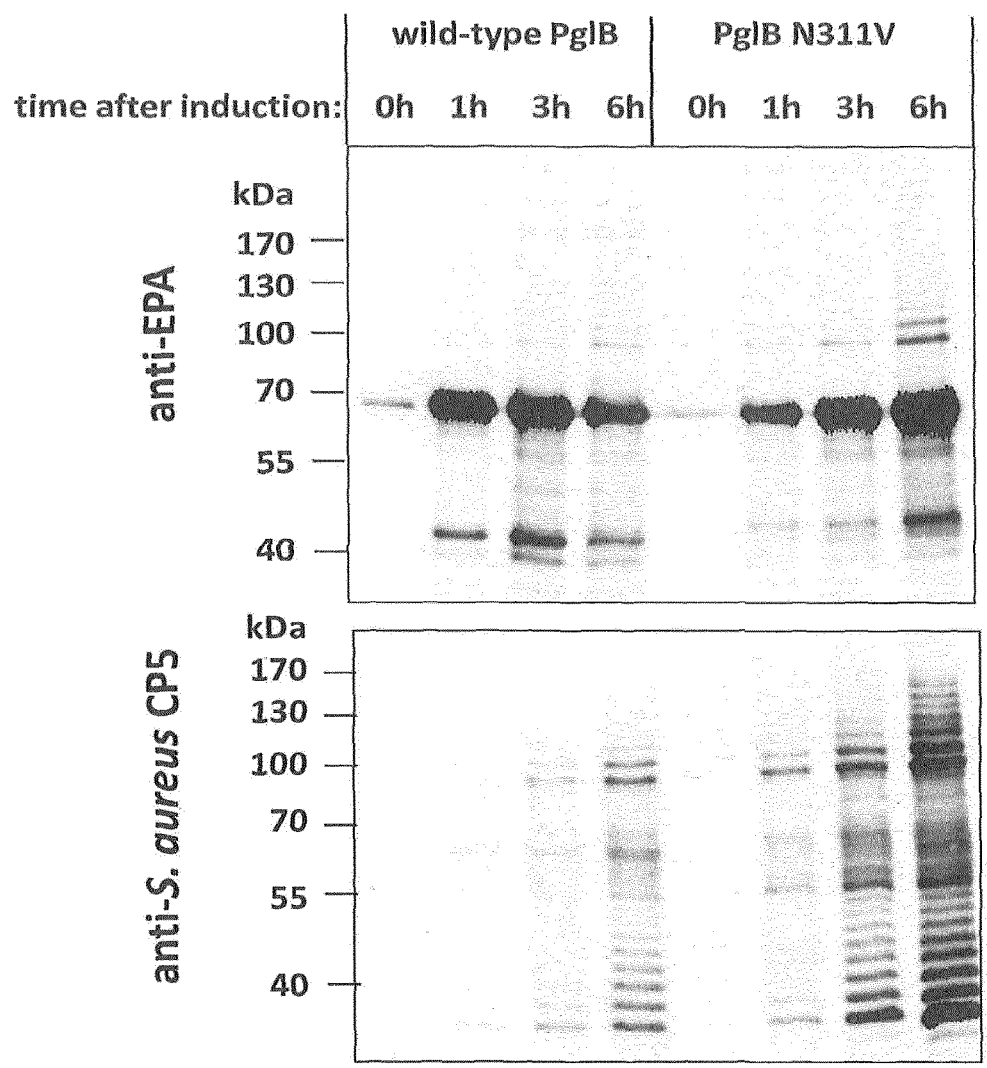
Figure 7B:
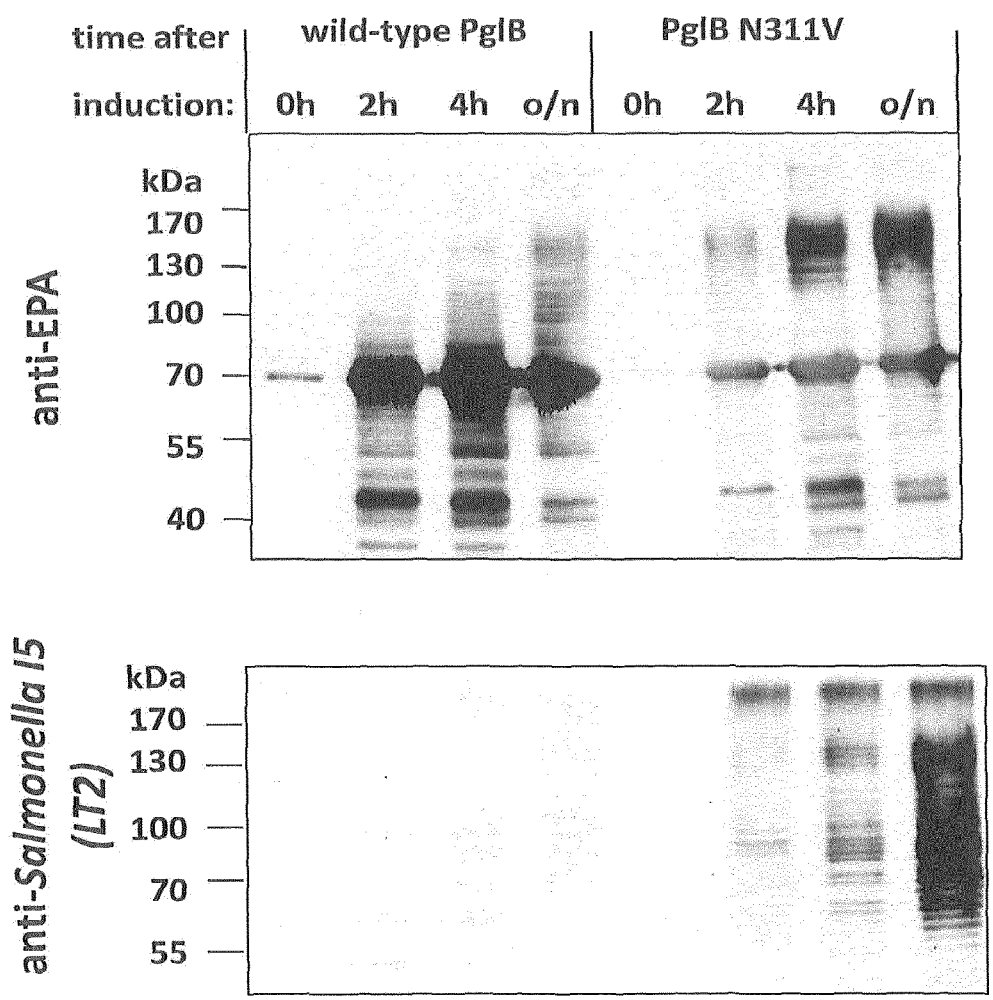
Figure 7C:
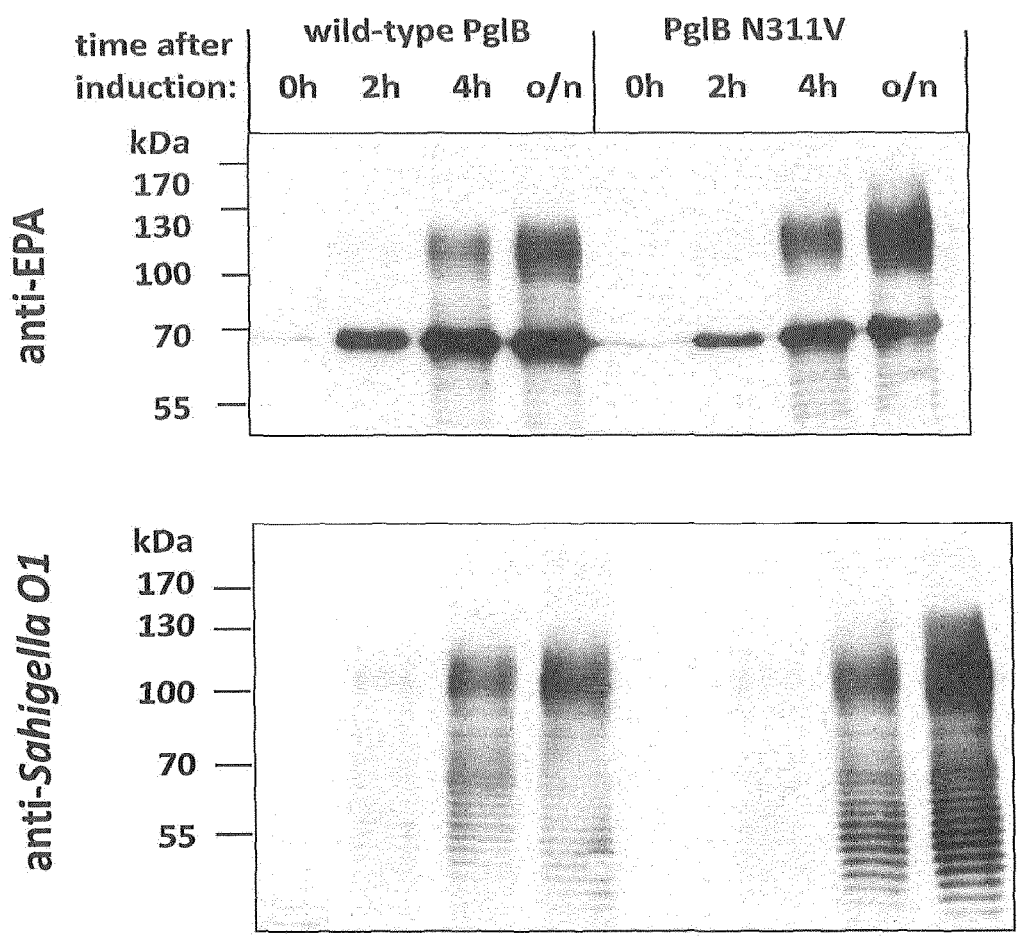
Figure 7D:
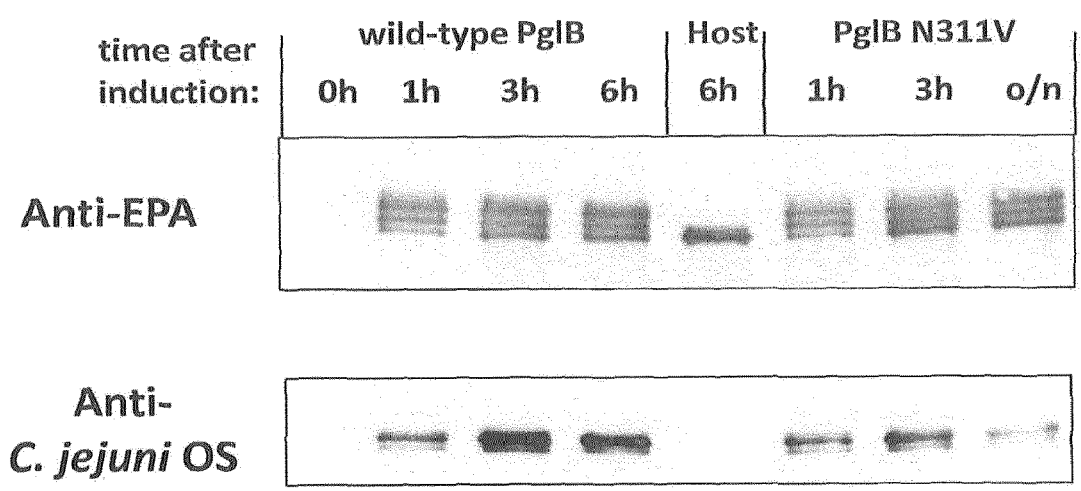

FIG. 7A-7D illustrates the effect of amino acid substitution PglBCj N311V on glycosylation of EPA with three heterologous polysaccharides and natural oligosaccharides. Open symbols: wild-type PglB (pGVXN970), closed symbols; PglB N311V (pGVXN1217). FIG. 7A illustrates exemplary results obtained with the host strain and detection antibodies for S. aureus CP5 polysaccharides. FIG. 7B illustrates exemplary results obtained with the host strain and detection antibodies for S. enterica sv. Thyphimurium LT2 polysaccharides. FIG. 7C illustrates results obtained with the host strain and detection antibodies for S. dysenteriae O1 polysaccharides. FIG. 7D illustrates results obtained with the host strain and detection antibodies for C. jejuni oligosaccharides. Background-corrected ELISA signals for biomass-normalized periplasmic extracts from shake flask cultures, average values and standard deviations of n=3 biological replicates are depicted.

Figure 8B:
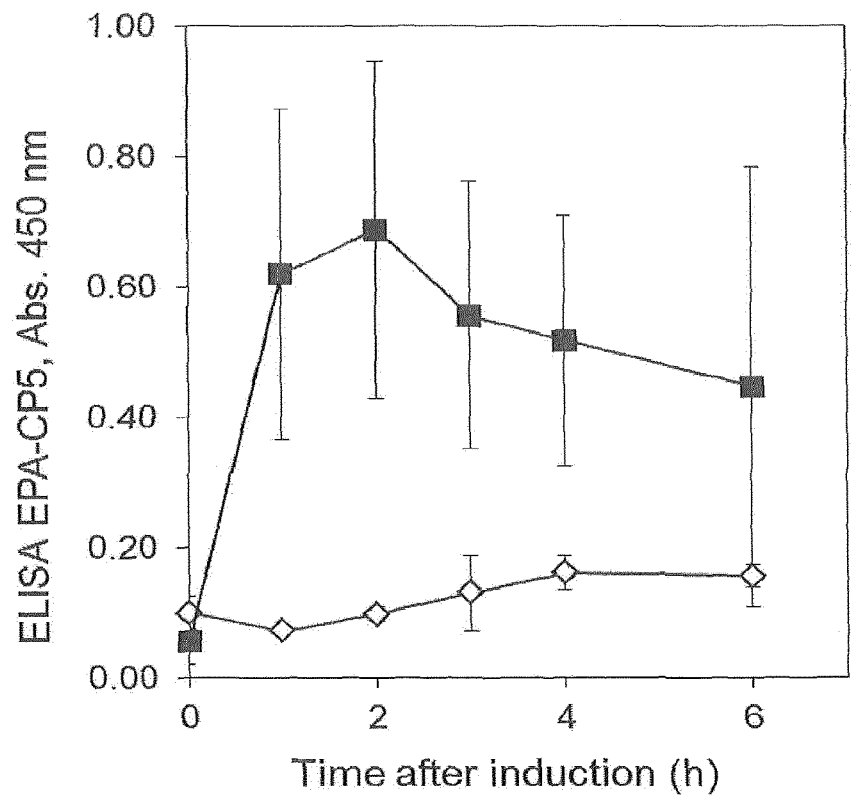

FIGS. 8A and 8B illustrates the effect of N311V on expression of HA-tagged PglB and CP5-EPA formation in a shake flask experiment. FIG. 8A illustrates results of an anti-HA Western blot analysis of PglB-HA in an E. coli St1717 (pGVXN150, pGVXN393) host strain. FIG. 8B illustrates results of a time course of CP5-EPA formation analyzed by sandwich ELISA of biomass normalized periplasmic extracts. Open symbols depict results for wild-type PglB-HA. Closed symbols depict results for PglB-HA N311V. Average values and standard deviations for n=3 replicate cultures are shown.

Figure 9C:
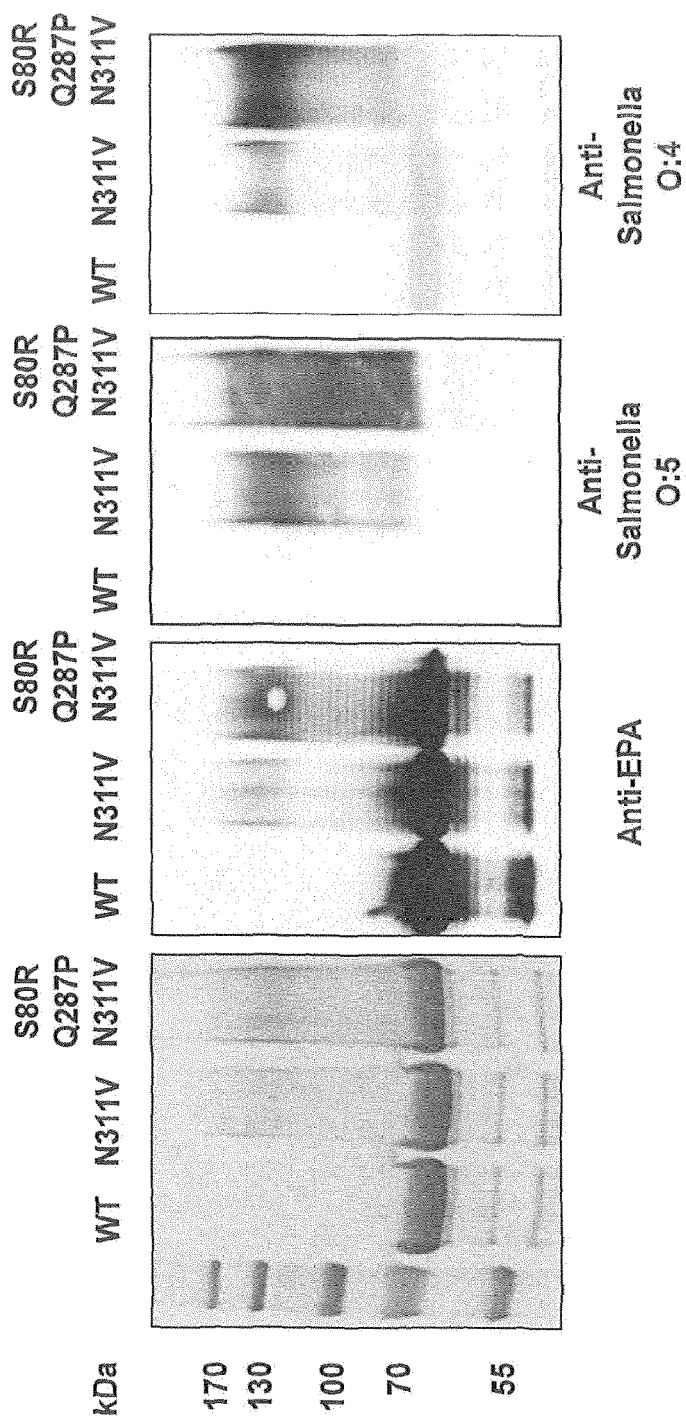

FIG. 9A-9C depicts exemplary results of a third round of directed evolution of PglBCj, employing shuffling of neutral and slightly beneficial mutations. FIG. 9A illustrates screening results for a representative 96-well library. Open circles illustrate library clones; filled triangles illustrate PglB N311V (template plasmid pGVXN1418); shaded triangles illustrate inactive PglBmut (pGVXN408). FIG. 9B illustrates a verification of improvements in DWP after retransformation. Average values and standard deviations for n=3 replicate clones/wells per variant plasmid, wt: pGVXN1413 and N311V: pGVXN1418 are depicted. FIG. 9C illustrates exemplary results of a SDS-PAGE and Western blot analysis of Ni-NTA affinity purified proteins produced with either wild-type PglB (pGVXN970), PglB N311V (pGVXN1217) or PglB S80R-Q287P-N311V (library clone 2B2) in shake flasks (similar loading volumes, total protein concentration (A280) was adjusted to 2 mg mL-1). Theoretical molecular weight of unglycosylated EPA-6H: 69.4 kDa.

Figure 10:
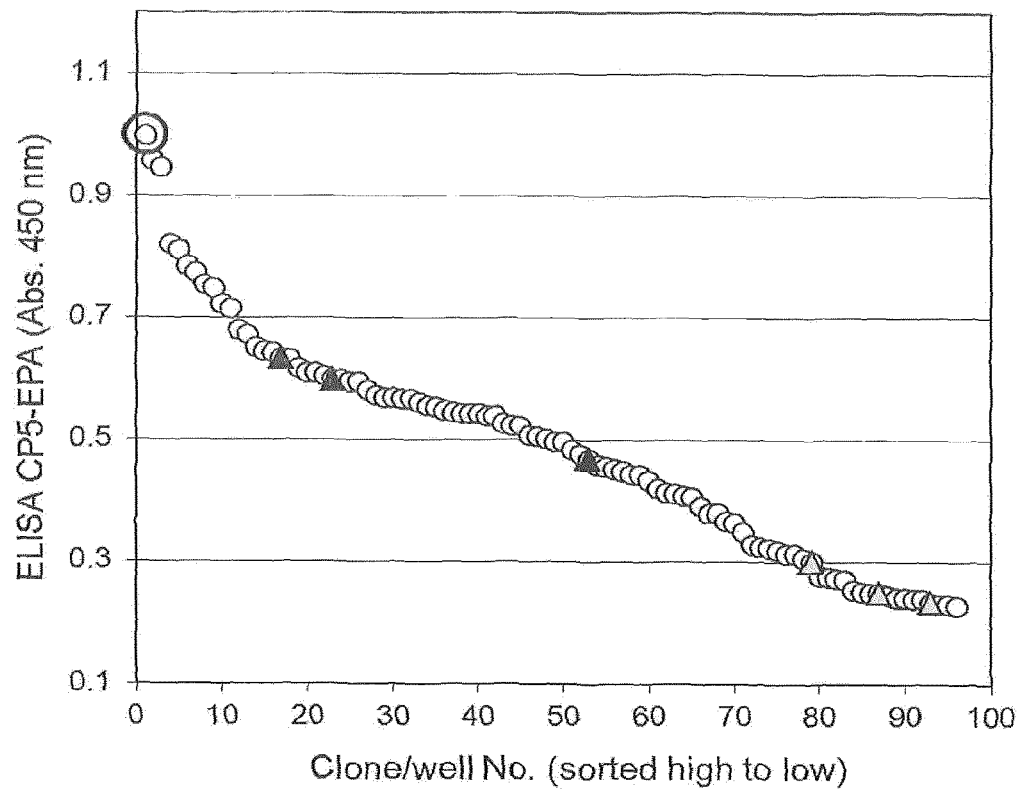

FIG. 10 depicts exemplary screening results for a PglB$_{Cj}$ library with randomized residues PglB$_{Cj}$ K482 and D483. Open circles: library clones, closed triangles: wild-type PglB-HA (pGVXN407), open triangles: inactive PglB (pGVXN408). Clone Fa8_G10 harboring the double mutation K482R-D483H is marked by a circle.

Figure 11:
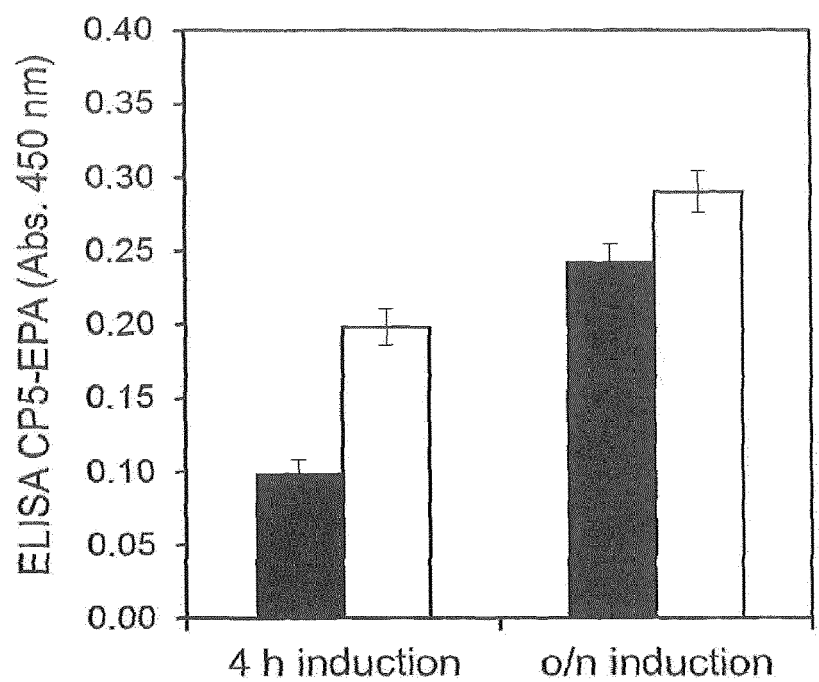

FIG. 11 shows a bar graph illustrating that PglB$_{Cj}$ K482-D483H can improve production of CP5-EPA in shake flask cultures. Biomass-normalized periplasmic protein extracts were prepared 4 h after induction and after overnight (o/n)

incubation and analysed by sandwich ELISA. Filled bats: wild-type PglBCj-HA (pGVXN114), open bars: PglBCj-HA K482R-D483H (pGVXN635). Average values and standard deviations of n=3 replicate cultures. Background ELISA absorbance was subtracted (inactive PglB, pGVXN115).

Figure 12:
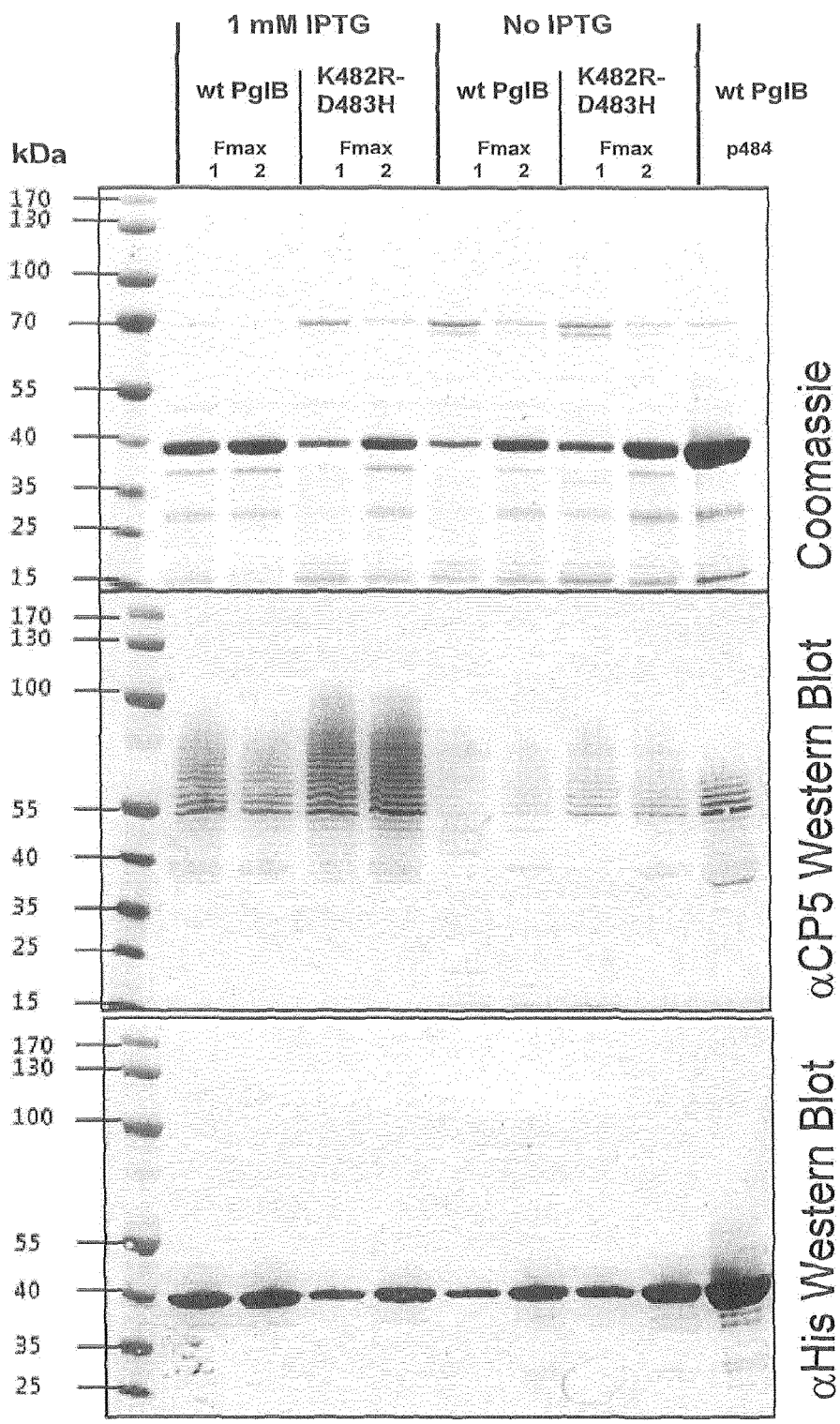

FIG. 12 shows a Western Blot analysis illustrating that PglB$_{Cj}$ K482-D483H can improve glycosylation of *S. aureus* Hla with *S. aureus* CP5 polysaccharides. SDS-PAGE and Western blot analysis of periplasmic proteins after HisTrap purification are shown. Similar volumes of the elution fractions with the highest protein concentrations(A280) were loaded.

5. ABBREVIATIONS

The abbreviation "CP," as used herein, means "capsular polysaccharide."

The abbreviation "EL" as used herein, means "external loop."

The abbreviation "N-OST," as used herein, means N-oligosaccharyl transferase.

The abbreviation "$PglB_{Cj}$," as used herein, refers to the N-OST PglB of *Campylobacter jejuni* (*C. jejuni*).

The abbreviation "$PglB_{Cl}$," as used herein, refers to the N-OST PglB of *Campylobacter lari* (*C. lari*).

6. DETAILED DESCRIPTION

Provided herein is a modified N-oligosaccharyl transferase (N-OST) with a modified substrate specificity. Specifically, provided herein are modified N-OST's that are capable of using oligo- or polysaccharides as substrates for N-glycosylating proteins at an N-glycosylation consensus sequence that cannot be used (or cannot be used at detectable levels) by the wild type form of the N-OST. In certain embodiments, the modified N-OST can use such an oligo- or polysaccharide to produce detectable levels of an N-glycosylated carrier protein, e.g., in vivo or in vitro. Levels of glycosylated carrier protein can be determined by methods known in the art, including, without limitation, ELISA, HPLC, LC-MS and the like; see, e.g., Section 6.10, Section 6.12, and Examples 2-3). In some embodiments, production of the N-glycosylated carrier protein is detected by ELISA.

In some embodiments, the levels of glycosylated carrier protein are detectable if the glycosylated carrier protein can be detected in an assay with a signal indicating glycosylated carrier protein at levels more than two or three standard deviations (>2σ or >3σ) above the average or median assay background signal, or more than 2-fold, more than 3-fold, more than 4-fold, more than 5-fold, more than 7-fold, more than 8-fold, more than 9-fold, or more than 10-fold above the assay background signal.

In some embodiments, the assay background signal is the average or median assay signal of negative control experiments performed in the absence of an N-OST. In some embodiments, the assay background signal is the average or median assay signal of negative control experiments performed in the presence of a wild-type N-OST.

In certain embodiments, the glycosylated carrier protein can be detected at a level that is more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold above the background level in an assay detecting the bioconjugate (e.g., in an ELISA assay, by HPLC, LC-MS; see also Section 6.10 and Section 6.12).

A modification in an N-OST provided herein can be located within a specified distance from the monosaccharide unit at the reducing end of the oligo- or polysaccharide component of a glycosylated carrier protein that is bound to the N-OST. To confirm that such a modification results in the altered substrate specificity any routine assay for protein glycosylation can be used. Such modified N-OST's can be used to generate bioconjugates in prokaryotic host cells as described herein. Compositions comprising the resulting bioconjugates are also disclosed herein. In a specific embodiment, such a modified N-OST is capable of using an oligo- or polysaccharide that lacks an N-acetyl substituted sugar at the reducing end as a substrate to produce detectable levels of a glycosylated carrier protein.

In some embodiments, the recombinant N-oligsaccharyl transferase mutant can increase the yield of bioconjugate production to a level of more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold above background level in an assay detecting the bioconjugate.

The background level in an assay detecting a bioconjugate can be, e.g., the average or median signal obtained in control experiments that are performed in the absence of the N-OST or that are performed using wild-type N-OST.

6.1 N-Oligosaccharyl Transferases

In one aspect, provided herein is a recombinant N-oligosaccharyl transferase (N-OST), wherein the recombinant N-OST can delectably link an oligosaccharide or a polysaccharide lacking an N-acetyl sugar at the reducing end to a carrier protein. In some embodiments, the recombinant N-OST comprises modifications of one or more amino acids whose side chains are located within a 0.5-10.0 Å distance from the monosaccharide unit at the reducing end of the polysaccharide component of a bound glycosylated carrier protein product in a structural model of a complex of the recombinant N-OST and the glycosylated carrier protein product. In some embodiments, the modification is an amino acid substitution. In some embodiments, the recombinant N-OST comprises modifications of one or more amino acids whose side chains are located within a 2.5-4.0 Å distance from one of the three terminal monosaccharide units at the reducing end of the polysaccharide component of a bound glycosylated carrier protein product in a structural model of a complex of the recombinant N-OST and the glycosylated carrier protein product. In some embodiments, the modification is an amino acid substitution. See, e.g., FIG. 2A-2C and Section 6.3.

In another aspect, provided herein is a recombinant N-OST including modifications of one or more amino acids whose side chains are located within a 1.0-10.0 Å distance from the monosaccharide unit at the reducing end of the oligosaccharide or polysaccharide component of a bound N-glycosylated carrier protein in a structural model of a complex of the recombinant N-OST and the N-glycosylated carrier protein. In some embodiments, the recombinant N-OST is a recombinant N-OST including modifications of one or more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of the recombinant N-OST and the N-glycosylated carrier protein. In some embodiments, the recombinant N-OST can detectably link an oligosaccharide or a polysaccharide lacking an N-acetyl sugar at the reducing end to a carrier protein. In some embodiments, the modification is an amino acid substitution. See, e.g., FIG. 2A-2C and Section 6.3.

In some embodiments, the 2.5-4.0 Å distance is the distance from the first terminal monosaccharide unit at the reducing end of the oligosaccharide or polysaccharide component. In some embodiments, the 2.5-4.0 Å distance is from the second terminal monosaccharide unit at the reducing end of the oligosaccharide or polysaccharide component. In some embodiments, the 2.5-4.0 Å distance is from the third terminal monosaccharide unit at the reducing end of the oligosaccharide or polysaccharide component. In some embodiments, the 2.5-4.0 Å distance is from a conserved amino acid in the catalytic center of the recombinant N-oligosaccharyl transferase in the structural model of a complex of the recombinant N-oligosaccharyl transferase and the N-glycosylated carrier protein (e.g., K522, N311, H 479, G476, Y462, G477, Y77, S80, or S199 of PglB$_{Cj}$, see, e.g., FIG. 2A-2C).

In some embodiments, the 0.5-10.0 Å distance from the monosaccharide unit at the reducing end of the oligosaccharide or polysaccharide component of a bound N-glycosylated carrier protein in a structural model of a complex of the recombinant N-OST and the N-glycosylated carrier protein is a distance of between about 1.0 and 9.0 Å, a distance of between about 1.5 and about 8.0 Å, a distance of between about 2.0 Å and about 6.0 Å or a distance of between about 2.5 Å and 4.0 Å. In some embodiments, the 1.0-10.0 Å distance from the monosaccharide unit at the reducing end of the oligosaccharide or polysaccharide component of a bound N-glycosylated carrier protein in a structural model of a complex of the recombinant N-OST and the N-glycosylated carrier protein is a distance of about 1.0 Å, of about 1.5 Å, of about 2.0 Å, of about 2.5 Å, of about 3.0 Å, of about 3.5 Å, of about 4.0 Å, of about 4.5 Å, of about 5.0 Å, of about 5.5 Å, of about 6.0 Å, of about 6.5 Å, of about 7.0 Å, of about 7.5 Å, of about 8.0 Å, of about 8.5 Å, of about 9.0 Å or of about 10.0 Å. See, e.g., FIG. 2A-2C and Section 6.3.

Assays to confirm the activity of the N-OSTs described herein are well known to skilled artisans (e.g., ELISA, Western Blot) and include the assays described in Sections 6.10 and 6.12. In some embodiments, the recombinant N-OST includes modifications of one or more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of the recombinant N-OST and the N-glycosylated carrier protein, the recombinant N-OST can detectably link the oligosaccharide or the polysaccharide lacking the N-acetyl sugar at the reducing end to the carrier protein and die activity of the N-OST can be confirmed by an assay described in Sections 6.10 or 6.12. In some embodiments, the modification is an amino acid substitution.

The oligosaccharides and polysaccharides can include any oligosaccharide or polysaccharide described herein. See, e.g., Section 6.4.

The carrier proteins can comprise any carrier protein described herein. See, e.g., Section 6.5.

In some embodiments, the recombinant N-OST comprises modifications in, e.g., two or more, three or more, four or more, five or more, six or more, seven or more, eight or more, nine or more, or ten or more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of an N-OST and the glycosylated carrier protein product.

In some embodiments, at least one or more modifications in the one more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of an N-OST and the glycosylated carrier protein product are located in a periplasmatic loop of a N-OST transmembrane domain. In some embodiments, the periplasmatic loop is the large external loop 5 (EL5) of an N-OST. In some embodiments, the periplasmatic loop is EL5 of PglB$_{Cj}$, of a PglB$_{Cj}$ homologue, or of naturally occurring variants thereof (see, e.g., FIGS. 4 and 9 for listing of PglB$_{Cj}$ homologues).

N-OSTs can include conserved sequence motifs, such as the QLKFYxxR motif. See, e.g., FIG. 9A-9C. In some embodiments, the recombinant N-OST comprises modifications in at least one amino acids in the QLKFYxxR motif. In some embodiments, the QLKFYxxR motif is a Q287LKFYxxR294 motif (see, e.g., PglBCj according to SEQ ID NO:1). In some embodiments, the recombinant N-OST comprises modifications, e.g., in at least two, at least three, at least four or at least five amino acids in the QLKFYxxRmotif. In some embodiments, the QLKFYxxR motif is the QLKFYxxR motif of PglBCj, of a PglBCj homologue, or of naturally occurring variants thereof.

In some embodiments, the recombinant N-OST comprises modifications of one or more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of an N-OST and the N-glycosylated carrier protein and further comprises a modifications in one or more amino acids in a QLKFYxxR motif.

In some embodiments, the amino acid modifications comprise an amino acid substitution. An amino acid can be substituted for a natural proteinogenic amino acid or for an artificial amino acid. In some embodiments, the amino acid modifications comprise a substitution of a non-conserved amino acid (i.e., modifications of amino acids that are not conserved between N-OSTs from different organisms). In some embodiments, the non-conserved amino acid is conserved in less than 90%, less than 80%, less than 70%, less than 60%, less than 50%, less than 40%, less than 30%, less than 20% or less than 10% of members of the phylogenetic family of N-oligosaccharyl transferases. In some embodiments, the non-conserved amino acid is conserved in about between about 10% and about 90%, between about 20% and about 80%, between about 30% and about 70% or between about 40% and about 60% of members of the phylogenetic family of N-oligosaccharyl transferases.

In some embodiments, the recombinant N-OST can increase the in vivo or in vitro rate of glycosylation of a carrier protein with a polysaccharide by between about 2-fold and about 100-fold, by between about 5-fold and about 80-fold, by between about 10-fold and about 60-fold, by between about 10-fold and about 20-fold or by between about 20-fold and about 40-fold compared to the rate of a wild-type form of the recombinant N-OST. In some embodiments, the recombinant N-OST can increase the in vivo or in vitro rate of glycosylation of a carrier protein with a polysaccharide by more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold compared to the rate of a wild-type form of the recombinant N-OST.

In some embodiments, the rates of glycosylation of the recombinant N-OST and the wild-type form of the recombinant N-OST can be compared by comparing the recombinant N-OST's and the wild-type N-OST's rates of glycosylation of a carrier protein with a polysaccharide or oligosaccharide lacking an N-acetyl sugar at the reducing end.

In some embodiments, the recombinant N-OST's rate of glycosylation of a carrier protein with a polysaccharide or oligosaccharide lacking an N-acetyl sugar at the reducing end is compared to a wild-type N-OST's rate of glycosylation of a carrier protein with a polysaccharide or oligosaccharide having an N-acetyl sugar at the reducing end.

In some embodiments, the wild-type N-OST's rate of glycosylation of a carrier protein with a polysaccharide or oligosaccharide having an N-acetyl sugar at the reducing end is defined as a relative rate of 100%.

In some embodiments, the recombinant N-OST's rate of glycosylation of a carrier protein with a polysaccharide or oligosaccharide lacking an N-acetyl sugar at the reducing end is at least 10%, at least 15%, at least 20%, at least 25%, at least 30%, at least 35%, at least 40%, at least 45%, at least 50%, at least 55%, at least 60%, at least 65%, at least 70%, at least 75%, or at least 80% of the relative rate of a wild-type N-OST.

In some embodiments, the recombinant N-OST can increase the in vivo or in vitro yield of glycosylation of a carrier protein with a polysaccharide by between about 2-fold and about 100-fold, by between about 5-fold and about 80-fold, by between about 10-fold and about 60-fold, by between about 10-fold and about 20-fold or by between about 20-fold and about 40-fold compared to the yield achieved with a wild-type form of the recombinant N-OST. In some embodiments, the recombinant N-OST can increase the in vivo or in vitro yield of glycosylation of a carrier protein with a polysaccharide by more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold compared to the yield achieved with a wild-type form of the recombinant N-OST.

In some embodiments, the recombinant N-OST can yield an in vivo glycosylation level or an in vitro glycosylation level of the carrier protein of between about 1% to about 70%, of between about 3% to about 65%, of between about 5% to about 60%, of between about 5% to about 55%, of between about 10% to about 50%, of between about 15% to about 45%, of between about 20% to about 40%, or of between about 25% to about 35%. In some embodiments, the recombinant N-OST can yield an in vivo glycosylation level or an in vitro glycosylation level of the carrier protein of at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70%.

In some embodiments, the carrier protein comprises two or more N-glycosylation consensus sequences. In some embodiments, the recombinant N-OST can in vitro or in vivo glycosylate all N-glycosylation consensus sequences in the carrier protein. In some embodiments, the recombinant N-OST can glycosylate at least 10%, at least 20%, at least 30%, at least 40%, at least 50%, at least 60%, at least 70%, at least 80%, or at least 90% of all N-glycosylation consensus sequences in the carrier protein. In some embodiments, the recombinant N-OST can in vitro or in vivo glycosylate between about 10% and about 70%, between 20% and about 60%, or between about 30% and about 50% of all N-glycosylation consensus sequences in a carrier protein.

In some embodiments, the carrier protein comprises one or more N-glycosylation consensus sequences. In some embodiments, the carrier protein is a population of carrier proteins. In some embodiments, the recombinant N-OST can in vitro or in vivo glycosylate at least at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% of all N-glycosylation consensus sequences in the carrier proteins of a population of carrier proteins. In some embodiments, the recombinant N-OST can in vitro or in vivo glycosylate between about 10% and about 70%, between 20% and about 60%, or between about 30% and about 50% of all N-glycosylation consensus sequences in the carrier proteins of a population of carrier proteins.

The recombinant N-OST can be from any organism having an N-OST. In some embodiments, the recombinant N-OST is from a eukaryotic organism. In some embodiments, the recombinant N-OST is from a prokaryotic organism. In some embodiments, the recombinant N-OST is from *Campylobacter jejuni* (*C. jejuni*), *Campylobacter coli* (*C. coli*), *Campylobacter lari* (*C. lari*), *Campylobacter upsaliensis* (*C. upsaliensis*), *Campylobacter curvus* (*C. curvus*), *Campylobacter concisus* (*C. concisus*), *Campylobacter hominis* (*C. hominis*), *Campylobacter gracilis* (*C. gracilis*), *Campylobacter showae* (*C. showae*), *Sulfurimonas autotrophica* (*S. autotrophica*), *Sulfurimonas denitrificans* (*S. denitrificans*), *Sulfurospirillum deleyianum* (*S. deleyianum*), *Sulfuricurvum kujiense* (*S. kujiense*), *Nautilia profundicola* (*N. profundicola*), *Sulfuvorum* sp. NBC37-1, *Wolinella succinogenes* (*W. succinogenes*), *Caminibacter mediatlanticus* (*C. mediatlanlicus*), *Nitratiruptor* sp. SB155-2, *Helicobacter pullorum* (*H. pullorum*), *Helicobacter Canadensis* (*H. Canadensis*), *Helicobacter winghamensis* (*Helicobacter winghamensis*), *Desulfurobacterium thermolithotr* (*D. thermolithotr*), *Desulfomicrobium baculatum* (*D. baculatum*), *Desulfovibrio vulgaris* (*D. vulgaris*), *Desulfovibrio alkaliphilus* (*D. alkaliphilus*), *Desulfohalobium retbaense* (*D. retbaense*), *Deferribacter desulfuricans* (*D. desulfuricans*), *Desulfovibrio salexigenes* (*D. salexigenes*), *Desulfovibrio piger* (*D. salexigenes*), *Desulfovibrio aespoeensis* (*D. aespoeensis*), Cand. *Puniceispirillum marinum*, *Calditerrivibrio nilroreducens* (*C. nitroreducens*) or *Methanothermus fervidus* (*M. fervidus*).

In some embodiments, the recombinant N-OST is derived from a prokaryotic organism from the genus *Campylobacter*. In some embodiments, the recombinant N-OST is from *Campylobacter jejuni* or *Campylobacter lari* (e.g., the pglB gene product PglB from *C. jejuni*, PglB$_{Cj}$, or from *C. lari*, PglB$_{Cl}$).

In some embodiments, the recombinant N-OST is a recombinant PglB$_{Cj}$, a recombinant PglB$_{Cj}$ homologue or a recombinant version of a naturally occurring PglB$_{Cj}$ variant. PglB$_{Cj}$ homologues can comprise naturally occurring PglB$_{Cj}$ homologues, e.g., as exemplified in FIGS. 4 and 6, and non-naturally occurring PglB$_{Cj}$ homologues. PglB$_{Cj}$ homologues can comprise proteins having at least 70%, at least 75%, at least 80%, at least 85%, at least 90%, at least 95%, at least 96%, at least 97%, at least 98% or at least 99% sequence identity to a PglB$_{Cj}$ of SEQ ID NO:1.

In some embodiments, the recombinant N-OST is a recombinant PglB$_{Cl}$, a recombinant PglB$_{Cl}$ homologue or a recombinant version of a naturally occurring PglB$_{Cl}$ variant. PglB$_{Cl}$ homologues can comprise naturally occurring PglB$_{Cl}$ homologues, e.g., as exemplified in FIG. 4, and non-naturally occurring PglB$_{Cl}$ homologues. PglB$_{Cl}$ homologues can comprise proteins having at least 70%, at least 75%, at least 80%, at least 85%, at least 90%, at least 95%, at least 96%, at least 97%, at least 98% or at least 99% sequence identity to a PglB$_{Cl}$ of SEQ ID NO:2.

Some amino acid positions are conserved in different members of a phylogenetic N-OST family. See, e.g., FIG. 4. Some amino acid positions are conserved in at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or in 100% of members of a phylogenetic N-OST family. In some embodiments, amino acids in conserved amino acid positions are modified in the recombinant N-OSTs provided herein.

In some embodiments, the recombinant modified N-OST comprises a PglB fragment, e.g., a PglB$_{Cj}$ fragment or a PglB$_{Cl}$ fragment. In some embodiments, the PglB fragment comprises at least 100, at least 150, at least 200, at least 250, at least 300, at least 350, at least 400, at least 450, at least 500, at least 550, at least 600, or at least 650 consequtive amino acids of a full-length PglB.

(a) PglB$_{Cj}$ Modifications

In some embodiments, the modified N-OSTs described herein are modified wild-type N-OSTs, e.g., wild-type PglB$_{Cj}$. In some embodiments, the wild-type PglB$_{Cj}$ is a wild-type PglB$_{Cj}$ of SEQ ID NO:1, or of a naturally occurring variant thereof:

```
MLKKEYLKNP YLVLFAMIIL AYVFSVFCRF YWVWWASEFN

EYFFNNQLMI ISNDGYAFAE GARDMIAGFH QPNDLSYYGS

SLSALTYWLY KITPFSFESI ILYMSTFLSS LVVIPTILLA

NEYKRPLMGF VAALLASIAN SYYNRTMSGY YDTDMLVIVL

PMFILFFMVR MILKKDFFSL IALPLFIGIY LWWYPSSYTL

NVALIGLFLI YTLIFHRKEK IFYIAVILSS LTLSNIAWFY

QSAIIVILFA LFALEQKRLN FMIIGILGSA TLIFLILSGG

VDPILYQLKF YIFRSDESAN LTQGFMYFNV NQTIQEVENV

DLSEFMRRIS GSEIVFLFSL FGFVWLLRKH KSMIMALPIL
```

-continued
```
VLGFLALKGG LRFTIYSVPV MALGFGFLLS EFKAIMVKKY

SQLTSNVCIV FATILTLAPV FIHIYNYKAP TVFSQNEASL

LNQLKNIANR EDYVVTWWDY GYPVRYYSDV KTLVDGGKHL

GKDNFFPSFA LSKDEQAAAN MARLSVEYTE KSFYAPQNDI

LKTDILQAMM KDYNQSNVDL FLASLSKPDF KIDTPKTRDI

YLYMPARMSL IFSTVASFSF INLDTGVLDK PFTFSTAYPL

DVKNGEIYLS NGVVLSDDFR SFKIGDNVVS VNSIVEINSI

KQGEYKITPI DDKAQFYIFY LKDSAIPYAQ FILMDKTMFN

SAYVQMFFLG NYDKNLFDLV INSRDAKVFK LKIYPYDVPD

YA
```

In some embodiments, one or more of amino acids Y77, S80, S196, N311, Y462, H479, K522, G476 or G477 of PglB$_{Cj}$, or any combination thereof, are modified.

In some embodiments, the amino acid N311 of PglB$_{Cj}$ is modified. In some embodiments, the modification of N311 is a N311V or a N311I substitution. In some embodiments, the modification of N311 is a N311V substitution.

In some embodiments, the amino acids N311 and Y77 of PglB$_{Cj}$ are modified. In some embodiments, the modification of Y77 is a Y77H, Y77T, Y77W, Y77R, Y77K, Y77A, or Y77G substitution. In some embodiments, the modification of Y77 is a Y77H substitution.

In some embodiments, the amino acids N311 and S80 of PglB$_{Cj}$ are modified. In some embodiments, the modification of S80 is a S80R substitution or a S80H substitution. In some embodiments, the modification of S80 is a S80R substitution.

In some embodiments, the recombinant PglB$_{Cj}$ comprises a modification in at least one amino acid of the Q287LKFYxxR294 motif of PglB$_{Cj}$. In some embodiments, at least one amino acid of Q287, L288 or K289 of PglB$_{Cj}$ are modified. In some embodiments, the recombinant PglB$_{Cj}$ comprises a Q287P, Q287K, Q287R, L288M, L288F, L288I, L288C, K289R, K289N, K289Q or R294K substitution.

In another embodiment, provided herein is a recombinant PglB$_{Cj}$ comprising an N311V substitution.

In another embodiment, provided herein is a recombinant PglB$_{Cj}$ comprising an N311V substitution and a Y77H substitution.

In another embodiment, provided herein is a recombinant PglB$_{Cj}$ comprising an N311V substitution and a S80R substitution.

In another embodiment, provided herein is a recombinant PglB$_{Cj}$ comprising a Y77H substitution and a Q287P substitution.

In another embodiment, provided herein is a recombinant PglB$_{Cj}$ comprising a S80R substitution and a Q287P substitution.

In another embodiment, provided herein is a recombinant PglB$_{Cj}$ comprising an N311V substitution, a S80R substitution and a Q287P substitution.

In another embodiment, provided herein is a recombinant PglB$_{Cj}$ comprising an N311V substitution, a Y77H substitution and a Q287P substitution.

In another embodiment, provided herein is a recombinant PglB$_{Cj}$ comprising an N311V mutation, aY77H substitution, a S80R substitution and a Q287P substitution.

In another embodiment, provided herein is a recombinant PglB$_{Cj}$ comprising an N311V substitution, a Y77H substitution, a S80R substitution, a Q287P substitution and a K289R substitution.

In another embodiment, provided herein is a recombinant PglB$_{Cj}$ comprising g a N311V substitution and a A699V substitution.

In another embodiment, provided herein is a recombinant PglB$_{Cj}$ comprising a K482R substitution and a D483H substitution.

In some embodiments, the substitution can be a conservative amino acid substitution (e.g., from one basic amino acid to another basic amino acid). In some embodiments, the substitution can be a non-conservative amino acid substitution (e.g., from a basic amino acid to an acidic amino acid).

(b) PglB$_{Cj}$ Modifications

In some embodiments, the modified N-OSTs described herein are modified wild-type NOSTs, e.g., wild-type PglB$_{Cj}$ (PglB of *Campylobacter lari*). In some embodiments, the wild-type PglB$_{Cj}$ is a wild-type PglB$_{Cj}$ of SEQ ID NO:2, or of a naturally occurring variant thereof:

```
MKLQQNFTDN NSIKYTCILI LIAFAFSVLC RLYWVAWASE

FYEFFFNDQL MITTNDGYAF AEGARDMIAG FHQPNDLSYF

GSSLSTLTYW LYSILPFSFE SIILYMSAFF ASLIVVPIIL

IAREYKLTTY GFIAALLGSI ANSYYNRTMS GYYDTDMLVL

VLPMLILLTF IRLTINKDIF TLLLSPVFIM IYLWWYPSSY

SLNFAMIGLF GLYTLVFHRK EKIFYLTIAL MIIALSMLAW

QYKLALIVLL FAIFAFKEEK INFYMIWALI FISILILHLS

GGLDPVLYQL KFYVFKASDV QNLKDAAFMY FNVNETIMEV

NTIDPEVFMQ RISSSVLVFI LSFIGFILLC KDHKSMLLAL

PMLALGFMAL RAGLRFTIYA VPVMALGFGY FLYAFFNFLE

KKQIKLSLRN KNILLILIAF FSISPALMHI YYYKSSTVFT

SYEASILNDL KNKAQREDYV VAWWDYGYPI RYYSDVKTLI

DGGKHLGKDN FFSSFVLSKE QIPAANMARL SVEYTEKSFK

ENYPDVLKAM VKDYNKTSAK DFLESLNDKD FKFDTNKTRD

VYIYMPYRML RIMPVVAQFA NTNPDNGEQE KSLFFSQANA

IAQDKTTGSV MLDNGVEIIN DFRALKVEGA SIPLKAFVDI

ESITNGKFYY NEIDSKAQIY LLFLREYKSF VILDESLYNS

SYIQMFLLNQ YDQDLFEQIT NDTRAKIYRL KR
```

In some embodiments, one or more of amino acids Y79, S82, N314, K488, or D489 of PglB$_{Cj}$, or any combination thereof, are modified.

In some embodiments, the amino acid N314 of PglB$_{Cl}$ is modified, in some embodiments, the modification of N314 is a N314V or a N314I substitution. In some embodiments, the modification of N314 is a N314V substitution.

In some embodiments, the amino acids N314 and Y797 of PglB$_{Cl}$ are modified. In some embodiments, the modification of Y79 is a Y79H, Y79T, Y79W, Y79R, Y79K, Y79A, or Y79G substitution. In some embodiments, the modification of Y79 is a Y79H substitution.

In some embodiments, the amino acids N314 and S82 of PglB$_{Cl}$ are modified. In some embodiments, the modification of S82 is a S82R substitution or a S82H substitution. In some embodiments, the modification of S82 is a S82R substitution.

In some embodiments, the recombinant PglB$_{Cl}$ comprises a modification in at least one amino acid of the QLKFYxxR motif of PglB$_{Cl}$. In some embodiments, at least one the amino acid Q289 is modified. In some embodiments, the recombinant PglB$_{Cl}$ comprises a Q289P, Q289K, or Q289R substitution.

In another embodiment, provided herein is a recombinant PglB$_{Cl}$ comprising an N314V substitution.

In another embodiment, provided herein is a recombinant PglB$_{Cl}$ comprising an N314V substitution and a Y79H substitution.

In another embodiment, provided herein is a recombinant PglB$_{Cl}$ comprising an N314V substitution and a S82R substitution.

In another embodiment, provided herein is a recombinant PglB$_{Cl}$ comprising a Y79H substitution and a Q289P substitution.

In another embodiment, provided herein is a recombinant PglB$_{Cl}$ comprising a S82R substitution and a Q289P substitution.

In another embodiment, provided herein is a recombinant PglB$_{Cl}$ comprising an N314V substitution, a S82R substitution and a Q289P substitution.

In another embodiment, provided herein is a recombinant PglB$_{Cj}$ comprising an N314V substitution, a Y79H substitution and a Q289P substitution.

In another embodiment, provided herein is a recombinant PglB$_{Cl}$ comprising an N314V mutation, a Y79H substitution, a S82R substitution and a Q289P substitution.

In some embodiments, the substitution can be a conservative amino acid substitution (e.g., from one basic amino acid to another basic amino acid). In some embodiments, the substitution can be a non-conservative amino acid substitution (e.g., from a basic amino acid to an acidic amino acid).

6.2 Methods of Screening

In another aspect, provided herein is a method of screening a library of recombinant N-OSTs provided herein, including contacting each member of the library of recombinant N-OSTs with a carrier protein and an oligosaccharide or a polysaccharide lacking an N-acetyl sugar at its reducing end to produce a bioconjugate.

In some embodiments, the bioconjugate is a N-glycosylated carrier protein.

The oligosaccharides and polysaccharides can include any oligosaccharide or polysaccharide described herein. See, e.g., Section 6.4.

The carrier proteins can comprise any carrier protein described herein. See, e.g., Section 6.5.

In some embodiments, the contacting occurs in vitro. In some embodiments, the contacting occurs in vivo. In some embodiments, the contacting occurs in a host cell described herein. In some embodiments, the host cell is a prokaryotic cell. In some embodiments, the host cell is an *E. coli* cell.

In some embodiments, the library of recombinant N-OSTs comprises one or more recombinant N-OSTs provided herein. In some embodiments, the library of recombinant N-OSTs comprises at least 2, at least 5, at least 10, at least 15, at least 20, at least 25, at least 50, at least 75, at least 100, at least 150, at least 200, at least 250, at least 500, at least 750 or at least 1,000 recombinant N-OSTs. In some embodiments, the library of recombinant N-OSTs comprises between about 2 and about 1,000, between about 10 and about 800, between about 50 and about 600, between about 100 and about 400, or between about 100 and about 200 recombinant N-OSTs.

In some embodiments, the method further comprises determining the rate or yield of production of the bioconjugate. In some embodiments, the method further comprises determining the its level of conjugation (e.g., glycosylation level in percent glycosylated carrier protein) of the bioconjugate. Methods for determining the rate or yield of production of a bioconjugate or the level of bioconjugate conjugation are known in the art. See, e.g., Section 6.9, Section 6.10, Section 6.12, and Examples 2-3.

In some embodiments, the method further comprises selecting one or more recombinant N-OSTs form the library of recombinant N-OSTs.

In some embodiments, the one or more recombinant N-OSTs are selected if the recombinant N-OST yields bioconjugate at a rate that is between about 2-fold and about 100-fold, between about 5-fold and about 80-fold, between about 10-fold and about 60-fold, between about 10-fold and about 40-fold, between about 10-fold and about 30-fold, or between about 10-fold and about 20-fold faster than the rate of a wild-type N-OST. In some embodiments, the one or more recombinant N-OSTs are selected if the recombinant N-OST yields bioconjugate at a rate that is more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold fester than the rate of a wild-type N-OST.

In some embodiments, the one or more recombinant N-OSTs are selected if the N-OST mutant yields between about 2-fold and about 100-fold, between about 5-fold and about 80-fold, between about 10-fold and about 60-fold, between about 10-fold and about 40-fold, between about 10-fold and about 30-fold, or between about 10-fold and about 20-fold the amount of bioconjugate compared to a wild-type N-OST. In some embodiments, the one or more N-oligosaccharyl transferase mutants are selected if the N-OST mutant yields more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold the amount of bioconjugate compared to a wild-type N-OST.

In some embodiments, the one or more recombinant N-OST is selected if the recombinant N-OST glycosylates between about 1% and about 70%, between about 3% and about 65%, between about 5% and about 60%, between about 10% and about 55%, between about 15% and about 50%, between about 20% and about 45%, between about 20% and about 40%, or between about 25% and about 35% of carrier protein in vitro (e.g., in a reaction vessel) or in vivo (e.g., in a host cell). In some embodiments, the one or more recombinant N-OST is selected if the recombinant N-OST glycosylates at least 1%, at least 3%, 5%, at least 10%, at least 15%, at least 20%, at least 25%, at least 30%, at least 35%, at least 40%, at least 45%, at least 50%, at least 55%, at least 60%, at least 65%, or at least 70% of carrier protein in vitro (e.g., in a reaction vessel) or in vivo (e.g., in a host cell).

In another aspect, provided herein is a method of identifying a recombinant N-OST provided herein that has a modified substrate selectivity relative to a wild-type form of the recombinant N-OST, including substituting one or more amino acids (e.g., two or more, three or more, four or more, five or more, six or more, seven or more, eight or more, nine or more, or ten or more amino acids) whose side chains are located within a 2.5-4.0 Å distance from one of the three terminal monosaccharide units at the reducing end of the oligosaccharide or polysaccharide component of a bound N-glycosylated carrier protein in a structural model of a complex of the recombinant N-OST and the N-glycosylated carrier protein.

In some embodiments, the N-OST mutant has a modified substrate selectivity in vitro. In some embodiments, the N-OST mutant has a modified substrate selectivity in vivo.

6.3 Structural Models

The structural models used to describe the recombinant N-OSTs disclosed herein comprise a complex of the recombinant N-OST and a bound N-glycosylated carrier protein and can be obtained using any methods known to a skilled artisan. For example, the structural model can be obtained using X-ray crystallography or nuclear magnetic resonance spectroscopy (NMR). Exemplary methods for obtaining structural models of protein complexes are described, e.g., in Bernhard Rupp, Biomolecular Crystallography: Principles, Practice, and Application to Structural Biology, Garland Science, 1 edition (Oct. 20, 2009); Eaton E. Lattman and Patrick J. Loll; Protein Crystallography: A Concise Guide, Johns Hopkins University Press; 1 edition (Mar. 26, 2008); Arthur G. Palmer III and Wayne J. Fairbrother; Protein NMR Spectroscopy, Second Edition: Principles and Practice; Academic Press, 2 edition (Dec. 28, 2005). The structural model can, e.g., be an x-ray structure model or an NMR structor model of a complex of an N-OST and a bound N-glycosylated carrier. In some embodiments, the structural model can be a homology model of a complex of the recombinant N-OST and the bound N-glycosylated carrier protein. See, e.g., Example 1 and FIG. 2A-2C. The oligosaccharide or polysaccharide and carrier protein components of an N-glycosylated carrier protein can be modeled in a product conformation or in a substrate conformation.

The structural models used to describe the recombinant N-OSTs disclosed herein can comprise any N-OST, any carrier protein, or any oligosaccharide or polysaccharide disclosed herein. See, e.g., Sections 6.1, 6.4, and 6.5.

The structural model can comprise the model of a foil-length recombinant N-OST or of a fragment thereof. The structural model can be built, e.g., using a recombinant N-OST, a recombinant wild-type N-OST, or a N-OST purified from an N-OST expressing organism. In some embodiments, the structural model comprises the catalytic site of the N-OST. The structural model can model a N-OST from any organism having an N-OST. The structural model can model any recombinant N-OST described herein. See, e.g., FIG. 4. In some embodiments, the structural model is a homology model generated using the experimentally solved structure of *C. lari* PglB (PDBid 3RCE) as template. See, e.g., Example 1. The structural model can be built using the oligosaccharides or polysaccharides and/or the carrier proteins described herein. The N-OST, carrier protein and oligosaccharide or polysaccharide component used to build the structural model can all be from the same organism or from two or three different organisms.

In some embodiments, the bound N-glycosylated carrier protein comprises a natural oligosaccharide or polysaccharide component (an oligosaccharide or polysaccharide component from the same organism as the N-OST). In some embodiments, the bound N-glycosylated carrier protein comprises a heterologous oligosaccharide or polysaccharide component (an ogosaccharide or polysaccharide component from a different organism than the N-OST). In some embodiments, the bound N-glycosylated carrier protein comprises a natural oligosaccharide or polysaccharide component of *Campylobacter jejuni* (*C. jejuni*; an oligosaccharide or polysaccharide component from *C. jejuni*). In some embodiments, the bound N-glycosylated carrier protein comprises a heterologous oligosaccharide or polysaccharide component of *C. jejuni* (an oligosaccharide or polysaccharide component that is not from *C. jejuni*).

In the structural model, physical distances, e.g., between certain N-OST amino acid side chains and the monosaccharide unit at the reducing end of the oligosaccharide or polysaccharide component of a bound N-glycosylated carrier protein can be determined using any method or software tools known to a skilled artisan. See, e.g., Chang, G. et al., An internal coordinate Monte-Carlo Method for Searching Conformational Space. J. Am. Chem. Soc, 1989, 111, 4379; Saunders, M., et al., Conformations of cycloheptadecane: A Comparison of Methods for Conformational Searching. J. Am. Chem. Soc. 1990, 112, 1419.

6.4 Oligosaccharides and Polysaccharides

The oligosaccharides that can be linked to a carrier protein by the recombinant N-OSTs provided herein can have between 2 and 100 monosaccharide units, e.g., 2, 4, 6, 8, 10, 15, 20, 25, 30, 40, 50, 60, 70, 80, 90 or 100 monosaccharide units. The polysaccharides that can be linked to a carrier protein by the recombinant N-OSTs provided herein can have more than 100 monosaccharide units, e.g., 101, 110, 150, 200, 300, 400, 500, 600, 700, 800, 900, 1,000 monosaccharide units or more.

The carrier proteins or N-OSTs can comprise any N-OST or any carrier protein disclosed herein. See, e.g., Section 6.1 and 6.5.

In some embodiments, the sugar at the reducing end of the oligosaccharide or polysaccharide is a pentose, hexose, or heptose. In some embodiments, the sugar at the reducing end of the oligosaccharide or polysaccharide is an aldopentose or a ketopentose. In some embodiments, the pentose is a D-arabinose, a D-lyxose, a D-ribose, a D-xylose, a D-ribulose, or a D-Xylulose. In some embodiments, the sugar at the reducing end of the oligosaccharide or polysaccharide is an aldohexose or a ketohexose. In some embodiments, the hexose is, e.g., a D-allose, D-altrose, D-glucose, D-mannose, D-gulose, D-idose, D-galactose, D-talose, D-psicose, D-fructose, D-sorbose or D-tagatose. In some embodiments, the sugar at the reducing end of the oligosaccharide or polysaccharide is a deoxy or a di-deoxy sugar, such as, e.g., a rhamnose, a fucose, or an abequose. In some embodiments, the sugar at the reducing end of the oligosaccharide or polysaccharide is an aldoheptose or a ketoheptose. In some embodiments, the heptose is a mannoheptulose.

The oligosaccharides and polysaccharides that can be linked to a carrier protein by the recombinant N-OSTs provided herein can be from any organism, e.g., a prokaryotic organism or a eukaryotic organism. In some embodiments, the oligosaccharide or polysaccharide is from a pathogenic organism, e.g., a human pathogen or an animal pathogen (e.g., a farm animal or a pet). In some embodiments, the oligosaccharide or polysaccharide is from a bacterial organism. In some embodiments, the oligosaccharide or polysaccharide can be from *E. coli*, *Salmonella* sp (e.g., *S. enterica* subsp. Enterica, *S. enterica* subsp. Salamae, *S. enterica* subsp. arizonae, *S. enterica* subsp. Diarizonae, *S. enterica* subsp. Houtenae, *S. bongori*, and *S. enterica* subsp. Indica, *Pseudomonas* sp (*P. aeruginosa*), *Klebsiella* sp. (e.g., *K. pneumonia*), Acinetobacter, *Chlamydia trachomatis*, *Vibrio cholera*, *Listeria* sp., e.g., *L. monocytogenes*, *Legionella pneumophila*, *Bordetella parapertussis*, *Burkholderia mallei* and *pseudomallei*, *Francisella tularensis*, *Campylobacter* sp. (*C. jejuni*); *Clostridium difficile*, *Staphylococcus aureus*, *Streptococcus pyrogenes*, *E coli*, *Streptococcus agalacticae*, *Neisseria meningitidis*, *Candida albicans*, *Haemophilus influenza*, *Enterococcus faecalis*, *Borrelia burgdorferi*, *Neisseria meningitidis*, *Haemophilus influenza*, *Leishmania major*.

In some embodiments, the oligosaccharide or polysaccharide comprises an antigen, e.g., an epitope that is immunogenic in a human or an animal (e.g., a farm animal or a pet). In some embodiments, the oligosaccharide or the polysaccharide comprises an O antigen of *E. coli* (e.g., O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, O187), *Salmonella* sp (*S. enterica* subsp. Enterica, *S. enterica* subsp. Salamae, *S. enterica* subsp. arizonae, *S. enterica* subsp. diarizonae, *S. enterica* subsp. houtenae, *S. bongori*, or *S. enterica* subsp. indica antigens and O types 1-67, as detailed in [44], *Pseudomonas* sp. (*P. aeruginosa* O serotypes 1-20 [45]), *Klebsiella* sp. (e.g., *K. pneumonia* serotypes O1, O2 (and subserotypes), O3, O4, O5, O6, O7, O8, O9, O10, O11, O12, [46]), *Acinetobacter* O antigens (e.g., *A. baumannii* O antigens identified in [47]), *Chlamydia trachomatis* O antigens (serotypes A, B, C, D, E, F, G, H, I, J, K, L1, L2, L3), *Vibrio cholera* O antigens O1 to 155, *Listeria* sp., in particular *L. monocytogenes* type 1, 2, 3, 4 and subserotypes thereof, *Legionella pneumophila* serotypes 1 to 15 O antigens, *Bordetella parapertussis* O antigens, *Burkholderia mallei* and *pseudomallei* O antigens, *Francisella tularensis*, *Campylobacter* sp. (*C. jejuni*); Capsular polysaccharides of *Clostridium difficile* (serotypes A, G, H, K, S1, S4, D, Cd-5, K. Toma et al. 1988, and *C. perfringens* serotypes A, B, C, D und E), *Staphylococcus aureus* type 5 and 8, *Streptococcus* pyrogenes (group B *streptococcus* capsular serotype polysaccharides), *E. coli*, *Streptococcus agalacticae* (group A streptococcal capsular polysaccharides), *Neisseria meningitidis* (serotypes A, B, C, W, Y, X), *Candida albicans*, *Haemophilus influenza*, *Enterococcus faecalis* capsular polysaccharides type I-V; and other surface polysaccharide structures, e.g., the *Borrelia burgdorferi* glycolipids ([48]), *Neisseria meningitidis* pilin O glycan [49, 50] and lipooligosaccharide (LOS), *Haemophilus influenza* LOS, *Leishmania major* lipophosphoglycan [51, 52]), tumor associated carbohydrate antigens (malaria glycosyl phosphatidylinositol, *Mycobacterium tuberculosis* arabinomannan [53]).

In some embodiments, the oligosaccharide or polysaccharide is a *Staphylococcus aureus* (*S. aureus*) or a *Salmonella enterica* sv. (*S. enterica* sv.) polysaccharide. In some embodiments, the polysaccharide is a *S. aureus* CP5 or a *S. enterica* sv. *Typhimurium* LT2 polysaccharide.

In some embodiments, the oligosaccharide or polysaccharide comprises an N-acetyl sugar at the reducing end. In some embodiments, the oligosaccharide or polysaccharide comprising the N-acetyl sugar at the reducing end can comprise, e.g., an O antigen of *E. coli* (e.g., O1, O2, O3, O4, O5, O6, O7, O8, O9, O10, O11, O12, O13, O14, O15, O16, O17, O18, O19, O20, O21, O22, O23, O24, O25, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, 0133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, O187), a capsular polysaccharide of *Staphylococcus aureus* (*S. aureus*) (e.g., CP5 or CP8), a capsular polysaccharide of *Francisella tulorensis* Schu4, a capsular polysaccharide of *S. pneumoniae* capsules (e.g., CP1, 4, 5, 12, 25, 38, 44, 45 or 46), a *Neisseria meningitidis* pilin O glycan [49, 50], a *Burkholderia mallei* and *pseudomallei* O antigen, a *Bordetella parapertussis* O antigen, a *Legionella pneumophila* serotypes 1 to 15 O antigen, a *Listeria* sp. O antigen, in particular an O antigen of *L. monocytogenes* type 1, 2, 3, 4, an O antigen of *Pseudomonas* sp. (*P. aeruginosa* O serotypes 1-20 [45]), an O antigen of *Klebsiella* sp. (e.g., *K. pneumonia* serotypes O1, O2 (and subserotypes), O3, O4, O5, O6, O7, O8, O9, O10, O11, O12, [46]), an O antigen of *Shigella* sp. (e.g., *S. dysenteriae, S. sonnet, S. flexneri, S. boydii*), an *Acinetobacter* O antigen (e.g., *A. baumamii* O antigens identified in [47]), or an O antigen of *Listeria* sp.

N-acetyl sugars can comprise an amino-acetyl (N-acetyl) substituent at one or more carbon atoms of the sugar. For example, an N-acetyl sugar can comprise an N-acetyl substituent at the C2-atom of a monosaccharide unit, such as a glucose unit (N-acetylglucosamine).

In some embodiments, the oligosaccharide or polysaccharide comprises a sugar at the reducing end that is not N-acetylated. In some embodiments, the oligosaccharide or polysaccharide comprising the non-N-acetylated sugar at the reducing end can comprise, e.g., *E. coli* O20, an antigen of *Salmonella* sp (e.g., *S. enterica* subsp. *Enterica, S. enterica* subsp. *Salamae, S. enterica* subsp. *arizonae, S. enterica* subsp. *diarizonae, S. enterica* subsp. *houtenae, S. bongori, or S. enterica* subsp. *Indica or S. Typhi*), an O antigen of type 1-67, a capsular polysaccharide of group A *Streptococcus* (*S. pyrogenes*), group B *Streptococcus*, and of *S. pneumoniae* CPS serotypes (encoding wchA, wqjG, or wcjH in their capsular gene clusters, i.e. all serotypes except CP1, 4, 5, 12, 25, 38, 44, 45, 46), or a *Salmonella enterica* sv. (*S. enterica* sv.) O antigen.

In some embodiments, the oligosaccharide or polysaccharide comprises a *S. aureus* CP5 or a *S. enterica* sv. *Typhimurium* LT2 polysaccharide, a *Vibrio cholera* O antigen (e.g., O1 to 155), or a *Listeria* sp. O antigen (e.g., *L. monocytogenes* type 1, 2, 3, 4).

In some embodiments, the oligosaccharide or polysaccharide comprises a D-N-acctylfucosamine (D-FucNAc) residue at its reducing end, such as, e.g., capsular polysaccharides of *S. aureus* serotypes 5, 8 or *P. aeruginosa* O antigen serotypes O2, O5, O11, O16.

In some embodiments, the oligosaccharide or polysaccharide comprises a 4-amino-d-N-acetylfucosamine (D-FucNAc4N) residue at its reducing end, such as, e.g., certain oligosaccharides or polysaccharides from *S. pneumoniae*, like serotype 1, *Shigella sonnei* O antigen, or *Plesiomonas shigelloides* O17.

In some embodiments, the oligosaccharide or polysaccharide comprises a D-N-acetylquinosamine (D-QuiNAc) residue at its reducing end, such as, e.g., like *P. aeruginosa* O antigen serotypes O6, O1, or *Francisella tularensis* serotype Schu4.

In some embodiments, the oligosaccharide or polysaccharide comprises a galactose residue at its reducing end, such as, e.g., *S. enterica* LT2.

In some embodiments, the oligosaccharide or polysaccharide comprises a *S. pneumoniae* capsular polysaccharide serotype 5, *E. coli* O1, O2, Cronobacter sakazakii O5, i.e., poly- and oligosaccharide with a reducing end D-GlcNAc linked to 1-4 to a L-Rhamnose in beta configuration.

6.5 Carrier Proteins

Carrier proteins can be linked to oligosaccharides or polysaccharides by the recombinant N-OSTs provided herein. See, e.g., Section 6.1.

The carrier protein can be any natural carrier protein (from the same organism as the N-OST) or any heterologous carrier protein (from a different organism than the N-OST). In some embodiments, the carrier protein is an immunogen. Carrier proteins can be full-length proteins or fragments thereof. Exemplary carrier proteins comprise, without limitation, exotoxin A of *P. aeruginosa* (EPA), CRM197, diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins. In some embodiments, the carrier protein is exotoxin A of *P. aeruginosa* (EPA).

In some embodiments, the carrier proteins N-glycosylated by a recombinant N-OST described herein are modified, e.g., modified in such a way that the protein is less toxic and or more susceptible to glycosylation, etc. In some embodiments, the carrier proteins are modified such that the number of glycosylation sites in the carrier proteins is maximized in a manner that allows for lower concentrations of the protein to be administered, e.g., in an immunogenic composition, in its bioconjugate form. Accordingly in certain embodiments, the carrier proteins described herein are modified to comprise 1, 2, 3, 4, 5, 6, 7, 8, 9, 10, or more glycosylation sites than would normally be associated with the carrier protein (e.g., relative to the number of glycosylation sites associated with the carrier protein in its native/natural, e.g., "wild-type" state). In some embodiments, introduction of glycosylation sites is accomplished by insertion of glycosylation consensus sequences (e.g., (i) the consensus sequence Asn-X-Ser (Thr), wherein X is independently selected from any amino acid except Pro; or (ii) the consensus sequence D/E-X—N—Z-S/T, wherein X and Z are independently selected from any amino acid except Pro) anywhere in the primary structure of the protein. Introduction of such glycosylation sites can be accomplished by, e.g., adding new amino acids to the primary structure of the protein (the glycosylation sites are added, in full or in part), or by modifying existing amino acids in the protein in order to generate the glycosylation sites (amino acids are not added to the protein, but selected amino acids of the protein are mutated so as to form glycosylation sites). Those of skill in the art will recognize that the amino acid sequence of a protein can be readily modified using approaches known in the art, e.g., recombinant approaches that comprise modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In certain embodiments, the classical 5 amino acid glycosylation consensus sequence may be extended by lysine residues for more efficient glycosylation, and thus the inserted consensus sequence may encode 5, 6, or 7 amino acids that should be inserted or that replace acceptor protein amino acids.

The N-OSTs can comprise any N-OST disclosed herein. See, e.g., Section 6.1.

In some embodiments, the earner proteins comprise a "tag," a sequence of amino acids that allows for the isolation and/or identification of the carrier protein. For example, adding a tag to a carrier protein described herein can be useful in the purification of that protein and, hence, the purification of conjugate vaccines comprising the tagged carrier protein. Exemplary tags that can be used herein comprise, without limitation, histidine (HIS) tags (e.g., hexa histidine-tag, or 6× His-Tag), FLAG-TAG, and HA tags. In certain embodiments, the tags used herein are removable, e.g., removal by chemical agents or by enzymatic means, once they are no longer needed, e.g., after the protein has been purified.

6.6 Nucleic Acids

In another aspect, provided herein are nucleic acids encoding the recombinant N-OSTs provided herein (e.g., Section 6.1).

In some embodiments, the nucleic acids encode a recombinant $PglB_{Cj}$ wherein one or more of amino acids Y77, S80, S196, N311, Y462, H479, K522, G476 or G477 are modified.

In some embodiments, the nucleic acids encode a $PglB_{Cj}$ wherein the amino acid N311 of $PglB_{Cj}$ is modified. In some embodiments, the modification of N311 is a N311V or a N311I substitution. In some embodiments, the modification of N311 is a N311V substitution.

In some embodiments, the nucleic acids encode a recombinant $PglB_{Cj}$ wherein the amino acids N311 and Y77 are modified. In some embodiments, the modification of Y77 is a Y77H, Y77T, Y77W, Y77R, Y77K, Y77A, or Y77G substitution. In some embodiments, the modification of Y77 is a Y77H substitution.

In some embodiments, the nucleic acids encode a recombinant $PglB_{Cj}$ wherein the amino acids N311 and S80 of $PglB_{Cj}$ are modified. In some embodiments, the modification of S80 is a S80R substitution or a S80H substitution. In some embodiments, the modification of S80 is a S80R substitution.

In some embodiments, the nucleic acids encode a recombinant $PglB_{Cj}$ wherein the recombinant $PglB_{Cj}$ comprises a modification in at least one amino acid of the Q287LKFYxxR294 motif of $PglB_{Cj}$. In some embodiments, the nucleic acids encode a recombinant $PglB_{Cj}$ wherein at least one amino acid of Q287, L288 or K289 of $PglB_{Cj}$ is modified. In some embodiments, the recombinant $PglB_{Cj}$ comprises a Q287P, Q287K, Q287R, L288M, L288F, L288I, L288C, K289R, K289N, K289Q or R294K substitution.

In another embodiment, provided herein is a nucleic acid encoding a recombinant $PglB_{Cj}$ comprising an N311V substitution.

In another embodiment, provided herein is a nucleic acid encoding a recombinant $PglB_{Cj}$ comprising an N311V substitution and a Y77H substitution.

In another embodiment, provided herein is a nucleic acid encoding a recombinant $PglB_{Cj}$ comprising an N311V substitution and a S80R substitution.

In another embodiment, provided herein is a nucleic acid encoding a recombinant $PglB_{Cj}$ comprising a Y77H substitution and a Q287P substitution.

In another embodiment, provided herein is a nucleic acid encoding a recombinant $PglB_{Cj}$ comprising a S80R substitution and a Q287P substitution.

In another embodiment, provided herein is a nucleic acid encoding a recombinant $PglB_{Cj}$ comprising an N311V substitution, a S80R substitution and a Q287P substitution.

In another embodiment, provided herein is a nucleic acid encoding a recombinant $PglB_{Cj}$ comprising an N311V substitution, a Y77H substitution and a Q287P substitution.

In another embodiment, provided herein is a nucleic acid encoding a recombinant $PglB_{Cj}$ comprising an N311V mutation, a Y77H substitution, a S80R substitution and a Q287P substitution.

In another embodiment, provided herein is a nucleic acid encoding a recombinant $PglB_{Cj}$ comprising an N311V substitution, a Y77H substitution, a S80R substitution, a Q287P substitution and a K289R substitution.

In another embodiment, provided herein is a nucleic acid encoding a recombinant $PglB_{Cj}$ comprising a N311V substitution and a A699V substitution.

In another embodiment, provided herein is a nucleic acid encoding a recombinant $PglB_{Cj}$ comprising a K482R substitution and a D483H substitution.

6.7 Host Cells

In another aspect, provided herein is a host cell comprising a recombinant N-OST provided herein. In some embodiments, the host cell comprises two or more recombinant N-OSTs provided herein (e.g., 2, 3, 4, 5, 6, 7, 8, 9, 10 or more recombinant N-OSTs).

In another aspect, provided herein is a host cell comprising a nucleic acid provided herein (e.g., encoding a recombinant N-OST provided herein, e.g., Section 6.1). See, e.g., Section 6.6. In some embodiments, the host cell comprises two or more nucleic acids provided herein (e.g., 2, 3, 4, 5, 6, 7, 8, 9, 10 or more nucleic acids).

In some embodiments, the host cell comprises one or more further enzymes useful for bioconjugate production or carrier protein N-glycosylation (e.g., a glycosyltransferase). In some embodiments, at least one of the further enzymes useful for bioconjugate production is a recombinant enzyme. In some embodiments, the host cell comprises two or more further enzymes useful for bioconjugate production (e.g., 2, 3, 4, 5, 6, 7, 8, 9, 10 or more further enzymes).

In some embodiments, the host cell is a prokaryotic cell. In some embodiments, the host cell is an *E. coli* cell. In some embodiments, the host cell comprises a recombinant N-OST provided herein. See, e.g., Section 6.1. In some embodiments, the host cell comprises a carrier protein and a recombinant N-OST provided herein. See, e.g., Section 6.1 and 6.5. In some embodiments, the host cell comprises a carrier protein, a recombinant N-OST provided herein, and a recombinant glycosyltransferase. In some embodiments, the recombinant N-OST is a recombinant PglB$_{Cj}$. See, e.g., Section 6.1(a).

In certain embodiments, the host cells used to produce the bioconjugates described herein are engineered to comprise heterologous nucleic acids, e.g., heterologous nucleic acids that encode one or more carrier proteins and/or heterologous nucleic acids that encode one or more proteins, e.g., genes encoding one or more proteins. In some embodiments, heterologous nucleic acids that encode proteins involved in glycosylation pathways (e.g., prokaryotic and/or eukaryotic glycosylation pathways) are introduced into the host cells described herein. Such nucleic acids can encode proteins including, without limitation, oligosaccharyl transferases and/or glycosyltransferases. Heterologous nucleic acids (e.g., nucleic acids that encode carrier proteins and/or nucleic acids that encode other proteins, e.g., proteins involved in glycosylation) can be introduced into the host cells described herein using any methods known to those of skill in the art, e.g., electroporation, chemical transformation by heat shock, natural transformation, phage transduction, and conjugation. In some embodiments, heterologous nucleic acids are introduced into the host cells described herein using a plasmid, e.g., the heterologous nucleic acids are expressed in the host cells by a plasmid (e.g., an expression vector). In some embodiments, heterologous nucleic acids are introduced into the host cells described herein using the method of insertion described in International Patent application Publication No. WO 2014/057109.

In certain embodiments, additional modifications can be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein or do not encode a protein whatsoever). In certain embodiments, when nucleic acids are deleted from the genome of the host cells provided herein, they are replaced by a desirable sequence, e.g., a sequence that is useful for glycoprotein production.

Exemplary genes that can be deleted in host cells (and, in some cases, replaced with other desired nucleic acid sequences) include genes of host cells involved in glycolipid biosynthesis, such as waaL (see, e.g., Feldman et al., 2005, PNAS USA 102:3016-3021), the lipid A core biosynthesis cluster (waa), galactose cluster (gal), arabinose cluster (ara), colonic acid cluster (wc), capsular polysaccharide cluster, undecaprenol-p biosynthesis genes (e.g. uppS, uppP), und-P recycling genes, metabolic enzymes involved in nucleotide activated sugar biosynthesis, enterobacterial common antigen cluster, and prophage O antigen modification clusters like the gtrABS cluster.

The host cells described herein can produce the N-glycosylated carrier proteins described herein. In some embodiments, the N-glycosylated carrier proteins produced by the host cells described herein are antigens, e.g., viral or bacterial antigens that can be used in vaccines. In some embodiments, the N-glycosylated carrier proteins produced by the host cells described herein can be any carrier proteins described herein, wherein said carrier proteins are modified by the host cells described herein so as to possess one or more beneficial characteristics, e.g., the carrier protein is N-glycosylated.

Certain of the Examples below describe application of methods described herein in Gram-negative *E. coli* host cells; however, any host cells known to those of skill in the art could be used as to produce N-glycosylated carrier proteins, including archea, prokaryotic host cells other than *E. coli*, and eukaryotic host cells.

Exemplary prokaryotic host cells that can be used in accordance with the methods described herein comprise, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species. *Staphylococcus* species, *Bacillus* species, and *Clostridium* species.

In certain embodiments, the host cells described herein comprise a genome into which one or more DNA sequences has been introduced, wherein the DNA sequences encode a protein or comprise an operon/gene cluster involved in the N-glycosylation of proteins. For example, in some embodiments, a host cell described herein comprises a genome into which one or more of the following has been inserted: DNA encoding an N-OST, DNA encoding a glycosyltransferase, DNA encoding a carrier protein, DNA comprising an rfb gene cluster, DNA comprising a capsular polysaccharide gene cluster, and/or DNA encoding an epimerase.

The host cells can include recombinant N-OSTs provided herein or nucleic acids encoding the recombinant N-OSTs provided herein, whereby the recombinant N-OSTs can be from any organism having N-OSTs, including a eukaryotic organism or a prokaryotic organism. In some embodiments, the N-OST protein or N-OST encoding nucleic acid is from the genus *Campylobacter* (e.g., the pglB gene from *C. jejuni*).

The host cells described herein can comprise a glycosyltransferase known in the art or a nucleic acid sequence encoding a glycosyltransferases known in the art. In some embodiments, the glycosyltransferase is a glycosyltransferase described in International Patent Application Publication No. WO 2011/138361, the disclosure of which is incorporated by reference herein in its entirety. In some embodiments, the glycosyltransferase is from a Gram-positive bacterium, e.g., the glycosyltransferase is from *S. aureus*. In some embodiments, the glycosyltransferase is capsular polysaccharide 5 from *S. aureus*. In some embodiments, the glycosyltransferase is capsular polysaccharide 8 from *S. aureus*. In some embodiments, the glycosyltransferase is from a Gram-negative bacterium, e.g., *E. coli*. In some embodiments, the glycosyltransferase is from a eukaryote.

The host cells described herein can comprise or produce a carrier protein known in the art or comprise a nucleic acid sequence encoding a carrier protein known in the art. The carrier proteins produced by the host cells described herein comprise at least one N-glycosylation consensus sequence, e.g., either the consensus sequence (i) Asn-X-Ser(Thr), wherein X is independently selected from any amino acid except Pro; or (ii) D/E-X—N-Z-S/T, wherein X and Z are independently selected from any amino acid except Pro.

Accordingly, the host cell can comprise DNA sequences encoding an N-glycosylation consensus sequence. The host cell can include any carrier protein known in the art, including the carrier proteins described in Section 5.5. In some embodiments, the carrier protein is an Exotoxin A of *P. aeruginosa* (EPA), including EPA that has been modified to comprise at least one N-glycosylation consensus sequence. In some embodiments, the carrier protein is cholera toxin B. In some embodiments, the carrier protein is AcrA. In some embodiments, the carrier protein is HlA. In some embodiments, the carrier protein is ClfA.

6.8 Bioconjugates

The bioconjugates described herein are conjugates between a protein (e.g., any carrier protein described herein; e.g., Section 6.5) and an oligosaccharide or a polysaccharide (e.g., any oligosaccharide or polysaccharide described herein; see, e.g., Section [00201]) prepared in a host cell, wherein host cell machinery links the oligosaccharide or polysaccharide to the protein (e.g., N-links). In some embodiments, the oligosaccharide or polysaccharide is an antigen (e.g., any antigen described herein; see, e.g., Section 6.4). Glycoconjugates can include bioconjugates, as well as sugar antigen (e.g., oligo- and polysaccharides)-protein conjugates prepared by other means, e.g., by chemical linkage of the protein and sugar antigen.

The recombinant N-OSTs described herein (see, e.g., Section 6.1) can be used to produce host cells that produce bioconjugates comprising an N-glycosylated carrier protein. In some embodiments, provided herein are bioconjugates including a carrier protein N-glycosylated with an antigen (e.g., an oligosaccharide or a polysaccharide) described herein. In some embodiments, the carrier protein is EPA. The bioconjugates described herein can, for example and without limitation, comprise any carrier protein described herein. The bioconjugates described herein can, for example and without limitation, comprise any oligosaccharide or polysaccharide described herein.

In some embodiments, the heterologous *C. Jejuni* glycosylated carrier protein is *Pseudomonas aeruginosa* exotoxin (EPA)-*S. dysenteriae* O1 (EPA-O1), EPA-*S. aureus* capsular polysaccharide Type 5 (EPA-CP5) or EPA-*Salmonella enterica* (*S. enterica*) LT2 (EPA-LT2).

In some embodiments, provided herein is a bioconjugate including EPA and one or more different oligosaccharides or polysaccharides described herein.

In some embodiments, provided herein is a bioconjugate including carrier protein conjugated to one or more of *E. coli* O1, O2, O4, O6, O7, O8, O11, O15, O16, O17, O18, O20, O22, O25, O73, O75, and/or O83. In some embodiments, the carrier protein is EPA.

In some embodiments, provided herein is a bioconjugate including a carrier protein conjugated to one or more different *P. aeruginosa* polysaccharides. In some embodiments, the carrier protein is EPA.

In some embodiments, provided herein is a bioconjugate comprising a carrier protein conjugated to one or more different *K. pneumonia* polysaccharides. In a specific embodiment, the carrier protein is EPA.

6.9 Methods for Producing a Bioconjugate

In some embodiments, the recombinant N-OSTs provided herein (see, e.g., Section 6.1) can be used to produce a bioconjugate provided herein (see, e.g., Section 6.8), such as a glycoconjugate. In some embodiments, the recombinant N-OSTs provided herein can be used to produce conjugate vaccines, i.e. vaccines that contain an oligosaccharide or polysaccharide (see, e.g., Section 5.4) and a protein antigen of the pathogen that the vaccine is designed against.

In another aspect, provided herein is a method of producing a bioconjugate including culturing a host cell provided herein (see, e.g., Section 6.7) in a cell culture medium. In some embodiments, the host cell comprises a nucleic acid encoding a recombinant modified N-OST provided herein (see, e.g., Section 6.1 and Section 6.6). In some embodiments, the host cell comprises a nucleic acid encoding a carrier protein described herein (see, e.g., Section 6.5 and Section 6.6). In some embodiments, the carrier protein has one or more N-glycosylation consensus sequence. In some embodiments, the host cell comprises a nucleic acid encoding a glycosyltransferase (see, e.g., Section 6.6 and Section 6.7).

In some embodiments, the bioconjugate is an N-glycosylated carrier protein. The N-glycosylated carrier protein can comprise an oligosaccharide or polysaccharide component including any oligosaccharide or polysaccharide described herein. See, e.g., Section [00201]. The N-glycosylated carrier protein can comprise any carrier protein described herein. See, e.g., Section 6.5. In some embodiments, the bioconjugate is a natural *C. jejuni* N-glycosylated polypeptide (including a *C. jejuni* oligosaccharide or polysaccharide component and a *C. jejuni* carrier protein). In some embodiments, the bioconjugate is a heterologous *C. jejuni* glycosylated polypeptide (including a polysaccharide component and/or a carrier protein that is not from *C. jejuni*). In some embodiments, the glycosylated polypeptide does not have an N-acetyl sugar at its reducing end. In some embodiments, the glycosylated polypeptide has a galactose at its reducing end.

In some embodiments, the bioconjugate is produced at a between about 2-fold and about 100-fold, by between about 5-fold and about 80-fold, by between about 10-fold and about 60-fold, by between about 10-fold and about 20-fold or by between about 20-fold and about 40-fold compared fester rate when using a host cell including a recombinant N-OST of this disclosure than when using a host cell including a wild-type form of the recombinant N-OST. In some embodiments, the bioconjugate is produced at a more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold faster rate when using a host cell including a recombinant N-OST of this disclosure than when using a host cell including a wild-type form of the recombinant N-OST.

In some embodiments, the bioconjugate is produced at a between about 2-fold and about 100-fold, by between about 5-fold and about 80-fold, by between about 10-fold and about 60-fold, by between about 10-fold and about 20-fold or by between about 20-fold and about 40-fold compared greater yield when using a host cell including a recombinant N-OST of this disclosure than when using a host cell including a wild-type form of the recombinant N-OST. In some embodiments, the bioconjugate is produced at a more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, mom than 70-fold, more than 80-fold, more than 90-fold or more than 100-fold greater yield when using a host cell including a recombinant N-OST of this disclosure than when using a host cell including a wild-type form of the recombinant N-OST.

In some embodiments, between about 1% to about 70%, of between about 3% to about 65%, of between about 5% to about 60%, of between about 10% to about 55%, of between about 15% to about 50%, of between about 20% to about 45%, of between about 20% to about 45%, of between about 25% to about 40%, or of between about 30% to about 35% of carrier protein in the host cell is glycosylated to form the bioconjugate.

In some embodiments, the at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% of carrier protein in the host cell is glycosylated to form the bioconjugate.

In some embodiments, the methods further comprise purifying the bioconjugate from the host cell culture. Methods for purifying bioconjugates, such as N-glycosylated carrier proteins, from host cell cultures are known in the art. See, e.g., Jan-Christer Janson, *Protein Purification: Principles, High Resolution Methods, and Applications*. Wiley; 3 edition (Mar. 22, 2011).

6.10 Analytical Methods

Various methods can be used to analyze the structural compositions and sugar chain lengths of the bioconjugates or N-glycosylated carrier proteins described herein.

In one embodiment, hydrazinolysis can be used to analyze glycans. First, polysaccharides are released from their protein carriers by incubation with hydrazine according to the manufacturer's instructions (Ludger Liberate Hydrazinolysis Glycan Release Kit, Oxfordshire, UK). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans are purified on carbon columns and subsequently labeled at the reducing end with the fluorophor 2-amino benzamide (Bigge J C, Patel T P, Bruce J A, Goulding P N, Charles S M, Parekh R B. Nonselective and efficient fluorescent labeling of glycans using 2-amino benzamide and anthranilic acid. *Anal Biochem.* 1995 Sep. 20; 230(2):229-38). The labeled polysaccharides are separated on a GlycoSep-N column (GL Sciences) according to the HPLC protocol of Royle et al. (Royle L, Mattu T S, Hart E, Langridge J I, Merry A H, Murphy N, Harvey D J, Dwek R A, Rudd P M. An analytical and structural database provides a strategy for sequencing O-glycans from microgram quantities of glycoproteins. *Anal Biochem.* 2002 May 1; 304(1): 70-90). The resulting fluorescence chromatogram indicates the polysaccharide length and number of repeating units. Structural information can be gathered by collecting individual peaks and subsequently performing MS/MS analysis. Thereby the monosaccharide composition and sequence of the repeating unit could be confirmed and additionally in homogeneity of the polysaccharide composition could be identified. Specific peaks of low molecular weight can be analyzed by MALDI-MS/MS and the result is used to confirm the glycan sequence. Each peak corresponds to a polymer consisting of a certain number of repeat units and fragments thereof. The chromatogram thus allows to measure the polymer length distribution. The elution time is a indication for polymer length, fluorescence intensity correlates with molar abundance for the respective polymer.

In another embodiment, SDS-PAGE or capillary gel electrophoresis can be used to assess glycans and glycoconjugates. Polymer length for the O antigen glycans which are synthesized here is defined by the number of repeat units that are linearly assembled. This means that the typical ladder like pattern is a consequence of different repeat unit numbers that compose the glycan. Thus, two bands next to each other in SDS PAGE or other techniques that separate by size differ by only a single repeat unit. These discrete differences are exploited when analyzing glycoproteins for glycan size: The unglycosylated carrier protein and the glycoconjugate with different polymer chain lengths separate according to their electrophoretic mobilities. The first detectable repeating unit number ($n_1$) and the average repeating unit number ($n_{average}$) present on a glycoconjugate are measured. These parameters can be used to demonstrate batch to batch consistency or polysaccharide stability.

In another embodiment, high mass MS and size exclusion HPLC could be applied to measure the size of the complete glycoconjugates.

In another embodiment, an anthrone-sulfuric acid assay can be used to measure polysaccharide yields (Leyva A, Quintana A, Sánchez M, Rodriguez E N, Cremata J, Sánchez J C. Rapid and sensitive anthrone-sulfuric acid assay in microplate format to quantify carbohydrate in biopharmaceutical products: method development and validation. *Biologicals.* 2008 March; 36(2): 134-41. Epub 2007 Nov. 26).

(a) Change in Glycosylation Site Usage

To show that the site usage in a specific protein is changed glycosylation site usage can be quantified, Methods to do so are listed below.

Glycopeptide LC-MS/MS: glycoconjugates are digested with protease(s), and the peptides are separated by a suitable chromatographic method (C18, Hydriphilic interaction HPLC HILIC, GlycoSepN columns, SE HPLC, AE HPLC), and the different peptides are identified using MS/MS. This method can be used with or without previous sugar chain shortening by chemical (smith degradation) or enzymatic methods. Quantification of glycopeptide peaks using UV detection at 215 to 280 nm allow relative determination of glycosylation site usage.

Size exclusion HPLC: Higher glycosylation site usage is reflected by a earlier elution time from a SE HPLC column. See also (a), (b) Homogeneity Glycoconjugate homogeneity (the homogeneity of the attached sugar residues) can be assessed using methods that measure glycan length and hydrodynamic radius.

6.11 Benefits

The recombinant N-OSTs provided herein (see, e.g., Section 5.1) and methods provided herein (see, e.g., Sections 6.2 and 6.9) of using the recombinant N-OST provided herein (see, e.g., Section 6.1) are of particular commercial importance and relevance, as they allow for rapid, high-yield, large-scale and low-cost fermentation of highly homogeneous bioconjugate preparations (e.g., glycoconjugate preparation or conjugate vaccine preparations). The recombinant N-OSTs provided herein enable an economically viable production of commercially and therapeutically valuable bioconjugates, such as conjugate vaccines. Enzymatic production processes using the recombinant N-OSTs provided herein is expected to yield more homogeneous and reproducible bioconjugate preparations than commonly used chemical synthesis methods. Hie reproducibility and robustness of biotechnological bioconjugate production methods using the recombinant N-OSTs provided herein, is expected to contribute to a reduction of production costs. The homogeneity of especially biotherapeutic conjugate vaccines is generally believed to affect the clinical safety of drug products.

6.12 Analytical Methods for Testing Benefit

Yield

Yield is measured as carbohydrate amount derived from a liter of bacterial production culture grown in a bioreactor under controlled and optimized conditions. After purification of glycoconjugate, the carbohydrate yields can be directly measured by either the anthrone assay, or ELISA using carbohydrate specific antisera. Indirect measurements are possible by using the protein amount (measured by well known BCA, Lowry, or bardford assays) and the glycan length and structure to calculate a theoretical carbohydrate amount per gram of protein. In addition, yield can also be measured by drying the glycoprotein preparation from a volatile buffer and using a balance to measure the weight.

Homogeneity.

Homogeneity means the variability of glycan length and possibly the number of glycosylation sites. Methods listed above can be used for this purpose. SE-HPLC allows the measurement of the hydrodynamic radius. Higher numbers of glycosylation sites in the carrier lead to higher variation in hydrodynamic radius compared to a carrier with less glycosylation sites. However, when single glycan chains are analyzed, they may be more homogenous due to the more controlled length. Glycan length is measured by hydrazinolysis, SDS PAGE, and CGE. In addition, homogeneity can also mean that certain glycosylation site usage patterns change to a broader/narrower range. These factors can be measured by glycopeptide LC-MS/MS.

The invention is further described in the following paragraphs:

1. A recombinant N-oligosaccharyl transferase, wherein the recombinant N-oligosaccharyl transferase (N-OST) can delectably link an oligosaccharide or polysaccharide lacking an N-acetyl sugar at the reducing end to a carrier protein at an N-glycosylation consensus sequence.

2. The method of paragraph 1, wherein the N-OST activity of linking the oligosaccharide or polysaccharide lacking the N-acetyl sugar at the reducing end to the carrier protein at the N-glycosylation sequence is detected by ELISA.

3. The method of paragraph 1 or 2, wherein an ELISA signal indicating the N-OST activity is detectable if it is >2σ or >3σ above an ELISA background signal.

4. The recombinant N-oligosaccharyl transferase of any one of paragraphs 1-3, wherein the carrier protein is a natural carrier protein from the same organism as the N-OST.

5. The recombinant N-oligosaccharyl transferase of any one of paragraphs 1-3, wherein the carrier protein is a heterologous carrier protein from a different organism than the N-OST.

6. The recombinant N-oligosaccharyl transferase of paragraph 5, wherein the carrier protein is selected from the group consisting of exotoxin A of *P. aeruginosa* (EPA), CRM197, diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins.

7. The recombinant N-oligosaccharyl transferase of any one of paragraphs 1 to 6, wherein the carrier protein has at least one glycosylation motif.

8. The recombinant N-oligosaccharyl transferase of paragraph 7, wherein the at least one glycosylation motif comprises D/E-Y-N-X-S/T (X, Y≠P).

9. The recombinant N-oligosaccharyl transferase of paragraph 7, wherein the at least one glycosylation motif comprises Asn-X-Ser(Thr), wherein X can be any amino acid except Pro.

10. The recombinant N-oligosaccharyl transferase of any one of paragraphs 1 to 9, wherein the oligosaccharide or polysaccharide lacking the N-acetyl sugar at the reducing end comprises an antigen.

11. The recombinant N-oligosaccharyl transferase of paragraph 10, wherein the antigen includes an *E. coli* antigen, a *Salmonella* sp antigen, a *Pseudomonas* sp. antigen, a *Klebsiella* sp. antigen, a *acinetobacter* O antigen, a *Chlamydia trachomatis* antigen, a *Vibrio cholera* antigen, a *Listeria* sp. antigen, a *Legionella pneumophila* serotypes 1 to 15 antigen, a *Bordetella parapertussis* antigen, a *Burkholderia mallei* or *pseudomallei* antigen, a *Francisella tularensis* antigen, a *Campylobacter* sp. antigen; a *Clostridium difficile* antigen, *Streptococcus* pyrogenes antigen, a *Streptococcus agalacticae* antigen, a *Neisseria meningitidis* antigen, a *Candida albicans* antigen, a *Haemophilus influenza* antigen, a *Enterococcus faecalis* antigen, a *Borrelia burgdorferi* antigen, a *Neisseria meningitidis* antigen, a *Haemophilus influenza* antigen, a *Leishmania major* antigen, or a *Shigella sonnei*, or *Streptococcus pneumoniae* antigen.

12. The recombinant N-oligosaccharyl transferase of any one of paragraphs 1 to 10, wherein the oligosaccharide or polysaccharide lacking the N-acetyl sugar at the reducing end is a *Staphylococcus aureus* or a *Salmonella enterica* sv. polysaccharide.

13. The recombinant N-oligosaccharyl transferase of paragraph 12, wherein the oligosaccharide or polysaccharide lacking the N-acetyl sugar at the reducing end is a *Staphylococcus aureus* CP5 or a *Salmonella enterica* sv. *Typhimurium* LT2 polysaccharide.

14. The recombinant N-oligosaccharyl transferase of any one of paragraphs 1 to 13, wherein the recombinant N-oligosaccharyl transferase is PglB of *Campylobacter jejuni* (PglB$_{Cj}$) or PglB of *Campylobacter lari* (PglB$_{Cl}$).

15. The recombinant N-oligosaccharyl transferase of any one of the preceding paragraphs, wherein the recombinant N-oligosaccharyl transferase comprises a modification in one or more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of the recombinant N-oligosaccharyl transferase and the N-glycosylated carrier protein.

16. The recombinant N-oligosaccharyl transferase of paragraph 15, wherein the modification in the one or more amino acids is an amino acid substitution.

17. The recombinant N-oligosaccharyl transferase of paragraph 15 or 16, wherein the one or more amino acids include a amino acid that is a non-conserved amino acid in a phylogenetic family of N-oligosaccharyl transferases.

18. The recombinant N-oligosaccharyl transferase of paragraph 17, wherein the non-conserved amino acid is conserved in less than 90%, less than 80%, less than 70%, less than 60%, less than 50%, less than 40%, less than 30%, less than 20% or less than 10% of members of the phylogenetic family of N-oligosaccharyl transferases.

19. The recombinant N-oligosaccharyl transferase of any one of paragraphs 14 to 18, wherein recombinant N-oligosaccharyl transferase comprises modification in two or more amino acids.

20. The recombinant N-oligosaccharyl transferase of any one of paragraphs 14 to 18, wherein recombinant N-oligosaccharyl transferase comprises modification in three or more amino acids.

21. The recombinant N-oligsaccharyl transferase of any one of paragraphs 14 to 18, wherein recombinant N-oligosaccharyl transferase comprises modification in four or more amino acids.

22. The recombinant N-oligosaccharyl transferase of any one of paragraphs 14 to 21, wherein at least one of the one or more amino acids is located in a periplasmatic loop of a transmembrane domain of the recombinant N-oligosaccharyl transferase.

23. The recombinant N-oligosaccharyl transferase of paragraph 22, wherein the periplasmatic loop of tire transmembrane domain is a large external loop 5 (EL5).

24. The recombinant N-oligosaccharyl transferase of paragraph 23, wherein the recombinant N-oligosaccharyl transferase is PglB of *Campylobacter jejuni* (PglB$_{Cj}$) or PglB of *Campylobacter lari* (PglB$_{Cl}$) and the EL5 is EL5 of PglB$_{Cj}$ or of PglB$_{Cl}$.

25. The recombinant N-oligosaccharyl transferase of any one of paragraphs 14 to 24, wherein the recombinant N-oligosaccharyl transferase further comprises a mutation in one or more amino acids in a QLKFYxxR motif.

26. The recombinant N-oligosaccharyl transferase of paragraph 25, wherein the QLKFYxxR motif is a Q287LKFYxxR294 motif.

27. The recombinant N-oligosaccharyl transferase of paragraph 26, wherein the Q287LKFYxxR294 motif is the Q287LKFYxxR294 motif of PglB$_Q$.

28. The recombinant N-oligosaccharyl transferase of any one of paragraphs 14 to 27, wherein the recombinant N-oligosaccharyl transferase is a recombinant PglB$_{Cj}$.

29. The recombinant N-oligosaccharyl transferase of any one of paragraphs 14 to 28, wherein the protein component of the bound N-glycosylated carrier protein is a *C. jejuni* protein.

30. The recombinant N-oligosaccharyl transferase of any one of paragraphs 14 to 28, wherein the protein componend of the bound N-glycosylated carrier protein is selected from the group consisting of exotoxin A of *P. aeruginosa* (EPA), CRM197, diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins.

31. The recombinant N-oligosaccharyl transferase of any one of paragraphs 28 to 30, wherein the oligosaccharide or polysaccharide component of the bound N-glycosylated carrier protein has a galactose monosaccharide at its reducing end.

32. The recombinant N-oligosaccharyl transferase of any one of paragraphs 28 to 31, wherein one or more amino acids selected from the group consisting of Y77, S80, S196, N311, Y462, H479, K482, D483, K522, G476 and G477 of PglB$_{Cj}$ are modified.

33. The recombinant N-oligosaccharyl transferase of paragraph 32, wherein N311 of PglB$_{Cj}$ is modified.

34. The recombinant N-oligosaccharyl transferase of paragraph 33, wherein recombinant PglB$_{Cj}$ comprises a substitution N311V or a substitution N311I.

35. The recombinant N-oligosaccharyl transferase of paragraph 34, wherein the recombinant PglB$_{Cj}$ comprises a substitution N311V.

36. The recombinant N-oligosaccharyl transferase mutant of paragraph 32, wherein the recombinant PglB$_{Cj}$ further comprises a modification in one or more amino acids selected from the group consisting of Y77 and S80.

37. The recombinant N-oligosaccharyl transferase mutant of paragraph 36, wherein the recombinant PglB$_{Cj}$ comprises an amino acid substitution selected from the group consisting of Y77H, Y77T, Y77W, Y77R, Y77K, Y77A, Y77G, S80R and S80H.

38. The recombinant N-oligosaccharyl transferase mutant of paragraph 37, wherein the recombinant PglB$_{Cj}$ comprises an amino acid substitution selected from the group consisting of Y77H and S80R.

39. The recombinant N-oligosaccharyl transferase mutant of any one of paragraphs 28 to 38, wherein the recombinant PglB$_{Cj}$ further comprises an amino acid modification in one or more amino acids of the Q287LKFYxxR294 motif of PglB$_{Cj}$.

40. The recombinant N-oligosaccharyl transferase mutant of paragraph 39, wherein the recombinant PglB$_{Cj}$ comprises an amino acid modification in one or more amino acids selected from the group consisting of Q287, L288, K289 and R294.

41. The recombinant N-oligosaccharyl transferase mutant of paragraph 40, wherein wherein the recombinant PglB$_{Cj}$ comprises one or more amino acid substitutions selected from the group consisting of Q287P, Q287K, Q287R, L288M, L288F, L288I, L288C, K289R, K289N, K289Q and R294K.

42. The recombinant N-oligosaccharyl transferase mutant of any one of paragraphs 28 to 31, wherein the recombinant PglB$_{Cj}$ comprises an amino acid substitution N311V.

43. The recombinant N-oligosaccharyl transferase mutant of any one of paragraphs 28 to 31, wherein the recombinant PglB$_{Cj}$ comprises amino acid substitutions Y77H and N311V.

44. The recombinant N-oligosaccharyl transferase mutant of any one of paragraphs 28 to 31, wherein the recombinant PglB$_{Cj}$ comprises amino acid substitutions S80R and N311V.

45. The recombinant N-oligosaccharyl transferase mutant of any one of paragraphs 28 to 31, wherein the recombinant PglB$_{Cj}$ comprises amino acid substitutions Q287P and Y77H or a Q287P and S80R.

46. The recombinant N-oligosaccharyl transferase mutant of any one of paragraphs paragraph 28 to 31, wherein the recombinant PglB$_{Cj}$ comprises amino acid substitutions S80R, Q287P and N311V.

47. The recombinant N-oligosaccharyl transferase mutant of any one of paragraphs 28 to 31, wherein the recombinant PglB$_{Cj}$ comprises amino acid substitutions Y77H, Q287P and N311V.

48. The recombinant N-oligosaccharyl transferase mutant of any one of paragraphs 28 to 31, wherein the recombinant PglB$_{Cj}$ comprises amino acid substitutions Y77H, S80R, Q287P and N311V.

49. The recombinant N-oligosaccharyl transferase mutant of any one of paragraph 28 to 31, wherein the recombinant PglB$_{Cj}$ comprises amino acid substitutions Y77H, S80R, Q287P, K289R and N311V.

50. Hie recombinant N-oligosaccharyl transferase mutant of paragraph 28, wherein the recombinant PglB$_{Cj}$ comprises amino acid substitutions N311V and A699V.

51. The recombinant N-oligosaccharyl transferase mutant of paragraph 28, wherein the recombinant PglB$_{Cj}$ comprises amino acid substitutions K482R and D483H.

52. The recombinant N-oligosaccharyl transferase of any one of the preceding paragraphs, wherein the recombinant N-oligsaccharyl transferase can increase the yield of in vivo N-glycosylation or in vitro N-glycosylation of the carrier protein with the oligosaccharide or polysaccharide lacking the N-acetyl sugar at the reducing end to a level of more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold above background level in an assay detecting the N-glycosylated carrier protein.

53. The recombinant N-oligosaccharyl transferase of any one of the preceding paragraphs, wherein the recombinant N-oligsaccharyl transferase can increase the rate of in vivo N-glycosylation or in vitro N-glycosylation of the carrier protein with the oligosaccharide or polysaccharide lacking the N-acetyl sugar at the reducing end by more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold compared to a wild-type form of the recombinant N-oligosaccharyl transferase.

54. The recombinant N-oligosaccharyl transferase of any one of the preceding paragraphs, wherein the recombinant N-oligosaccharyl transferase mutant can in vivo or in vitro glycosylate at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% of the carrier protein with the polysaccharide lacking the N-acetyl sugar at the reducing end.

55. A recombinant N-oligosaccharyl transferase (N-OST) comprising a modification in one or more amino acids whose side chains are located within a 2.5-4.0 Å distance from one of the three terminal monosaccharide units at the reducing end of an oligosaccharide or polysaccharide component of a bound N-glycosylated carrier protein in a structural model of a complex of the recombinant N-oligosaccharyl transferase and the N-glycosylated carrier protein.

56. The recombinant N-oligosaccharyl transferase of paragraph 55, wherein the recombinant N-oligosaccharyl transferase is PglB of *Campylobacter jejuni* (PglB$_{Cj}$) or PglB of *Campylobacter lari* (PglB$_{Cl}$)

57. The recombinant N-oligosaccharyl transferase of paragraph 55, wherein the carrier protein is selected from the group consisting of exotoxin A of *P. aeruginosa* (EPA), CRM197, diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, and *C. jejuni* natural glycoproteins.

58. The recombinant N-oligosaccharyl transferase of paragraph 55, wherein the oligosaccharide or polysaccharide component comprises an antigen.

59. The recombinant N-oligosaccharyl transferase of paragraph 58, wherein the antigen includes an *E. coli* antigen, a *Salmonella* sp antigen, a *Pseudomonas* sp. antigen, a *Klebsiella* sp. antigen, a *acinetobacter* O antigen, a *Chlamydia trachomatis* antigen, a *Vibrio cholera* antigen, a *Listeria* sp. antigen, a *Legionella pneumophila* serotypes 1 to 15 antigen, a *Bordetella parapertussis* antigen, a *Burkholderia mallei* or *pseudomallei* antigen, a *Francisella tularensis* antigen, a *Campylobacter* sp. antigen; a *Clostridium difficile* antigen, *Streptococcus* pyrogenes antigen, & *Streptococcus agalacticae* antigen, a *Neisseria meningitidis* antigen, a *Candida albicans* antigen, a *Haemophilus influenza* antigen, a *Enterococcus faecalis* antigen, a *Borrelia burgdorferi* antigen, a *Neisseria meningitidis* antigen, a *Haemophilus influenza* antigen, a *Leishmania major* antigen, or a *Shigella sonnei*, or *Streptococcus pneumoniae* antigen.

60. The recombinant N-oligosaccharyl transferase of any one of paragraphs 55 to 59, wherein the recombinant N-oligosaccharyl transferase comprises modifications in two or more amino acids.

61. The recombinant N-oligosaccharyl transferase of any one of paragraphs 55 to 59, wherein the recombinant N-oligosaccharyl transferase comprises modifications in three or more amino acids.

62. lire recombinant N-oligsaccharyl transferase of any one of paragraphs 55 to 59, wherein the recombinant N-oligosaccharyl transferase comprises modifications in four or more amino acids.

63. The recombinant N-oligosaccharyl transferase of any one of paragraphs 55 to 59, wherein at least one of the one or more amino acids is located in a periplasmatic loop of a transmembrane domain of the recombinant N-oligosaccharyl transferase.

64. The recombinant N-oligosaccharyl transferase of paragraph 63, wherein the periplasmatic loop of the transmembrane domain is a large external loop 5 (EL5).

65. The recombinant N-oligosaccharyl transferase of paragraph 64, wherein the recombinant N-oligosaccharyl transferase is PglB of *Campylobacter jejuni* (PglB$_{Cj}$) and EL5 is EL5 of PglB$_{Cj}$.

66. The recombinant N-oligosaccharyl transferase of any one of paragraphs 55 to 59, wherein the recombinant N-oligosaccharyl transferase further comprises a modification in one or more amino acids in a QLKFYxxR motif.

67. Hie recombinant N-oligosaccharyl transferase of paragraph 66, wherein the recombinant N-oligosaccharyl transferase further comprises a modification in one or more amino acids in a Q287LKFYxxR294 motif.

68. The recombinant N-oligosaccharyl transferase of paragraph 66, wherein the QLKFYxxR motif is the Q287LKFYxxR294 motif of PglB$_{Cj}$.

69. The recombinant N-oligosaccharyl transferase of any one of paragraphs 55 to 68, wherein the modification is an amino acid substitution.

70. The recombinant N-oligosaccharyl transferase of paragraph 69, wherein the amino acid substitution is a substitution of a non-conserved amino acid.

71. The recombinant N-oligosaccharyl transferase of paragraph 55, wherein the bound N-glycosylated polypeptide product is a natural N-glycosylated carrier protein from the same organism as the recombinant N-oligosaccharyl transferase.

72. The recombinant N-oligosaccharyl transferase of paragraph 55, wherein the N-glycosylated carrier protein is a heterologous N-glycosylated carrier protein, wherein the oligosaccharide or polysaccharide component of the N-glycosylated carrier protein is from a different organism than the recombinant N-oligosaccharyl transferase and/or the carrier protein component of the N-glycosylated carrier protein is from a different organism than the recombinant N-oligosaccharyl transferase.

73. The recombinant N-oligosaccharyl transferase of paragraph 55, wherein the recombinant N-oligosaccharyl transferase is a recombinant PglB$_{Cj}$.

74. The recombinant N-oligosaccharyl transferase of paragraph 73, wherein the bound N-glycosylated polypeptide product is a natural *C. jejuni* glycosylated carrier protein.

75. The recombinant N-oligosaccharyl transferase of paragraph 73, wherein the bound N-glycosylated polypeptide product is a heterologous *C. jejuni* glycosylated carrier protein.

76. The recombinant N-oligosaccharyl transferase of paragraph 75, wherein the heterologous *C. jejuni* glycosylated carrier protein is Pseudomonas aeruginosa exotoxin (EPA)-*S. dysenteries* O1 (EPA-O1), EPA-*S. aureus* capsular polysaccharide Type 5 (EPA-CP5) or EPA-*Salmonella enterica* (*S. enterica*) LT2 (EPA-LT2).

77. The recombinant N-oligosaccharyl transferase of paragraph 73, wherein the oligosaccharide or polysaccharide component of the bound N-glycosylated carrier protein does not have an N-acetyl monosaccharide at its reducing end.

78. The recombinant N-oligosaccharyl transferase of paragraph 73, wherein the oligosaccharide or polysaccharide component of the bound N-glycosylated carrier protein has a galactose monosaccharide at its reducing end.

79. The recombinant N-oligosaccharyl transferase of any one of paragraphs 73 to 78, wherein one or more amino acids from the group consisting of Y77, S80, S196, N311, Y462, H479, K482, D483, K522, G476 and G477 of PglB$_{Cj}$ are modified.

80. The recombinant N-oligosaccharyl transferase of paragraph 79, wherein N311 of PglB$_{Cj}$ is modified.

81. The recombinant N-oligosaccharyl transferase of paragraph 79 wherein recombinant PglB$_{Cj}$ comprises an amino acid substitution selected from the group consisting of N311V and N311I.

82. The recombinant N-oligosaccharyl transferase of paragraph 81, wherein recombinant PglB$_{Cj}$ comprises an amino acid substitution N311V.

83. The recombinant N-oligosaccharyl transferase of paragraph 79, wherein one or more amino acids selected from the group consisting of Y77 and S80 of PglB$_{Cj}$ or modified.

84. Hie recombinant N-oligosaccharyl transferase of paragraph 83, wherein the recombinant PglB$_{Cj}$ comprises an amino acid substitution selected from the group consisting of Y77H, Y77T, Y77W, Y77R, Y77K, Y77A, Y77G, S80R and S80H.

85. The recombinant N-oligosaccharyl transferase of paragraph 84, wherein recombinant PglB$_{Cj}$ comprises an amino acid substitution selected from the group consisting of Y77H and S80R.

86. The recombinant N-oligosaccharyl transferase of any one of paragraphs 73-86, wherein the recombinant PglB$_{Cj}$ further comprises a modification of one or more amino acids of the Q287LKFYxxR294 motif of PglB$_{Cj}$.

87. The recombinant N-oligosaccharyl transferase of paragraph 86, wherein the recombinant PglB$_{Cj}$ comprises a modification of one more amino acids selected from the group consisting of Q287, L288 and K289.

88. The recombinant N-oligosaccharyl transferase of paragraph 87, wherein the recombinant PglB$_{Cj}$ comprises a substitution selected from the group consisting of Q287P, Q287K, Q287R, L288M, L288F, L288I, L288C, K289R, K289N, K289Q and R294K.

89. The recombinant N-oligosaccharyl transferase of any one of paragraphs 73-78, wherein the recombinant PglB$_{Cj}$ comprises a substitution N311V.

90. The recombinant N-oligosaccharyl transferase of any one of paragraphs 73-78, wherein the recombinant PglB$_{Cj}$ comprises a substitution Y77H and a substitution N311V.

91. The recombinant N-oligosaccharyl transferase of any one of paragraphs 73-78, wherein the recombinant PglB$_{Cj}$ comprises a substitution S80R and a substitution N311V.

92. The recombinant N-oligosaccharyl transferase of any one of paragraphs 73 to 78, wherein recombinant PglB$_{Cj}$ comprises a substitution Q287P and a substitution Y77H or a substitution Q287P mutation and a substitution S80R.

93. The recombinant N-oligosaccharyl transferase of any one of paragraphs 73-78, wherein the recombinant PglB$_{Cj}$ comprises a substitution S80R, a substitution Q287P and a substitution N311V.

94. The recombinant N-oligosaccharyl transferase of any one of paragraphs 73 to 78, wherein the recombinant PglB$_{Cj}$ comprises a substitution Y77H, a substitution Q287P and a substitution N311V.

95. The recombinant N-oligosaccharyl transferase of any one of paragraphs 73 to 78, wherein the recombinant PglB$_{Cj}$ comprises a substitution Y77H, a substitution S80R, a substitution Q287P and a substitution N311V.

96. The recombinant N-oligosaccharyl transferase of any one of paragraphs 73 to 78, wherein the recombinant PglB$_{Cj}$ comprises a substitution Y77H, a substitution S80R, a substitution Q287P, a substitution K289R and a substitution N311V.

97. The recombinant N-oligosaccharyl transferase of any one of paragraphs 73 to 78, wherein the recombinant PglB$_{Cj}$ comprises a substitution N311V and a substitution A699V.

98. The recombinant N-oligosaccharyl transferase of any one of paragraphs 73 to 78, wherein the recombinant PglB$_{Cj}$ comprises a substitution K482R mutation, and a substitution D483H.

99. The recombinant N-oligosaccharyl transferase of any one paragraphs 55 to 98, wherein the recombinant N-oligosaccharyl transferase can detectably link an oligosaccharide or polysaccharide lacking an N-acetyl sugar at the reducing end to a carrier protein.

100. The recombinant N-oligosaccharyl transferase of any one of paragraphs 99, wherein the recombinant N-oligosaccharyl transferase can detectably link an oligosaccharide or polysaccharide having a galactose monosaccharide at the reducing end to a carrier protein.

101. The recombinant N-oligosaccharyl transferase of paragraph 100, wherein the oligosaccharide or polysaccharide is a *Staphylococcus aureus* or a *Salmonella enterica* sv. oligosaccharide or polysaccharide.

102. The recombinant N-oligosaccharyl transferase of paragraph 100, wherein the oligosaccharide or polysaccharide is a *Staphylococcus aureus* CP5 or a *Salmonella enterica* sv. *Typhimurium* LT2 oligosaccharide or polysaccharide.

103. The recombinant N-oligosaccharyl transferase of any one of paragraphs 55 to 102, wherein the recombinant N-oligsaccharyl transferase can increase the in vivo or in vitro yield of N-glycosylation of a carrier protein with the polysaccharide lacking the N-acetyl sugar at the reducing end to a level of more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold above background level in an assay detecting the N-glycosylated carrier protein.

104. The recombinant N-oligosaccharyl transferase of any one of paragraphs 55 to 102, wherein the recombinant N-oligsaccharyl transferase can increase the in vivo or in vitro yield of N-glycosylation of a carrier protein with a polysaccharide by more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold compared to a wild-type form of the recombinant N-oligosaccharyl transferase.

105. The recombinant N-oligosaccharyl transferase of any one of paragraphs 55 to 102, wherein the recombinant N-oligsaccharyl transferase can yield an in vivo N-glycosylation level or an in vitro glycosylation level of the carrier protein of at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70%.

106. A recombinant N-oligosaccharyl transferase $PglB_{Cj}$ comprising a N311V substitution.

107. A recombinant N-oligosaccharyl transferase $PglB_{Cj}$ comprising a N311V mutation and a Y77H substitution.

108. A recombinant N-oligosaccharyl transferase $PglB_{Cj}$ comprising a N311V mutation and a S80R substitution.

109. A recombinant N-oligosaccharyl transferase $PglB_{Cj}$ comprising a N311V mutation and a Y77H mutation and a S80R substitution.

110. A recombinant N-oligosaccharyl transferase $PglB_{Cj}$ comprising a N311V mutation and a Q287P substitution.

111. A recombinant N-oligosaccharyl transferase $PglB_{Cj}$ comprising a N311V mutation, a Y77H substitution and a Q287P substitution.

112. A recombinant N-oligosaccharyl transferase $PglB_{Cj}$ comprising a N311V mutation, S80R substitution and a Q287P substitution.

113. A recombinant N-oligosaccharyl transferase $PglB_{Cj}$ comprising a N311V substitution, a Y77H substitution, a S80R substitution and a Q287P substitution.

114. A recombinant N-oligosaccharyl transferase $PglB_{Cj}$ comprising a N311V substitution and a A669V substitution.

115. A recombinant N-oligosaccharyl transferase $PglB_{Cj}$ comprising a N311V substitution, a Y77H substitution, a S80R substitution, a Q287P substitution and a K289R substitution.

116. A recombinant N-oligosaccharyl transferase $PglB_{Cj}$ comprising a K482R substitution and a D483H substitution.

117. A recombinant N-oligosaccharyl transferase $PglB_{Cj}$ comprising a N311V substitution and a A669V substitution.

118. A recombinant N-oligosaccharyl transferase $PglB_{Cl}$ (PglB C. lari) comprising a N314V substitution.

119. A recombinant N-oligosaccharyl transferase $PglB_{Cl}$ comprising a N314V mutation and a Y79H substitution.

120. A recombinant N-oligosaccharyl transferase $PglB_{Cl}$ comprising a N314V mutation and a S82R substitution.

121. A recombinant N-oligosaccharyl transferase $PglB_{Cl}$ comprising a N314V mutation and a Y79H mutation and a S82R substitution.

122. A recombinant N-oligosaccharyl transferase $PglB_{Cl}$ comprising a N314V mutation and a Q289P substitution.

123. A recombinant N-oligosaccharyl transferase $PglB_{Cl}$ comprising a N314V mutation, a Y79H substitution and a Q289P substitution.

124. A recombinant N-oligosaccharyl transferase $PglB_{Cl}$ comprising a N314V mutation, S82R substitution and a Q289P substitution.

125. A recombinant N-oligosaccharyl transferase $PglB_{Cl}$ comprising a N314V substitution, a Y79H substitution, a S82R substitution and a Q289P substitution.

126. A recombinant N-oligosaccharyl transferase $PglB_{Cl}$ comprising a K488R substitution and a D489H substitution.

127. A nucleic acid encoding a recombinant N-oligosaccharyl transferase of any one of the paragraphs 1 to 126.

128. A host cell comprising a recombinant N-oligosaccharyl transferase of any one of paragraphs 1 to 127.

129. The host cell of paragraph 128, further comprising a recombinant glycosyltransferase.

130. A host cell comprising a nucleic acid of paragraph 128.

131. The host cell of any one of the preceding paragraphs, wherein the host cell is a prokaryotic cell.

132. The host cell of paragraph 131, wherein the host cell is an E. coli cell.

133. A method of producing a bioconjugate comprising culturing a host cell of any one of the preceding paragraphs in a cell culture medium.

134. The method of paragraph 133, wherein the host cell comprises a carrier protein and a recombinant N-oligosaccharyl transferase.

135. The method of paragraph 134, wherein the host cell further comprises a recombinant glycosyltransferase.

136. The method of paragraph 134, wherein the recombinant N-oligosaccharyl transferase is a recombinant $PglB_{Cj}$.

137. The method of paragraph 134, earner protein is selected from the group consisting of exotoxin A of P. aeruginosa (EPA), CRM197, diphtheria toxoid, tetanus toxoid, detoxified hemolysin A of S. aureus, clumping factor A, clumping factor B, E. coli FimH, E. coli FimHC, E. coli heat labile enterotoxin, detoxified variants of E. coli heat labile enterotoxin, Cholera toxin B subunit (CTB), cholera toxin, detoxified variants of cholera toxin, E. coli sat protein, the passenger domain of E. coli sat protein, C. jejuni AcrA, and C. jejuni natural glycoproteins.

138. The method of paragraph 134, wherein the bioconjugate is an N-glycosylated carrier protein.

139. The method of paragraph 134, wherein the bioconjugate is a natural C. jejuni N-glycosylated carrier protein.

140. The method of paragraph 134, wherein the bioconjugate is a heterologous C. jejuni A-glycosylated carrier protein.

141. The method of paragraph 138, wherein the N-glycosylated carrier protein does not have an N-acetyl sugar at the reducing end of its oligosaccharide or polysaccharide component.

142. The method of paragraph 141, wherein the N-glycosylated carrier protein has a galactose at the reducing end of its oligosaccharide or polysaccharide component.

143. The method of any one of die preceding paragraphs, wherein the recombinant N-oligsaccharyl transferase mutant can increase the rate of bioconjugate production by more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more titan 80-fold, more than 90-fold or more than 100-fold compared to the rate achieved with a wild-type form of the recombinant N-oligosaccharyl transferase.

144. The method of any one of the preceding paragraphs, wherein the recombinant N-oligsaccharyl transferase mutant can increase the yield of bioconjugate production to a level of more than 2-fold, more than 3-fold, more than 4-fold, more than 5-fold, more than 6-fold, more than 7-fold, more than 8-told, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more titan 100-fold above background level in an assay measuring bioconjugate production.

145. The method of any one of the preceding paragraphs, wherein the at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% of carrier protein in a host cell is glycosylated to form the bioconjugate.

146. The method of any one of the preceding paragraphs, further comprising purifying the bioconjugate from the host cell culture.

147. A method of screening a library of recombinant N-oligosaccharyl transferases each recombinant N-oligosaccharyl transferase comprising a modification in one or more amino acids, comprising contacting each member of the library of recombinant N-oligosaccharyl transferases with a carrier protein and an oligosaccharide or polysaccharide lacking an N-acetyl sugar at its reducing end to produce a bioconjugate.

148. The method of paragraph 147, wherein the bioconjugate is an N-glycosylated carrier protein.

149. The method of paragraph 147 or 148, wherein the contacting occurs in vitro.

150. Hie method of any one of paragraphs 147 or 148, wherein the contacting occurs in vivo.

151. The method of paragraph 150, wherein the contacting occurs in a host cell.

152. The method of paragraph 151, wherein the host cell is a prokaryotic cell.

153. The method of paragraph 151, wherein the host cell is an *E. coli* cell.

154. The method of any one of paragraphs 147 to 153, wherein the library of recombinant N-oligosaccharyl transferases comprises at least 2, at least 5, at least 10, at least 15, at least 20, at least 25, at least 50, at least 75, at least 100, at least 150, at least 200, at least 250, at least 500, at least 750 or at least 1,000 recombinant N-oligosaccharyl transferases.

155. The method of paragraph 147, wherein the library of recombinant N-oligosaccharide transferases comprises one or more recombinant N-oligosaccharide transferases of any one of paragraphs 1 to 97.

156. The method of paragraph 147, further comprising selecting one or more recombinant N-oligosaccharyl transferases from the library of recombinant N-oligosaccharyl transferases.

157. The method of paragraph 156, wherein the one or more recombinant N-oligosaccharyl transferase is selected if the recombinant N-oligosaccharyl transferase yields the bioconjugate at a rate that is more than 2-fold, mote than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more than 20-fold, more than 25-fold, more than 30-fold, more than 35-fold, more than 40-fold, more than 45-fold, more than 50-fold, more than 60-fold, more than 70-fold, more than 80-fold, more than 90-fold or more than 100-fold faster than the rate of a wild-type form of tire recombinant N-oligosaccharyl transferase.

158. Hie method of paragraph 156, wherein the one or more N-oligosaccharyl transferase mutant is selected if the N-oligosaccharyl transferase mutant yields the bioconjugate at a level of more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 13-fold, more than 14-fold, more than 15-fold, more than 17-fold, more titan 20-fold, more than 25-fold, more than 30-fold, more than 35-fold, more titan 40-fold, more than 45-fold, more than 50-fold, more than 60-fold, more than 70-fold, more than 80-fold, more than 90-fold or more than 100-fold above background level in an assay detecting the bioconjugate.

159. The method of paragraph 156, the one or more recombinant N-oligosaccharyl transferase is selected if the recombinant N-oligosaccharyl transferase glycosylates at least 1%, at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% of a carrier protein in the host cell.

160. The method of any one of paragraphs 133 to 159, further comprising analyzing the rate or yield of production of the bioconjugate.

161. A method of identifying a recombinant N-oligosaccharyl transferase having a modified substrate specificity relative to a wild-type form of the N-oligosaccharyl transferase, comprising modifying one or more amino acids whose side chains are located within a 2.5-4.0 Å distance from one of the three terminal monosaccharide units at the reducing end of the oligosaccharide or polysaccharide component of a bound N-glycosylated carrier protein in a structural model of a complex of the recombinant N-oligosaccharyl transferase and the N-glycosylated carrier protein.

162. The method of paragraph 161, comprising modifying two or more amino acids of the recombinant N-oligosaccharyl transferase.

163. The method of paragraph 161, comprising modifying three or more amino acids of the recombinant N-oligosaccharyl transferase.

164. The method of paragraph 161, comprising modifying four or more amino acids of the recombinant N-oligosaccharyl transferase.

165. The method of paragraph 161, wherein at least one of the one or more amino acids is located in a periplasmatic loop of a transmembrane domain of the recombinant N-oligosaccharyl transferase.

166. The method of paragraph 165, wherein the periplasmatic loop of the transmembrane domain is a large external loop 5 (EL5).

167. The method of paragraph 161 to 166, further comprising mutating one or more amino acids in a QLKFYxxR motif of the recombinant N-oligosaccharyl transferase.

168. The method of paragraph 167, wherein the QLKFYxxR motif is a Q287LKFYxxR294 motif.

169. The method of any one of paragraphs 161 to 168, wherein the bound N-glycosylated carrier protein is a natural N-glycosylated carrier protein.

170. The method of any one of paragraphs 161 to 168, wherein the bound N-glycosylated carrier protein is a heterologous N-glycosylated carrier protein.

171. The method of paragraph 161, wherein the recombinant N-oligosaccharyl transferase a recombinant $PglB_{Cj}$.

172. The method of paragraph 171, wherein the bound N-glycosylated carrier protein is a natural C. jejuni N-glycosylated carrier protein.

173. The method of paragraph 171, wherein the bound N-glycosylated carrier protein is a heterologous C. jejuni N-glycosylated carrier protein.

174. The method of paragraph 171, wherein the oligosaccharide or polysaccharide component of the bound N-glycosylated carrier protein does not have an N-acetyl monosaccharide at its reducing end.

175. The method of paragraph 171, wherein the oligosaccharide or polysaccharide component of the bound N-glycosylated carrier protein has a galactose monosaccharide at its reducing end.

176. The method of any one of the preceding paragraphs, wherein the recombinant N-oligosaccharyl transferase has a modified substrate selectivity in vitro.

177. The method of any one of the preceding paragraphs, wherein the recombinant N-oligosaccharyl transferase has a modified substrate selectivity in vivo.

7. EXAMPLES

7.1 Example 1: Modeling of $PglB_{Cj}$ and In Silico Oligosaccharide Binding A set of homology models of C. jejuni PglB was generated using different homology modelling methods with the experimental C. lari structure as template (PDBid 3RCE). The model generated with the HHpredB method (Söding J, Biegert A, Lupas A N. The HHpred interactive server for protein homology detection and structure prediction. Nucleic Acids Res. 2005:33, W244-8.) was selected because its coordinates was better scored by the QMEAN model quality estimation tool (Benkert P, Biasini M, Schwede T. Toward the estimation of the absolute quality of individual protein structure models. Bioinformatics. 2011:27:343-350). Next, the $Mg^{2+}$ ion and the acceptor peptide were transferred from the C. lari structure (PDBid 3RCE). To visualize the orientation of the protein in the cytoplasmic membrane, a phospholipid bilayer model was derived according to the OPM database entry for C. lari (Lomize M A, Pogozheva I D, Joo H, Mosberg H I, Lomize A L. OPM database and PPM web server: resources for positioning of proteins in membranes. Nucleic Acids Res. 2012 40: D370-6). The natural heptasaccharide ligand of C. jejuni and the first repeating unit of the S. enterica LT2 polysaccharides were parameterized accounting for charges and tautomers, and low energy conformations generated. (Shelley J C, Cholleti A, Frye L L, Greenwood J R, Timlin M R, Uchimaya M: J Comput Aided Mol Des. 2007, (12):681-91). These low energy conformations were then placed into the model, and conformationally sampled (Kolossvdry, I.; Guida, W. C. Low-mode Conformational Search Elucidated. Application to C39H80 and Flexible Docking of 9-Deazaguanine Inhibitors to PNP. J. Comput. Chem. 1999, 20, 1671.) The saccharide was defined as freely moving substructure and position constraints have been placed on all protein backbone atoms and on all atoms in a 6 Å radius around the OS. Distance constraints on the CO—N and the N—C1 bond between the first saccharide unit and the ASP-N were applied. A conformational sampling for 1000 steps was set up applying OPLS (Kaminski, G. A.; Friesner, R. A.; Tirado-Rives, J.; Jorgensen, W. J. J. Phys. Chem. B 2001, 105, 6474).), including a full atom water model and a 35 $kcalmol^{-1}$ window to screen possible conformations, which were refined with a similar protocol employing a more narrow energy window of 21 $kJmol^{-1}$.

The selection of potential oligosaccharide interacting residues of $PglB_{Cj}$ as targets for mutagenesis required the generation of a homology model which was generated using the experimentally solved structure of C. lari PglB (PDBid 3RCE) as template. Binding of the natural C. jejuni N-glycan substrate and of the first repeating unit of the heterologous S. enterica LT2 polysaccharide to $PglB_{Cj}$ was simulated. The monosaccharide subunit composition of the native oligosaccharide substrate and of the repeating units of two heterologous polysaccharides analysed in this study are shown in FIG. 1. The oligosaccharide structures were conformationally sampled while being covalently attached to the amide nitrogen of the asparagine residue within the acceptor peptide. The conformation of the enzyme and hence the ligand were assumed to be product-like, i.e., just before the release from the active site. The structural models therefore do not consider any of the factors for initial binding of the undecaprenyl-pyrophosphate linked oligosaccharide (OS) substrate. In FIG. 2A, examples of predicted conformations are shown for C. jejuni OS and the first repeating unit of S. enterica LT2. The overall interactions with the protein residues and the relative orientation in the binding site differed substantially between the two oligosaccharides. Snapshots of thermodynamically favored conformations are shown in FIGS. 2B and 2C. While the natural OS substrate offered a multitude of hydrogen bonding partners to itself and to the surrounding residues of wild-type $PglB_{Cj}$, the LT2 O antigen repeating unit was lacking similar interactions, supporting a mechanistic model in which low transfer efficiency is caused by poor binding of the carbohydrate substrate to the active site. The repeating unit of the LT2 O antigen is composed of four hexoses (FIG. 1) which lack N-acetyl substituents, limiting the possibilities for hydrogen bond formation.

To select mutagenesis positions within the $PglB_{WT}$ sequence, the generated model was used to identify amino acid side chains that are located in 2.5-4 Å distance to the natural C. jejuni N-glycan. The following residues matched this criterion: Y77, S80, S196, N311, Y462, H479 and K522 (FIG. 2B). In the case of G476 and G477, the carbonyl oxygen atom of the polypeptide backbone was predicted to be in close distance to the innermost sugar (FIG. 2B).

7.2 Example 2: Mutagenesis of Predicted Sugar-Interacting Residues

Bacterial strains and plasmids used in this study are described in Table 2. *E. coli* W3110 waaL was used as host strain for production of EPA-*C. jejuni* OS and EPA-*Shigella* O1 glycoconjugates, and EPA-CP5 in in vivo glycosylation experiments. *S. enterica* sv. *Typhimurium* SGSC228 which produces LT2 polysaccharides and lacks a functional waaL gene was used for production of LT2-EPA. Ultra competent *E. coli* cells were used for initial transformation of constructed plasmid libraries and variants. *E. coli* DH5α was used as standard host for plasmid production and storage.

(pGVNX1049), followed by insertion of a TAA stop codon in front of the sequence encoding the HA peptide tag by QuikChange (pGVNX1050). A size-reduced pACT3 Kan derived template plasmid pGVXN1413 which lacks the lad repressor gene (semi-constitutive expression of PglB) was constructed by ligation of a KpnI-BamHI fragment of pGVXN1050 (encoding wild-type PglB) into the BamHI-KpnI vector backbone fragment of pGVXN1415. Size reduced template plasmid pGVXN1418 (PglB N311V) for second round libraries was constructed by ligation of an AscI-BamHI fragment of pGVXN1050 (last third of wt pglB gene) into a BamHI-AscI fragment of pGVXN1415. All plasmids were validated by DNA sequencing.

TABLE 2

Strains and Plasmids

| Strain/plasmid | Description | Selection marker | Reference |
|---|---|---|---|
| Bacterial strains | | | |
| *E. coli* XL10-Gold | Tet$^R$ Δ(mcrA)183 Δ(mcrCB-hsdSMR-mrr)173 endA1 supE44 thi-1 recA1 gyrA96 relA1 lac Hte [F' proAB lacIqZΔM15 Tn10 (Tet$^R$) Amy Cam$^R$] | Cm$^R$ | Stratagene |
| *E. coli* DH5α | K-12 φ80dlacZΔM15 endA1 recA1 hsdR17(rK − mK+) supE44 thi-1 gyrA96 relA1 Δ(lacZYA-argF)U169 F− | — | Clontech |
| *E. coli* CLM24 | W3110 ΔwaaL | — | (4) |
| *E. coli* StGVXN1717 | W3110 ΔwaaL ΔwecA-wzzE ΔrmlB-wecG::cat | Cm$^R$ | (7) |
| *S. enterica* SGSC228 | sv. Typhimurium LT2; waaL446 | — | (5) |
| Plasmids | | | |
| pACT3Kan | Medium copy number vector for IPTG-inducible expression; lacI, P$_{tac}$, ori: pACYC184/p15a | Kan$^R$ | (11) |
| pEXT21 | Low copy number vector for IPTG-inducible expression; lacI, P$_{tac}$, ori: IncW | Sp$^R$ | (47) |
| pACYC(pgl$_{mut}$) | *C. jejuni* heptasaccharides, constitutive expression; pgl operon of *C. jejuni* with inactive PglB variant W458A-D459A (PglB$_{mut}$), ori: pACYC184/p15a | Cm$^R$ | (2) |
| pGVXN64 | *Shigella dysenteriae* O1 LPS polysaccharides, constitutive expression; ori: IncPα | Tet$^R$ | (8) |
| pGVXN115 | PglB$_{mut}$, IPTG inducible expression; pEXT21 vector (ori: IncW) | Sp$^R$ | (8) |
| pGVXN150 | *Pseudomonas aeruginosa* exotoxoid A (EPA) with 2 engineered N-glycosylation sites, L-arabinose inducible expression; N-terminal ssDsbA signal peptide for secretion to periplasm and C-terminal 6H tag, ori: pBR322 | Amp$^R$ | (7) |
| pGVXN393 | *Staphyloccus aureus* CP5 capsular polysaccharides, constitutive expression; ori: IncPα | Tet$^R$ | (7) |
| pGVXN408 | Inactive *C. jejuni* PglB-HA W458A-D459A (PglB$_{mut}$), IPTG inducible expression; pACT3Kan vector | Kan$^R$ | (11) |
| pGVXN925 | *C. jejuni* PglB with C-terminal hemagglutinin (HA) tag, codon-optimized for *E. coli*; high copy number cloning vector pUC57 | Amp$^R$ | This study |
| pGVXN970 | wild-type, untagged PglB$_{Cj}$, codon-optimized for *E. coli*, IPTG inducible expression; pEXT21 vector | Sp$^R$ | This study |
| pGVXN1049 | *C. jejuni* PglB-HA, codon-optimized for *E. coli*, IPTG inducible expression; pACT3Kan vector | Kan$^R$ | This study |
| pGVXN1050 | wild-type, untagged PglB$_{Cj}$, codon-optimized for *E. coli*, IPTG inducible expression; pACT3Kan vector | Kan$^R$ | This study |
| pGVXN1217 | PglB$_{Cj}$ N311V, derivative of pGVXN970 | Sp$^R$ | This study |
| pGVXN1413 | wild-type PglB$_{Cj}$, semi-constitutive expression; size-reduced pACT3Kan vector without lacI | Kan$^R$ | This study |
| pGVXN1415 | PglB$_{Cj}$ N311V-A669V, semi-constitutive expression; size-reduced pACT3Kan vector without lacI, isolated from a saturation mutagenesis library of pGVXN1050 | Kan$^R$ | Ihssen et al., in preparation |
| pGVXN1418 | PglB$_{Cj}$ N311V, derivative of pGVXN1415 | Kan$^R$ | This study |
| pGVXN1942 | PglB$_{Cj}$ S80R-Q287P-N311V, isolated from a shuffled library, derivative of pGVXN1418 | Kan$^R$ | This study |

Codon optimized PglB was expressed from low copy plasmid pEXT21 and obtained from a gene synthesis service company (Genescript). A template plasmid for construction of pglB libraries was constructed by PCR-subcloning of codon-optimized pglB-HA from pGVXN925 into pACD-Kan, using restriction sites KprtI and BamHI Appropriate antibiotics were added to all growth media to ensure plasmid maintenance (Ampicillin, Amp: 100 mg L$^{-1}$, Chloramphenicol, Cm: 10 mg L$^{-1}$, Kanamycin, Kan: 30 mg L$^{-1}$, Spectimomycin, Sp: 80 mg L$^{-1}$, Tetracyclin, Tet: 20 mg L$^{-1}$).

Mutagenic primers and sequencing services were obtained from Microsynth (Balgach, Switzerland). PglB variants and libraries were constructed by QuikChange using pGVXN1050, pGVXN1415 or pGVXN1418 as template. Desired mutations were verified by sequencing.

Only sequences of forward primers of each primer pair is given, respective reverse complement sequences were used for the reverse primers. Degenerate codons at mutated positions) are underlined. Saturation mutagenesis of N311: 5'-GC TTC ATG TAC TTC AAC GTT NNK CAG ACG ATC CAA GAA GTG G-3' (SEQ ID NO:3), saturation mutagenesis of Y77:5'-CAT CAG CCG AAC GAT CTG AGT NNK TAC GGT AGC TCT CTG TCC G-3'(SEQ ID NO:4), four amino acid (Ala, Ser, Cys, Gly) randomization of G476-G477 5'-C GAT GTT AAA ACG CTG GTC GAC KST AAA CAC CTG GGC AAG G-3' (SEQ ID NO:5), saturation mutagenesis of S80 5'-CG AAC GAT CTG AGT TAT TAC GGT NNK TCT CTG TCC GCG CTG ACC-3' (SEQ ID NO:6), saturation mutagenesis of Q287 5'-GGT GTT GAT CCG ATT CTG TAC NNK CTG AAA TTT TAT ATC TTC CGC TCA G-3' (SEQ ID NO:7), saturation mutagenesis of L288 5'-GTT GAT CCG ATT CTG TAC CAG NNK AAA TTT TAT ATC TTC CGC TCA GAT G-3' (SEQ ID NO:8), saturation mutagenesis of K289 5'-GAT CCG ATT CTG TAC CAG CTG NNK TTT TAT ATC TTC CGC TCA GAT GAA TCG-3' (SEQ ID NO:9), saturation mutagenesis of F290 5'-CCG ATT CTG TAC CAG CTG AAA NNK TAT ATC TTC CGC TCA GAT GAA TCG-3' (SEQ ID NO: 10), saturation mutagenesis of Y291 5'-CG ATT CTG TAC CAG CTG AAA TTT NNK ATC TTC CGC TCA GAT GAA TCG-3' (SEQ ID NO: 11), saturation mutagenesis of R294 5'-G TAC CAG CTG AAA TTT TAT ATC TTC NNK TCA GAT GAA TCG GCA AAC CTG-3' (SEQ ID NO: 12). First round libraries were constructed using wild-type PglB plasmids pGVXN1050 or pGVXN1413 as template. Second round libraries were constructed using pGVXN1418 (PglB N311V) or pGVXN1930 (PglB-HA N311V) as template. Initial mutant libraries were based on pGVXN1050 as template plasmid. However, it was found that such libraries repeatedly yielded variant plasmids with a 2.1 kB reduced vector backbone due to a recombination event at a repetitive sequence present in the original pACT3 sequence. The size reduction lead to loss of the loci repressor gene, which in turn facilitated semi-constitutive expression of PglB and a two-fold increase in EPA-CP5 levels (published elsewhere). In order to avoid such unwanted recombination, pGVXN1413, pGVXN1418 and pGVXN1930 were used as template in later libraries.

A shuffled library of neutral and slightly beneficial second round variants was constructed with the Multi Site-Directed Mutagenesis kit according to the manufacturer's instructions (Stratagene). A mix of three oligonucleotides was used, primer 5'-CAT CAG CCG AAC GAT CTG AGT YMT TAC GGT MGT TCT CTG TCC GCG CTG AC-3' (SEQ ID NO: 13) targeting the Y77 region and a 4:1 molar ratio mix of primers 5'-C GGT GTT GAT CCG ATT CTG TAC MVG WTK MAK TTT TAT ATC TTC CGC TCA GAT GAA TCG-3' and 5'-C GGT GTT GAT CCG ATT CTG TAC MVG WTK CGT TTT TAT ATC TTC CGC TCA GAT GAA TCG-3' (SEQ ID NO: 14) targeting the EL5 region. Improved PglB variant N311V (pGVXN1418) was used as template.

Only libraries with less than 20% of wild-type clones were used for screening. Plasmid libraries were produced by resuspending at least 1000 XL10-Gold colonies (5000 colonies for the shuffled library) in phosphate buffered saline (PBS), followed by plasmid purification with a standard mini-prep kit. Plasmid libraries were transformed into E. coli and S. enterica expression strains using standard electroporation procedures.

Mutant libraries and individual variant plasmids were screened in 96-deep well plates as described previously, except that the concentration of IPTG added at induction was reduced to 30 µM in order to reduce inclusion body formation. PglB variant plasmids were isolated from expression strains by retransformation of plasmid preps in chemically competent E. coli DH5a and selection for Kanamycin resistance only. Mutations were characterized by Sanger sequencing of purified plasmids, employing two overlapping reads. Chemically or electrocompetent S. enteria SGSG228 (pGVXN150), E. coli St1717 (pGVXN150, pGVXN393), and E. coli W3110 waaL (pGVXN64, pGVXN150) were used as host strains for LT2-EPA, CP5-EPA and O1-EPA DWP-ELISA screenings, respectively.

Host strains for EPA-CP5, EPA-LT2 and EPA-O1 production in shake flask experiments were similar to DWP experiments. E. coli W3110 waaL (pACYC(pgl$_{mut}$), pGVXN150) was used as host strain for EPA-Cj OS production. The kinetics of glycoprotein formation were recorded by preparing biomass-normalized periplasmic protein extracts at regular intervals after induction, followed by sandwich ELISA. Triplicate preculture tubes with LB medium (5 g L$^{-1}$ yeast extract, 10 g L$^{-1}$ and 5 g L$^{-1}$ NaCl) were inoculated with individual single colonies from fresh streak-out or transformation plates and incubated overnight at 37° C. and 160 rpm. Triplicate Erlenmeyer flasks with 50% v/v of LB-M9 medium (5 g L$^{-1}$ yeast extract, 10 g L$^{-1}$ tryptone, 12.8 g L$^{-1}$ Na$_2$HPO$_4$.7H$_2$O, 3.0 g L$^{-1}$ KH$_2$PO$_4$, 0.5 g L$^{-1}$ NaCl, 1.0 g L$^{-1}$ NH$_4$Cl, 2 mM MgSO$_4$.7H$_2$O and 0.1 mM CaCl$_2$) were inoculated 1:50 from tube pre-cultures and incubated at 37° C. and 160 rpm. At an OD$_{600}$ of 0.5, 1 mM IPTG and 4 g L$^{-1}$ L-arabinose were added for induction and stirrer speed was reduced to 100 rpm. In the case of the Salmonella host strain, EPA/EPA-LT2 degradation was observed in LB-M9 shake flasks cultures after overnight induction. Degradation could be prevented by using a high strength complex medium (2YT, 10 g L$^{-1}$ yeast extract, 14 g L$^{-1}$ tryptone, M9 salts), reducing OD$_{600}$ at induction to 0.3-0.4 and switching to static incubation (fully anaerobic growth) after induction.

Periplasmic extracts were prepared. Extracts were diluted 1000-to 20'000-fold in PBS with 1% w/v dry milk and analysed by sandwich ELISA. Only dilutions yielding non-saturated ELISA signals (Absorbance at 450 nm below 1.0) were used for data analysis. For purification of hexahistidine-tagged proteins, periplasmic extracts of triplicate overnight shake flask cultures were pooled and Ni-affinity chromatography was performed according to standard protocols using HiTrap FF columns (GE Healthcare). SDS-PAGE and Coomassie staining were carried out using standard methods. The relative combined intensity of EPA-LT2 glycoforms was quantified with the software ImageJ (imagej.nih.gov).

Extracts of periplasmic proteins were diluted appropriately and analysed by sandwich ELISA in 96-well plates. The capture antibody for all ELISA analyses was protein G purified goat-anti EPA antiserum. Rabbit anti-S. aureus CP5, rabbit anti Salmonella O:5/O:4 (Staten Serum Institute, Denmark), rabbit anti-Shigella O1 and rabbit anti-C. jejuni were used for detection of EPA-linked oligo- and polysaccharides. Horseradish peroxidase (HRP) coupled goat anti-rabbit IgG (Bio-Rad, Reinach, Switzerland) and Ultra-TMB substrate (Thermo-Scientific/Pierce) were used for ELISA development. The HRP reaction was stopped by addition of 2M H$_2$SO$_4$ and absorbance at 450 nm (ELISA signal) was measured against air with a plate reader. Appropriate development times were chosen so that signal saturation could be avoided (maximal abs. 450 nm≤1.0). Signals were background-corrected by subtracting average absorbance values of samples derived from isogenic control strains expressing PglB$_{mut}$. Western blot analysis of periplasmic and total cell proteins was performed as described previously. EPA and PglB-HA were detected by rabbit anti-EPA (Sigma-Aldrich, Buchs, Switzerland) and rabbit anti HA (Sigma-Aldrich) primary antibodies, respectively. Oligo- and polysaccharides conjugated to EPA were detected with the same antibodies as used for ELISA.

In the PglB$_{Cj}$ model with *C. jejuni* OS the amide group of N311 formed a direct hydrogen bond with the C6 hydroxyl group of the second monosaccharide, i.e., GalNAc (counted from the reducing end) (FIG. 2A). A pglB plasmid where N311 was randomly changed to all other 19 amino acids was transformed into a *Salmonella* strain expressing LT2 polysaccharides and a non-toxic form of *Pseudomonas aeruginosa* exotoxin (EPA). Screening in a 96 well plate using glycoprotein specific ELISA yielded three clones that showed significantly improved glycosylation efficiency compared to wild-type PglB (FIG. 3A). In all of them, residue N311 was mutated to valine (codons: 2×GTT, 1×GTG).

The same library was then transformed into *E. coli* cells expressing the *S. aureus* capsular polysaccharide Type 5 (CP5) and EPA. Seven clones were identified that showed an improved glycosylation efficiency compared to wild-type PglB by measuring CP5-EPA productivity by ELISA (FIG. 3B). Six of them harbored the amino acid substitution N311V (codons GTG and GTT) and one exhibited mutation N311I (codon ATT). The high fraction of active clones (≈80%) indicates that N311 is highly mutation tolerant, which is in agreement with considerable variability at this position in homologous N-OST sequences (FIG. 4).

Another amino acid localized in close proximity to the oligosaccharide binding site was mutagenized as above. Y77 resides in a periplasmic loop of the transmembrane domain and may interact with oligosaccharides via water mediated and direct hydrogen bonds according to our model (FIG. 2A). The residue was found to be highly mutation-tolerant (80-90% CP5-EPA producing clones in a saturation mutagenesis library); again corresponding to a high degree of variability in homologous protein sequences (FIG. 4). Only neutral amino acid substitutions (Y77L, Y77F) were found, but no improved variants were identified.

Residues Y462, G476, G477 and H479 were also modeled to be in close distance to bound natural oligosaccharide in the PglB$_{Cj}$ model (FIG. 2A); however, they are highly conserved in bacterial N-OST. In spite of restricting changes to naturally occurring amino acid substitutions, CP5-EPA glycoconjugate signals were reduced by 50-90% in Y462, G476, G477 and H479 PglB$_{Cj}$ variants, with the notable exception of G476P and H479N which were found to be neutral mutations (FIG. 5). Random combinations of the small amino acids alanine, serine, cysteine and glycine at G476-G477 all led to reduced or abolished CP5-EPA production.

In summary, from this first round of mutagenesis of amino acids in close proximity of the oligosaccharide binding site of PglB, N311 was identified as the position with the highest impact on improving glycosylation yields. In addition, Y77 was also identified as mutation tolerant.

7.3 Example 3: Effect of N311V on Glycoprotein Formation Rates

The effect of PglB$_{Cj}$ variant N311V on in vivo glycosylation rates for different oligo-/polysaccharide substrates was analysed in shake flask culture (FIG. 6). PglB$_{Cj}$ N311V and PglBwt were expressed from a low copy number vector. Cells expressing the mutant N-OST yielded 8-fold more LT2-EPA after overnight induction (FIG. 6A). The improvement factors after 2 h and 4 h of induction were 22- and 11-fold, respectively. The initial rate of CP5-EPA formation was increased by a factor of 5.1 (FIG. 6B). Initial rates of O1-EPA formation were also increased two-fold in mutant N311V (FIG. 6C), although this polysaccharide substrate was not used in library screenings. By contrast, no significant effect was found for in vivo glycosylation of EPA with the natural *C. jejuni* OS substrate of PglB. The increase in ELISA signals over time and the beneficial or neutral effect of N311V corresponded to Western blot results for exemplary periplasmic protein samples (FIG. 7).

To analyze the cause of the beneficial effect of N311V production we constructed wild-type PglB and PglB N311V variants with a C-terminal hemagglutinin (HA) peptide tag. *Ibis* allowed us to follow expression levels of PglB during the experiments. PglB-HA specific bands in biomass-normalized whole cell protein samples originating from mutants were less intense and more variable than those from wild-type PglB (FIG. 8A). Degradation products corresponding in size to the C-terminal periplasmic domain appeared after induction, indicating a destabilizing effect of the mutation. In spite of the apparent negative effect on PglB stability, EPA-CP5 production followed by ELISA was again significantly increased in cells expressing PglB$_{Cj}$ N311V (FIG. 8B).

7.4 Example 4: Further Rounds of Mutagenesis and Screening

Following the principle of iterative saturation mutagenesis, PglBCj N311V was used as template for randomization of Y77 and S80. The latter residue also varies between PglB homologues (FIG. 4) and faces the modeled oligosaccharide substrate binding site just above the position where the external loop EL1 protrudes from the membrane (FIG. 2A-2C). Both Y77 and S80 were found to be highly mutation tolerant, with 70-80% active clones when screened for LT2-EPA production (Table 2). The ten clones with the highest ELISA signals were sequenced, and Y77 was changed to diverse amino acids, with a bias towards residues with basic side chains (Table 3). In the NNK library randomizing S80, variant S80R was dominating in the top-performing clones (Table 3).

TABLE 3

Mutation tolerance of PglB$_{Cj}$ residues mutated in second round saturation mutagenesis libraries and amino acid substitutions identified in the 10 clones with the highest LT2-EPA ELISA signals. Clones were counted as active when background-corrected ELISA signals reached more than 10% of the average value of N311V control wells.

| PglB$_{Cj}$ residue | Fraction of active clones in NNK library | Mutations identified in top 10 clones |
|---|---|---|
| Y77 | 86% | Y77H (2×) Y77T Y77W |

TABLE 3-continued

Mutation tolerance of PglB$_{Cj}$ residues mutated in second round saturation mutagenesis libraries and amino acid substitutions identified in the 10 clones with the highest LT2-EPA ELISA signals. Clones were counted as active when background-corrected ELISA signals reached more than 10% of the average value of N311V control wells.

| PglB$_{Cj}$ residue | Fraction of active clones in NNK library | Mutations identified in top 10 clones |
|---|---|---|
| | | Y77R |
| | | Y77K (2×) |
| | | Y77A |
| | | Y77G |
| S80 | 81% | S80R (8×) |
| | | S80H |
| Q287 | 65% | Q287P (4×) |
| | | Q287K (2×) |
| | | Q287R |
| L288 | 61% | L288M (2×) |
| | | L288F |
| | | L288I |
| | | L288I |
| K289 | 78% | K289R (4×) |
| | | K289N (2×) |
| | | K289Q (2×) |
| F290 | 16% | none (all wt) |
| Y291 | 3.9% | none (all wt) |
| R294 | 22% | R294K |

The PglBCj Q287LKFYxxR294 motif within the N-terminal part of EL5 is highly conserved in PglB sequences of *Campylobacter* species, but not in N-OST of more distantly related species (FIG. 9A-9C). Due to the observation that the innermost two sugar subunits of N-linked glycans of *Campylobacter* species are similar (1st 2,4-diacetamido-2, 4,6-trideoxyhexose, 2nd N-acetyl-hexosamine), it was hypothesized residues of the *Campylobacter*-specific Q287LKFYxxR294 motif may influence oligosaccharide specificity. Saturation mutagenesis libraries were generated at these positions with improved variant N311V as template. When screened in the host strain for LT2-EPA production, a clear difference was observed for the first and second part of the motif (Table 3). While saturation mutagenesis of Q287, L288 and K289 yielded 60-80% active clones, the adjacent residues F290, Y291 and R294 were highly mutation-sensitive. The 10 top performing clones of the Q287, L288 and K289 libraries exhibited non-random amino acid substitutions (Table 3). Proline and the positively charged amino acids lysine and arginine were overrepresented at position Q287. At L288 alternative hydrophobic residues (M, I, F or C) were found exclusively. A bias for residues with either amide (Q, N) or positively charged side chains (R) was observed at position K289 (Table 3). In a final step, the neutral and slightly beneficial mutations found for residues Y77, S80, Q287, L288 and K289 were shuffled. When 720 clones of this library were screened for LT2-EPA production, numerous positive outliers were identified, of which an example is given in FIG. 10A. Clones with at least 2.5-fold increased ELISA signals compared to the average signal of template control clones on the same plate were sequenced (n=14). S80R was detected in 79% (n=11), Q287P in 43% (n=6) and Y77H in 29% (n=4) of these clones, respectively. The double mutants Y77H-N311V and S80R-N311V were found two and four times, respectively. Q287P occurred only in combination with either Y77H or S80R. Y77S, L288I, L288F, K289R and K289Q were found once or twice in combination with the more frequently observed mutations, indicating that these amino acid substitutions were neutral.

Representative improved variant plasmids were retransformed into the EPA-LT2 expression strain and rescreened in triplicate D WP minicultures (FIG. 10B). A significant additive beneficial effect was verified for both Y77H (2.1-fold to N311V) and S80R (1.8-fold to N311V). When combined with S80R-N311V, Q287P lead to a further increase in EPA-LT2 ELISA signals by a factor of 1.7, resulting in a total improvement factor of 15 relative to wild-type PglB in overnight induced DWP cultures (FIG. 10B). The additive improvement of EPA-LT2 formation was also observed when Ni-NTA affinity chromatography purified material from shake flask cultures was analyzed by SDS-PAGE and Western blot (FIG. 10C). Glycoforms hybridized with antibodies specific for *Salmonella* serotypes O:4 and O:5, detecting the branching abequose sugar within the LT2 polysaccharide and its O-acetylated form, respectively. Using image quantification software, the combined intensity of glycoform bands (>80 kDa) was increased by factors of 9 and 16 for $PglB_{Cj}$ variants N311V and S80R-Q287P-N311V, respectively.

In conclusion, it has been demonstrated that recombinant N-OSTs with modified substrate specificities were successfully identified. Specifically, N-OSTs were identified that can conjugate carrier proteins with oligosaccharides or polysaccharides lacking N-acetyl groups in the monosaccharide unit at the non-reducing ends of the oligosaccharides or polysaccharides. Advantageously, the identified N-OSTs comprise certain amino acid substitutions and allow for the production of medically relevant glycovaccine at increased rates and with increased yields compared to wild-type N-OSTs.

7.5 Example 5: Mutagenesis of PglB *C. jejuni* Residues K482 and D483

Non-conserved $PglB_{Cj}$ residues K482 and D483 were simultaneously randomized to 12 non-redundant, chemically diverse amino acids (S, N, I, V, D, G, F, Y, C, L, H, R) by QuikChange using forward oligonucleotide primer 5'-GTA GAT GGT GGA AAG CAT <u>TTW</u> GGT <u>NDT</u> <u>NDT</u> AAT TTT TTC CCT TCT TTT GCT TTA AGC-3' and reverse primer 5'-GCT TAA AGC AAA AGA AGG GAA AAA ATT <u>AHN</u> <u>AHN</u> ACC <u>WAA</u> ATG CTT TCC ACC ATC TAC-3' (mutated codons underlined; N=A, T, G or C; D=A, T or G; W=A or T). Medium copy-number, IPTG inducible plasmid pGVXN407 encoding the gene sequence for wild-type PglB with C-terminal HA tag was used as template. The quality of the library was verified by sequencing of 20 randomly picked clones. All desired nucleotides were detected at the mutated codons and the proportion of clones with wild-type pglB sequence was below 15%. The library, designated Fa, was transformed into the expression strain *E. coli* St1717 (pGVXN150, pGVXN393) and screened in 96 deep-well plates as described previously (Ihssen et al., 2012*, BMC Biotechnology* 12:67). In total 801 clones were screened, exemplary screening results are shown in FIG. 10. Clone Fa8_G10 (marked with a circle in FIG. 10) exhibited significantly increased glycoprotein-specific ELISA signals when rescreened in 8 replicate wells and was found to harbor the double mutation $PglB_{Cj}$ K482R-D483H (Table 4). The amino acid changes K482R-D483H were, introduced into the wild-type pglB sequence of low copy number plasmid pGVXN114 by QuikChange, resulting in plasmid pGVXN635. The wild-type and variant plasmids were transformed into expression strain *E. coli* St1717 (pGVXN150, pGVXN393) and production of CP5-EPA was analysed in triplicate shake flask experiments as described previously (Ihssen et al., 2012, *BMC Biotechnology* 12:67). The double mutant PglB$_{Cj}$ K482R-D483H facilitated a 1.2 to 2.0-fold increase in CP5-EPA levels as determined by sandwich ELISA (FIG. 11).

TABLE 4

Rescreening and sequencing of top-performing clones of library Fa with randomized residues PglB$_{Cj}$ K482 and D483.

| Clone | ELISA absorbance CP5-EPA (450 nm) fold difference to wild-type plasmid pGVXN407 (average value of n = 8 replicate wells) | Significance niveau for increase compared to wild-type PglB (T-test P value) | Sequencing results (amino acid substitutions in PglB$_{Cj}$) |
|---|---|---|---|
| Fa8_G10 | 1.63 | 0.0025 | K482R D483H |
| Fa6_D10 | 1.43 | 0.002 | L480F K482R D483F |
| Fa7_C7 | 1.22 | 0.096 | L480F K482S D483H |

Wild-type PglB$_{Cj}$ and K482R-D483H variant plasmids pGVXN114 and pGVXN635, respectively, were transformed into the expression strain *E. coli* S12457 (pGVXN570, pGVXN393) which expresses *S. aureus* α-hemolysin (Hla) with an engineered glycosylation site. Strains were inoculated from overnight pre-cultures to an OD$_{600}$ of 0.1 in 1-liter flask cultures (SOB medium+Chloramphenicol, Ampicillin, Tetracycline and Spectinomycin) and incubated at 37° C. with shaking. At an OD$_{600}$ of about 1.0 expression of PglB and Hla was induced by adding 1 mM IPTG and 2 g L$^{-1}$ L-arabinose, respectively. In a control experiment IPTG was omitted. Induced cultures were incubated with shaking overnight at 37° C. until harvest. The total incubation time was about 23 h.

In the experiment with induction, 1200 OD were harvested for both strains, while in the experiment without PglB induction, a total of 1500 OD were harvested from the overnight cultures. After washing pelleted cells once with 0.9% NaCl, cells were resuspended to an OD$_{600}$ of 50 in resuspension buffer (25% sucrose, 10 mM EDTA, 200 mM Tris.HCl, pH 8.5). The cell suspensions were rotated for 20 min. Cells were then separated by centrifugation and resuspended to an OD$_{600}$ of 50 in osmotic shock buffer (10 mM Tris.HCl, pH 8.5) and incubated for 30 min under gentle agitation. After another centrifugation step, 20 mM MgCl$_2$, 0.5M NaCl, 10 mM imidazole and 30 mM Tris.HCl (pH 8.0) were added to the supernatant. His-tagged Hla and CP5-Hla were purified from the supernatant (=osmotic shock fluid) following standard procedures. Fractions (1 mL) covering the A$_{280}$ elution peak of all four experiments were analyzed by SDS-PAGE (Coomassie staining), anti-CP5 Western blot and anti-His Western blot (FIG. 12). CP5-specific bands (box with broken lines) were stronger for the strain expressing PglB$_{Cj}$ K482R-D483H (pGVXN635) than for the strain expressing wild-type PglB$_{Cj}$ (pGVXN114). An enhancement was found both in IPTG-induced and non-induced shake flask cultures. The overall intensity of CPS-specific bands in the molecular mass range 50-110 kDa was quantified with ImageJ software (Ref. ImageJ Image Processing and Analysis in Java). The Grey value of the local background was substracted. HisTrap eluates of the strain expressing PglB$_{Cj}$ K482R-D483H contained 2.0-fold more CP5-Hla than that of the strain expressing wild-type PglB$_{Cj}$.

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

REFERENCES

1. Nothaft H & Szymanski C M (2010) Protein glycosylation in bacteria: sweeter than ever. *Nat Rev Microbiol* 8(11): 765-778.
2. Wacker M, et al. (2002) N-linked glycosylation in *Campylobacter jejuni* and its functional transfer into *E. coli*. *Science* 298(5599):1790-1793.
3. Kowarik M, et al. (2006) Definition of the bacterial N-glycosylation site consensus sequence. *EMBO J* 25(9): 1957-1966.
4. Feldman M F, et al. (2005) Engineering N-linked protein glycosylation with diverse O antigen lipopolysaccharide structures in *Escherichia coli*. *Proc Natl Acad Sci USA* 102(8):3016-3021.
5. Wacker M, et al. (2006) Substrate specificity of bacterial oligosaccharyltransferase suggests a common transfer mechanism for the bacterial and eukaryotic systems. *Proc Natl Acad Sci USA* 103(18):7088-7093.
6. Wetter M, et al. (2013) Engineering, conjugation, and immunogenicity assessment of *Escherichia coli* O121 O antigen for its potential use as a typhoid vaccine component. *Glycoconjugate J* 30(5):511-522.
7. Wacker M, et al. (2014) Prevention of *Staphylococcus aureus* infections by glycoprotein vaccines synthesized in *Escherichia coli*. The Journal of infectious diseases 209 (10):1551-1561.
8. Ihssen J, et al. (2010) Production of glycoprotein vaccines in *Escherichia coli*, *Microb Cell Fact* 9:61.
9. Fisher A C, et al. (2011) Production of secretory and extracellular N-linked glycoproteins in *Escherichia coli*. *Appl Environ Microbiol*. 77(3):871-881.
10. Lizak C, Fan Y Y, Weber T C, & Aebi M (2011) N-Linked glycosylation of antibody fragments in *Escherichia coli*. *Bioconjug Chem* 22(3):488-496.
11. Ihssen J, et al (2012) Structural insights from random mutagenesis of *Campylobacter jejuni* oligosaccharyltransferase PglB. *BMC Biotechnol* 12.
12. Anderson P (1983) Antibody-Responses to Hemophilus-Influenzae Type B and Diphtheria-Toxin Induced by Conjugates of Oligosaccharides of the Type-B Capsule with the Nontoxic Protein Crm197. *Infect. Immun.* 39(1):233-238.
13. Passwell J H, et al. (2001) Safety and immunogenicity of improved *Shigella* O-specific polysaccharide-protein conjugate vaccines in adults in Israel. *Infect. Immun.* 69(3):1351-1357.
14. Lockhart S (2003) Conjugate vaccines. *Expert Rev Vaccines* 2(5):633-648.
15. Brynjolfsson S F, Bjamarson S P, Mori E, Del Giudice G, & Jonsdottir I (2008) Neonatal immune response and serum bactericidal activity induced by a meningococcal conjugate vaccine is enhanced by LT-K63 and CpG2006. *Vaccine* 26(35):4557-4562.
16. de Roux A, et al. (2008) Comparison of pneumococcal conjugate polysaccharide and free polysaccharide vaccines in elderly adults: Conjugate vaccine elicits improved antibacterial immune responses and immunological memory. *Clin. Infect. Dis.* 46(7): 1015-1023.

17. Powell K A, et al. (2001) Directed evolution and biocatalysis. *Angewandte Chemie* 40(21):3948-3959.
18. Bommarius A S, Blum J K, & Abraham son M J (2011) Status of protein engineering for biocatalysts: how to design an industrially useful biocatalyst. *Curr. Opin. Chem. Biol.* 15(2):194-200.
19. Arnold F H, Wintrode P L, Miyazaki K, & Gershenson A (2001) How enzymes adapt: lessons from directed evolution. *Trends Biochem Sci.* 26(2): 100-106.
20. Stemmer W P (1994) Rapid evolution of a protein in vitro by DNA shuffling. *Nature* 370(6488):389-391.
21. Reetz M T, Zonta A, Schimossek K, Liebeton K, & Jaeger K E (1997) Creation of enantioselective biocatalysts for organic chemistry by in vitro evolution. *Angewandte Chemie-Int Edit* 36(24):2830-2832.
22. Reetz M T, Wang L W, & Bocola M (2006) Directed evolution of enantioselective enzymes: Iterative cycles of CASTing for probing protein-sequence space. *Angew Chem Int Edit* 45(8): 1236-1241.
23. Reetz M T, Kahakeaw D, & Lohmer R (2008) Addressing the numbers problem in directed evolution. *Chem Bio Chem* 9(11):1797-1804.
24. Reetz M T, Prasad S, Carballeira J D, Gumulya Y, & Bocola M (2010) Iterative saturation mutagenesis accelerates laboratory evolution of enzyme stereoselectivity: Rigorous comparison with traditional methods. *J. Am. Chem. Soc.* 132(26):9144-9152.
25. Schwarz F, et al. (2011) Relaxed acceptor site specificity of bacterial oligosaccharyltransferase in vivo. *Glycobiology* 21(1):45-54.
26. Lizak C, Gerber S, Numao S, Aebi M, & Locher K P (2011) X-ray structure of a bacterial oligosaccharyltransferase. *Nature* 474(7351):350-355.
27. Matsumoto S, et al. (2013) Crystal structures of an archaeal oligosaccharyltransferase provide insights into the catalytic cycle of N-linked protein glycosylation. *Proc. Natl Acad Sci USA* 110(44): 17868-17873.
28. Lizak C, et al. (2014) A catalytically essential motif in external loop 5 of the bacterial oligosaccharyltransferase PglB. *J. Biol. Chem.* 289(2):735-746.
29. Jaffee M B & Imperiali B (2011) Exploiting topological constraints to reveal buried sequence motifs in the membrane-bound N-linked oligosaccharyl transferases. *Biochemistry* 50(35):7557-7567.
30. Jervis A J, et al. (2012) Characterization of the structurally diverse N-linked glycans of *Campylobacter* species. *J. Bacteriol* 194(9):2355-2362.
31. Curd H, Liu D, & Reeves P R (1998) Relationships among the O-antigen gene clusters of *Salmonella enterica* groups B, D1, D2, and D3. *J. Bacteriol.* 180(4): 1002-1007.
32. Jaradat Z W & Zawistowski J (1996) Production and characterization of monoclonal antibodies against the O-5 antigen of *Salmonella typhimurium* lipopolysaccharide. *Appl. Environ. Microbiol.* 62(1): 1-5.
33. Ma S K, et al (2010) A green-by-design biocatalytic process for atorvastatin intermediate. *Green Chem.* 12(1): 81-86.
34. Jochens H & Bornscheuer U T (2010) Natural diversity to guide focused directed evolution. *Chem Bio Chem.* 11(13):1861-1866.
35. Aicolombri U, Elias M, & Tawfik D S (2011) Directed evolution of sulfotransferases and paraoxonases by ancestral libraries. *J. Mol. Biol.* 411(4):837-853.
36. Geremia S, Campagnolo M, Schinzel R, & Johnson L N (2002) Enzymatic catalysis in crystals of *Escherichia coli* maltodextrin phosphorylase. *J. Mol. Biol* 322(2):413-423.
37. Larkin A & Imperiali B (2011) lire expanding horizons of asparagine-linked glycosyiation. *Biochemistry* 50(21): 4411-4426.
38. Tai V W F & Imperiali B (2001) Substrate specificity of the glycosyl donor for oligosaccharyl transferase. *J. Org. Chem.* 66(19):6217-6228.
39. Hildebrand A, Remmeit M, Biegert A, & Soding J (2009) Fast and accurate automatic structure prediction with HHpred. *Proteins* 77 Suppl 9:128-132.
40. Benkert P, Tosatto S C, & Schwede T (2009) Global and local model quality estimation at CASP8 using the scoring functions QMEAN and QMEANclust. *Proteins* 77 Suppl 9:173-180.
41. Lomize M A, Pogozheva I D, Joo H, Mosberg H I, & Lomize A L (2012) OPM database and PPM web server: resources for positioning of proteins in membranes. *Nucleic Acids Res.* 40 (Database issue): D370-376.
42. Fait I C, et al. (1995) Expression of *Shigella dysenteriae* serotype-1 O-antigenic polysaccharide by *Shigella flexneri* aroD vaccine candidates and different *Shigella flexneri* serotypes. *J. Bacteriol.* 177(18):5310-5315.
43. Moreau M, et al. (1990) Structure of the type-5 capsular polysaccharide of *Staphylococcus aureus*. *Carbohydrate Research* 201(2):285-297.
44. Grimont P, Weill F: Antigenic formulae of the *salmonella* servoras. In., 9th edition edn. Geneva: WHO Collaborating Centre for Reference and Research on *Salmonella*; 2007.
45. Rocchetta H L, Burrows L L, Lam J S: Genetics of O-antigen biosynthesis in *Pseudomonas aeruginosa*. *Microbiology and Molecular Biology Reviews: MMBR* 1999, 63(3):523-553.
46. Trautmann M, Held T K, Cross A S: O antigen seroepidemiology of *Klebsiella* clinical isolates and implications for immunoprophylaxis of *Klebsiella* infections. *Vaccine* 2004, 22(7):818-821.
47. Pantophlet R, Nemec A, Brade L, Brade I I, Dijkshoorn L: O-antigen diversity among *Acinetobacter baumannii* strains from the Czech Republic and Northwestern Europe, as determined by lipopolysaccharide-specific monoclonal antibodies. *Journal of Clinical Microbiology* 2001, 39(7):2576-2580.
48. Hossain H, Wellensiek H J, Geyer R, Lochnit G: Structural analysis of glycolipids from *Borrelia burgdorferi*. *Biochimie* 2001, 83(7):683-692.
49. Borud B, Aas F E, Vik A, Winther-Larsen H C, Egge-Jacobsen W, Koomey M: Genetic, structural, and antigenic analyses of glycan diversity in the O-linked protein glycosyiation systems of human *Neisseria* species. *Journal of Bacteriology* 2010, 192(11):2816-2829.
50. Borud B, Viburiene R, Hartley M D, Paulsen B S, Egge-Jacobsen W, Imperiali B, Koomey M: Genetic and molecular analyses reveal an evolutionary trajectory for glycan synthesis in a bacterial protein glycosylation system. *Proceedings of the National Academy of Sciences of the United States of America* 2011, 108(23):96439648.
51. McConville M J, Bacic A, Mitchell G F, Handman E: Lipophosphoglycan of *Leishmania major* that vaccinates against cutaneous leishmaniasis contains an alkylglycerophosphoinositol lipid anchor. *Proceedings of the National Academy of Sciences of the United Stales of America* 1987, 84(24):8941-8945.
52. McConville M J, Ferguson M A: The structure, biosynthesis and function of glycosylated phosphatidylinositols in the parasitic protozoa and higher eukaryotes. *The Biochemical Journal* 1993, 294 (Pt 2):305-324.
53. Astronomo R D, Burton D R: Carbohydrate vaccines: developing sweet solutions to sticky situations? *Nature Reviews Drug Discovery* 2010, 9(4):308-324.

What is claimed is:

1. An N-oligosaccharyl transferase comprising an amino acid sequence having at least 95% identity to SEQ ID NO:1, wherein the N-oligosaccharyl transferase comprises one or more substitutions at positions corresponding to positions in the polypeptide of SEQ ID NO: 1 selected from the group consisting of 77, 80, 196, 311, 462, 482, 483, and 477.

2. The N-oligosaccharyl transferase of claim 1, wherein said N-oligosaccharyl transferase comprises two or more substitutions at positions corresponding to positions in the polypeptide of SEQ ID NO: 1 selected from the group consisting of 77, 80, 196, 311, 462, 482, 483, and 477.

3. The N-oligosaccharyl transferase of claim 1, wherein said N-oligosaccharyl transferase comprises a substitution at a position corresponding to position 311 of the polypeptide of SEQ ID NO: 1.

4. The N-oligosaccharyl transferase of claim 1, wherein said N-oligosaccharyl transferase comprises a substitution at a position corresponding to position 77 of the polypeptide of SEQ ID NO: 1.

5. The N-oligosaccharyl transferase of claim 1, wherein said N-oligosaccharyl transferase further comprises one or more substitutions at positions corresponding to positions in the polypeptide of SEQ ID NO: 1 selected from the group consisting of positions 287, 288, 289, 290, 291, 292, 293, and 294.

6. The N-oligosaccharyl transferase of claim 5, wherein said N-oligosaccharyl transferase comprises one or more substitutions at positions corresponding to positions in the polypeptide of SEQ ID NO: 1 selected from the group consisting of positions 287, 288, 289, and 294.

7. A host cell comprising the N-oligosaccharyl transferase of claim 1 or claim 4.

8. A method of producing a bioconjugate comprising culturing the host cell of claim 7 in a cell culture medium and purifying the bioconjugate from the host cell culture.

9. A nucleic acid encoding an N-oligosaccharyl transferase comprising an amino acid sequence having at least 95% identity to SEQ ID NO:1, wherein the N-oligosaccharyl transferase comprises one or more substitutions at positions corresponding to positions in the polypeptide of SEQ ID NO: 1 selected from the group consisting of 77, 80, 196, 311, 462, 482, 483, and 477.

10. An N-oligosaccharyl transferase comprising an amino acid sequence having at least 95% identity to SEQ ID NO: 2, wherein the N-oligosaccharyl transferase comprises one or more substitutions at positions corresponding to positions in the polypeptide of SEQ ID NO: 2 selected from the group consisting of 79, 82, 314, 488, and 489.

11. The N-oligosaccharyl transferase of claim 10, wherein said N-oligosaccharyl transferase comprises two or more substitutions at positions corresponding to positions in the polypeptide of SEQ ID NO: 2 selected from the group consisting of 79, 82, 314, 488 and 489.

12. The N-oligosaccharyl transferase of claim 10, wherein said N-oligosaccharyl transferase comprises a substitution at a position corresponding to position 314 of the polypeptide of SEQ ID NO: 2.

13. A nucleic acid encoding an N-oligosaccharyl transferase comprising an amino acid sequence having at least 95% identity to SEQ ID NO:2, wherein the N-oligosaccharyl transferase comprises one or more substitutions at positions corresponding to positions in the polypeptide of SEQ ID NO: 2 selected from the group consisting of 79, 82, 314, 488, and 489.

14. A host cell comprising the N-oligosaccharyl transferase of claim 10 or claim 12.

15. A method of producing a bioconjugate comprising culturing the host cell of claim 14 in a cell culture medium and purifying the bioconjugate from the host cell culture.

16. An N-oligosaccharyl transferase comprising an amino acid sequence having at least 95% identity to SEQ ID NO: 1 and a fragment comprising at least 100 consecutive amino acids of SEQ ID NO: 1, wherein the N-oligosaccharyl transferase comprises one or more substitutions at positions corresponding to positions in the polypeptide of SEQ ID NO: 1 selected from the group consisting of 77, 80, 196, 311, 462, 482, 483, and 477.

17. An N-oligosaccharyl transferase comprising an amino acid sequence having at least 95% identity to SEQ ID NO: 2 and a fragment comprising at least 100 consecutive amino acids of SEQ ID NO: 2, wherein the N-oligosaccharyl transferase comprises one or more substitutions at positions corresponding to positions in the polypeptide of SEQ ID NO: 1 selected from the group consisting of 79, 82, 314, 488, and 489.

18. The N-oligosaccharyl transferase of claim 1, wherein said N-oligosaccharyl transferase comprises substitutions at positions corresponding to positions 77 and 311 in the polypeptide of SEQ ID NO: 1.

19. The N-oligosaccharyl transferase of claim 1, wherein said N-oligosaccharyl transferase comprises substitutions at positions corresponding to positions 80 and 311 in the polypeptide of SEQ ID NO: 1.

* * * * *